US010188860B2

(12) United States Patent
Wingeier et al.

(10) Patent No.: US 10,188,860 B2
(45) Date of Patent: Jan. 29, 2019

(54) SYSTEMS, METHODS AND DEVICES FOR A SKULL/BRAIN INTERFACE

(71) Applicant: NeuroPace, Inc., Mountain View, CA (US)

(72) Inventors: Brett Wingeier, San Francisco, CA (US); Daniel Chao, San Francisco, CA (US); Benjamin Pless, Atherton, CA (US); Thomas Tcheng, Pleasant Hill, CA (US)

(73) Assignee: NeuroPace, Inc., Mountain View, CA (US)

( * ) Notice: Subject to any disclaimer, the term of this patent is extended or adjusted under 35 U.S.C. 154(b) by 45 days.

(21) Appl. No.: 15/225,741

(22) Filed: Aug. 1, 2016

(65) Prior Publication Data
US 2016/0339243 A1 Nov. 24, 2016

Related U.S. Application Data

(60) Continuation of application No. 14/223,478, filed on Mar. 24, 2014, now Pat. No. 9,440,064, which is a
(Continued)

(51) Int. Cl.
A61N 1/05 (2006.01)
A61N 1/36 (2006.01)
(Continued)

(52) U.S. Cl.
CPC ........ A61N 1/36025 (2013.01); A61B 5/4064 (2013.01); A61B 5/4076 (2013.01);
(Continued)

(58) Field of Classification Search
CPC .. A61N 1/0529; A61N 1/0531; A61N 1/0534; A61N 1/0536; A61N 1/0539;
(Continued)

(56) References Cited

U.S. PATENT DOCUMENTS 3,998,215 A 12/1976 Anderson et al.
4,141,359 A 2/1979 Jacobsen et al.
(Continued)

FOREIGN PATENT DOCUMENTS

WO 1999055408 11/1999
WO 2006036584 4/2006

OTHER PUBLICATIONS

Cappa, S. F. "Current to the Brain Improves Word-Finding Difficulties in Aphasia Patients", (Sep. 26, 2008), comment on Monti et al., "Improved Naming After Transcranial Direct Current Stimulation in Aphasia" (Dec. 20, 2007), J. Neuro. Neurosurg. Psychiatry 79(4): 451-453 (Online).
(Continued)

Primary Examiner — Tammie K Marlen
(74) Attorney, Agent, or Firm — Loza & Loza, LLP; David S. Sarisky

(57) ABSTRACT

Methods, devices, and systems induce neuromodulation by focusing a source of stimulation through a skull/brain interface in the form of an aperture formed in the skull, a naturally occurring fenestration in the skull, or a transcranial channel. Methods, devices, and systems identify where to locate skull/brain interfaces, accessories that can be used with the interfaces, and features for controlling stimulation delivered through the interfaces. Multiple indications for the skull/brain interfaces include diagnosis and treatment of neurological disorders and conditions such as epilepsy, movement disorders, depression, Alzheimer's disease, autism, coma, and pain.

13 Claims, 30 Drawing Sheets

Related U.S. Application Data division of application No. 12/243,733, filed on Oct. 1, 2008, which is a continuation-in-part of application No. 11/929,801, filed on Oct. 30, 2007, now Pat. No. 9,179,850.

(51) Int. Cl.

| | | |
|---|---|---|
| *A61B 5/00* | (2006.01) | |
| *A61N 1/30* | (2006.01) | |
| *A61N 5/06* | (2006.01) | |
| *A61B 8/08* | (2006.01) | |
| *A61N 1/04* | (2006.01) | |
| *A61N 1/20* | (2006.01) | |
| *A61B 18/02* | (2006.01) | |
| *A61B 18/14* | (2006.01) | |
| *A61B 18/18* | (2006.01) | |
| *A61B 90/10* | (2016.01) | |

(52) U.S. Cl.
CPC .......... *A61B 5/6864* (2013.01); *A61B 8/0808* (2013.01); *A61B 90/10* (2016.02); *A61N 1/0484* (2013.01); *A61N 1/0492* (2013.01); *A61N 1/0529* (2013.01); *A61N 1/0534* (2013.01); *A61N 1/0539* (2013.01); *A61N 1/205* (2013.01); *A61N 1/303* (2013.01); *A61N 5/0601* (2013.01); *A61B 5/4094* (2013.01); *A61B 18/02* (2013.01); *A61B 18/14* (2013.01); *A61B 2018/1807* (2013.01); *A61B 2090/103* (2016.02); *A61N 1/0536* (2013.01); *A61N 1/36017* (2013.01)

(58) Field of Classification Search
CPC .............. A61N 1/0526; A61N 1/36025; A61N 1/0456; A61N 1/0484; A61N 1/36014
USPC ......................................................... 607/139
See application file for complete search history.

(56) References Cited

U.S. PATENT DOCUMENTS

| | | | |
|---|---|---|---|
| 4,328,813 A | 5/1982 | Ray | |
| 5,421,817 A | 6/1995 | Liss et al. | |
| 5,464,446 A | 11/1995 | Dressen et al. | |
| 5,735,885 A | 4/1998 | Howard et al. | |
| 5,843,150 A | 12/1998 | Dressen et al. | |
| 5,980,540 A | 11/1999 | Bruce | |
| 6,006,124 A | 12/1999 | Fischell et al. | |
| 6,016,449 A | 1/2000 | Fischell et al. | |
| 6,210,417 B1 | 4/2001 | Baudino et al. | |
| 6,410,046 B1 | 6/2002 | Lerner | |
| 6,584,347 B1 | 6/2003 | Sinderby | |
| 6,591,138 B1 | 7/2003 | Fischell et al. | |
| 7,033,598 B2 | 4/2006 | Lerner | |
| 7,089,054 B2* | 8/2006 | Palti ........................ | A61N 1/40 607/2 |
| 7,146,217 B2 | 12/2006 | Firlik et al. | |
| 7,174,213 B2 | 2/2007 | Pless | |
| 7,187,960 B2 | 3/2007 | Abreu | |
| 7,236,830 B2 | 6/2007 | Gliner | |
| 7,341,562 B2 | 3/2008 | Pless et al. | |
| 7,565,199 B2 | 7/2009 | Sheffield et al. | |
| 7,601,116 B2 | 10/2009 | Fischell et al. | |
| 8,150,537 B2* | 4/2012 | Tanaka .................. | A61N 1/0531 607/139 |
| 8,417,353 B2 | 4/2013 | Appenrodt et al. | |
| 8,682,449 B2 | 3/2014 | Simon | |
| 8,805,539 B2 | 8/2014 | Appenrodt et al. | |
| 9,033,861 B2 | 5/2015 | Fischell et al. | |
| 9,352,168 B2 | 5/2016 | Fischell et al. | |
| 2001/0051819 A1 | 12/2001 | Fischell et al. | |
| 2002/0116040 A1 | 8/2002 | Lanard et al. | |
| 2003/0149457 A1 | 8/2003 | Tcheng et al. | |
| 2004/0102828 A1 | 5/2004 | Lowry et al. | |
| 2005/0015128 A1 | 1/2005 | Rezai et al. | |
| 2005/0075680 A1 | 4/2005 | Lowry et al. | |
| 2005/0143790 A1 | 6/2005 | Kipke | |
| 2005/0143799 A1 | 6/2005 | Black et al. | |
| 2005/0143800 A1 | 6/2005 | Lando et al. | |
| 2005/0159792 A1 | 7/2005 | Ridder | |
| 2005/0182420 A1 | 8/2005 | Schulte et al. | |
| 2005/0192594 A1 | 9/2005 | Skakoon et al. | |
| 2006/0064139 A1* | 3/2006 | Chung ................... | A61M 21/00 607/45 |
| 2006/0106430 A1 | 5/2006 | Fowler et al. | |
| 2006/0167524 A1* | 7/2006 | Kimura ................ | A61N 1/0456 607/45 |
| 2006/0287686 A1 | 12/2006 | Cullen et al. | |
| 2007/0031341 A1 | 2/2007 | DiMauro et al. | |
| 2007/0038100 A1 | 2/2007 | Nita | |
| 2007/0043268 A1 | 2/2007 | Russell | |
| 2007/0055320 A1 | 3/2007 | Weinand | |
| 2007/0129652 A1 | 6/2007 | Nita | |
| 2007/0179558 A1 | 8/2007 | Gliner et al. | |
| 2007/0288072 A1 | 12/2007 | Pascual-Leone et al. | |
| 2008/0004676 A1 | 1/2008 | Osypka | |
| 2008/0033503 A1 | 2/2008 | Fowler et al. | |
| 2008/0046035 A1 | 2/2008 | Fowler et al. | |
| 2008/0046053 A1 | 2/2008 | Wagner et al. | |
| 2012/0209346 A1 | 8/2012 | Bikson | |

OTHER PUBLICATIONS

PCT International Search Report and Written Opinion for corresponding International Application No. PCT/US2008/081655 (dated Apr. 16, 2009).

International Preliminary Examination Report (IPER) for counterpart International Application No. PCT/US2008/081655 (dated May 14, 2010).

Besio et al., Effects of Noninvasive Transcutaneous Electrical Stimulation via Concentric Ring Electrodes on Pilocarpine-induced Status Epilepticus in Rats, Epilepsia, published online Jul. 25, 2007.

Bikson et al., Effects of uniform extracellular DC electric fields on excitability in rat hippocampal slices in vitro, 2004, J. Physiol. 557:175-190.

Boggio et al., A randomized, double-blind clinical trial on the efficacy of cortical direct current stimulation for the treatment of major depression, 2007, Int. J. Neurophyschopharmacol, 1-6.

Boggio et al., Prefrontal cortex modulation using transcranial DC stimulation reduces alcohol craving: A double-blind, sham-controlled study, Drug Alcohol Depend, published online Jul. 19, 2007.

Boggio et al., Go-no-go task performance improvement after anodal transcranial DC stimulation of the left dorsolateral prefrontal cortex in major depression, 2007, J. Affect. Disord. 101:91-98.

Clay et al., Weighted regularization in electrical impedance tomography with applications to acute cerebral stroke, 2002, IEEE Trans. Med. Imaging 21:629-637.

Fregni et al., Anodal trans cranial direct current stimulation of prefrontal cortex enhances working memory, 2005, Exp. Brain Res. 166:23-30.

Fregni et al., Transcranial direct current stimulation of the unaffected hemisphere in stroke patients, 2005, Neuroreport 16:1551-1555.

Fregni et al., Noninvasive cortical stimulation with transcranial direct current stimulation in Parkinson's disease, 2006, Mov. Disord. 21: 1693-1702.

Fregni et al., A controlled clinical trial of cathodal DC polarization in patients with refractory epilepsy, 2006, Epilepsia 47:335-342.

Fregni et al., A sham-controlled, phase II trial of transcranial direct current stimulation for the treatment of central pain in traumatic spinal cord injury, 2006, Pain 122:197-209.

Fregni et al., Technology Insight: noninvasive brain stimulation in neurology-perspectives on the therapeutic potential ofrTMS and tDCS, 2007, Nat. Clin. Pract. Neurol. 3:383-393.

Goodman et al., Low Frequency sine Wave Stimulation Decreases Seizure Frequency in Amygdala-Kindled Rats, 2002, Epilepsia 43(S7):10.

(56) References Cited

OTHER PUBLICATIONS

Goodman et al., Preemptive Low Frequency Stimulation Decreases the Incidence of Amygdala Kindled Seizures, 2005, Epilepsia 46: 1-7.
Grill, Safety considerations for deep brain stimulation: review and analysis, 2005, Expert. Rev. Med. Devices 2:409-420.
Hebden et al., Three-dimensional optical tomography of the premature infant brain, 2002, Phys. Med. Biol. 47:4155-4166.
Hummel et al., Effects of non-invasive cortical stimulation on skilled motor function in chronic stroke, 2005, Brain 128:490-499.
Hummel et al., Effects of brain polarization on reaction times and pinch force in chronic stroke, 2006, BMC Neurosci. 7:73.
Iyer et al., Safety and cognitive effect of frontal DC brain polarization in healthy individuals, 2005, Neurology 64:872-875.
K.arkar et al., Focal cooling suppresses spontaneous epileptifonn activity without changing the cortical motor thresold, 2002, Epilepsia 43:932-935.
Kennedy et al., "Brain-O-Matic. Can a Jolt From a Nine-Volt Battery Make You Smarter? Happier? Medical Researchers Revive a Discarded Technology and Set the Stage for the Brain Pod," The Phoenix, Feb. 7, 2007, www.thephoenix.com/article_ektid33313.aspx, updated Feb. 7, 2007.
Lu et al., Comparison of Maximum Induced Current and Electric Field from Transcranial Direct Current and Magnetic Stimulations of a Human Head Model, 2007, Piers online 3:178-183.
Marshall et al., Transcranial direct current stimulation during sleep improves declarative memory, 2004, 1. Neurosci. 24:9985-9992, as corrected in J. Neurosci . 25(2).
Marshall et al., Bifrontal transcranial direct current stimulation slows reaction time in a working memory task, 2005, BMC Neurosci. 6:23.
Merrill et al., Electrical stimulation of excitable tissue: design of efficacious and safe protocols, 2005, J. Neurosci. Methods 141:171-198.

National Institute of Neurological Disorders and Stroke, Anticonvulsive Effects of Transcranial DC Stimulation in Pharmacoresistant Focal Epilepsy, NIH Protocol No. 06-N-0187, www.clinicalstudies.info.nih.gov/detail/A_2006-N-0187.html updated 2006.
Nitsche et al., Modulation of cortical excitability by weak direct current stimulation-technical, safety and functional aspects, 2003, Suppl. Clin. Neurophysiol. 56:255-276.
Nitsche et al., Shaping the effects of transcranial direct current stimulation of the human motor cortex, 2007, J. Neurophysiol. 97:3109-3117.
Nunez et al., Comparison of high resolution EEG methods having different theoretical bases, 1993, Brain Topogr. 5:361-36.
Nunez et al., A theoretical and experimental study of high resolution EEG based on surface Laplacians and cortical imaging, 1994, Electroencephalogr. Neurophysiol. 90:40-57.
Rhee et al., Clinical experience of an iontophoresis based glucose measuring system, 2007, J. Korean Med. Sci. 22:70-73.
Rothman et al., Local Cooling: A Therapy for Intractable Neocortical Epilepsy, 2003, Epilepsy Curr. 3:153-156.
Srinivasan, Methods to Improve the Spatial Resolution of EEG, 1999, International J. Bioelectromagnetism 1:102-111.
Suh et al., Blood volume and hemoglobin oxygenation response following electrixal stimulation of human cortex, 2006, Neuroimage 31:66-75.
Sukstanskii et al., An analytical model of temperature regulation in human head, 2004, J. Thermal Biology 29:583-587.
Tanter et al., Time reversal for ultrasonic transcranial surgery and echographic imaging, 2005, J. Acoustical Soc. Amer. 118(3): 1941.
Trivedi, Electrify Your Mind, the New Scientist (2547), www.tmcnet.com/usubmit/2006/04 14/1 573554.html, updated 2006.
Medtronic Sofamor Danek, The METRx X-Tube Retraction System, www.sofamordanek.com/patient-minimal-metrx-xtube.html, updated Jun. 19, 2003.

\* cited by examiner

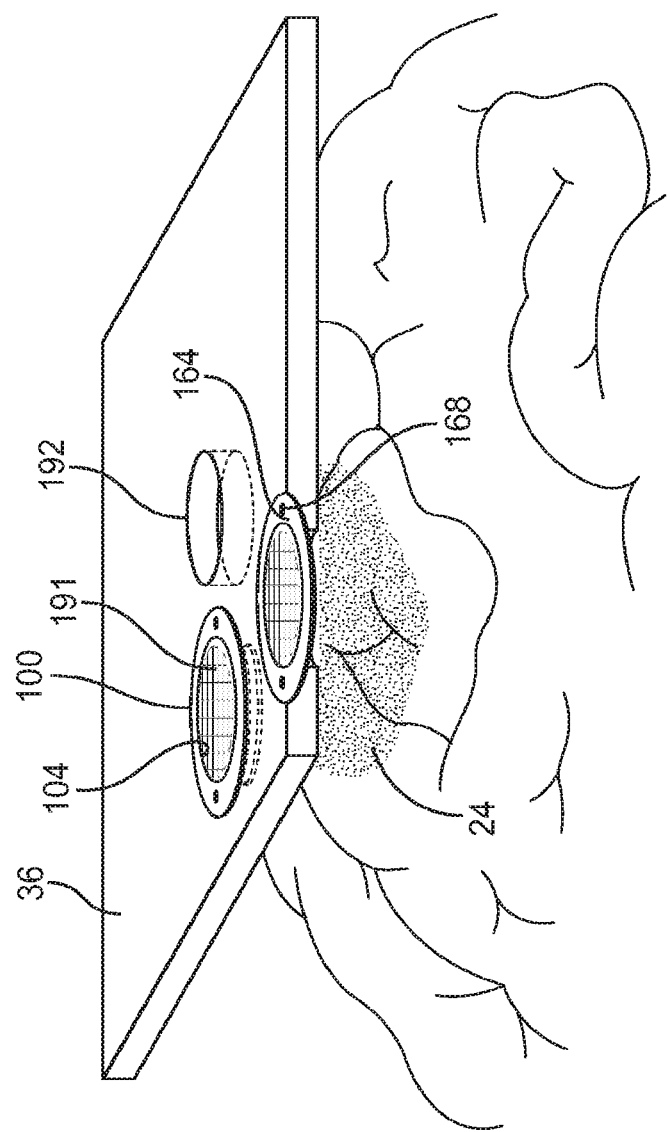

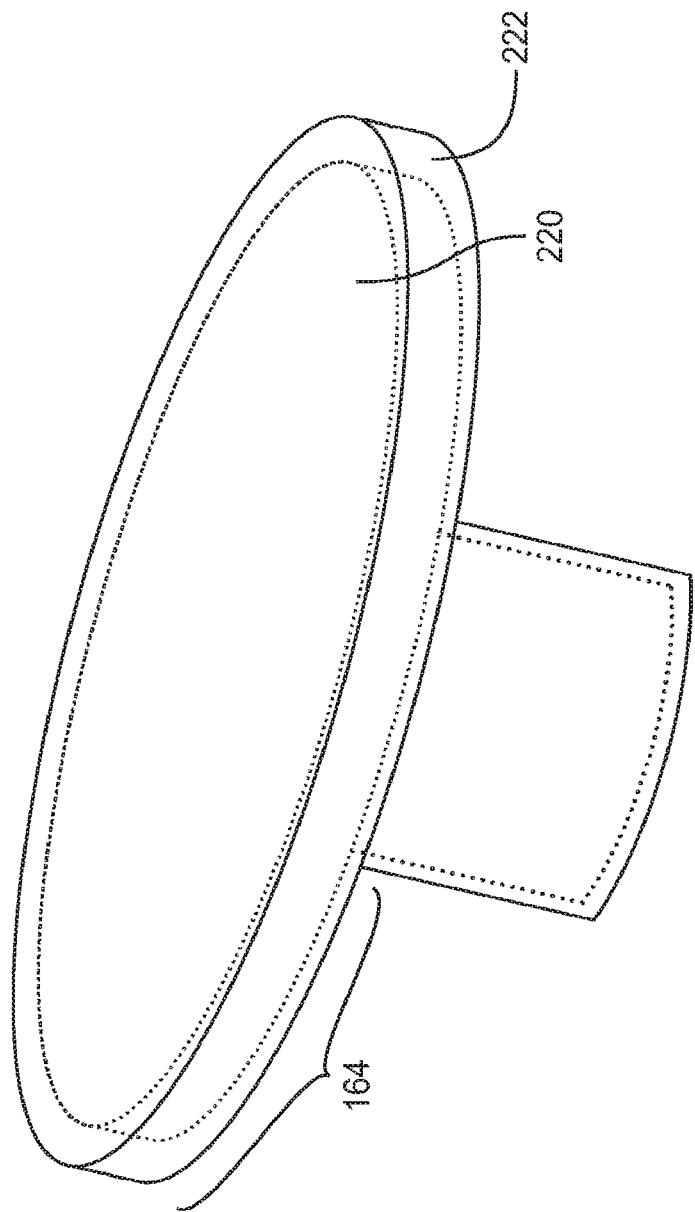

SYSTEMS, METHODS AND DEVICES FOR A SKULL/BRAIN INTERFACE

CROSS-REFERENCE TO RELATED APPLICATION(S)

This application is a continuation of U.S. application Ser. No. 14/223,478 to Wingeier, et al., entitled "Systems, Methods and Devices for a Skull/Brain Interface" and filed Mar. 24, 2014, now U.S. Pat. No. 9,440,064, which is a divisional of U.S. application Ser. No. 12/243,733 to Wingeier, et al., entitled "Systems, Methods and Devices for a Skull/Brain Interface" and filed Oct. 1, 2008, now abandoned, which is a continuation-in-part of and claims priority to pending U.S. application Ser. No. 11/929,801 to Wingeier, et al., entitled "Systems, Methods and Devices for a Skull/Brain Interface" and filed Oct. 30, 2007, now U.S. Pat. No. 9,179,850, each of which is incorporated herein by reference in its entirety.

BACKGROUND

Technical Field

The inventions disclosed herein are directed to systems, devices and methods for establishing an interface through the thickness of the skull for purposes such as delivering some form of neuromodulation (e.g., electrical or optical stimulation, pharmaceutical stimulation or thermal (e.g., cooling or delivering ultrasound to the brain)) to targeted structures in the brain in a controlled manner to modulate neural activity, and detecting signals generated by neurons in targeted structures in the brain.

Background

Much research and clinical development activity is ongoing in the area of using various forms of neuromodulation to affect the brain (e.g., to diagnose or treat a neurological disorder). There is also continuing interest in improving the quality or fidelity with which signals can be sensed or measured from the brain, especially in electroencephalography but also with respect to measurements associated with things such as impedance plethysmography, tomography, and optical imaging.

Electrical Stimulation

Neuronal activity can be measured as electrical signals. This activity also can be modulated (e.g., to inhibit undesired activity by blocking the action potentials that allow the neurons to "fire", to increase or decrease the excitability of a group of neurons, or to cause neurons to fire) by inducing an electric field in neural tissue, or stated another way, in the vicinity of a group of neurons.

One way of inducing an electric field is by conducting electricity to the neural tissue through an electrode-to-tissue interface (ETI). Implantable and partially implantable systems are known which can deliver neuromodulation in this manner. For example, U.S. Pat. No. 6,016,449 to FISCHELL et al., issued Jan. 18, 2000 for a "System for Treatment of Neurological Disorders" describes an implantable neurostimulation system which, through electrodes implanted on the surface of or in the brain, detects signals (referred to as electrocortical signals or "ECoG"s because they are measured directly at the brain as opposed to through the skull, as is the case with a conventional electroencephalogram). The system can be configured so that, when the neurostimulator detects certain types of activity in the ECoGs, e.g., activity that is believed to be associated with a seizure or to be a precursor of a seizure, it will deliver electrical stimulation to targeted areas of the brain in the form of various types of electrical waveforms, with the intention of eliminating seizure activity and/or reducing the severity of the seizures.

The types of waveforms that can be delivered through an electrode-to-tissue interface are limited inasmuch as the charge density per phase has to be low enough to be considered safe and charge balancing must occur. More specifically, in a conventional electrode, current is carried by movement of electrons within the electrode, typically a metallic substance. However in an aqueous, non-metallic environment such as the human body, current is created largely by the movement of ions (charged particles) within the environment. In order for electrical charge delivered by an electrode to pass into and affect the surrounding tissue, the electric current flowing through the electrode must be converted into ion movement in the tissue.

This conversion can happen in two ways, by virtue of capacitance or electrochemical reactions.

More specifically, an electrode interface, such as an electrode-to-tissue interface, is capacitive; that is, it can store a small amount of electrical charge without any actual transfer of charge from electrode to tissue. Consider two pipes attached end-to-end with a rubber membrane separating them. A small amount of flow in one pipe can balloon out the membrane, and, as long as the amount of flow is not great enough to burst the membrane, the net flow of current is transferred to the second pipe. If the flow is then repeatedly reversed (the analogy here being to alternating current), the system appears as if it were one single pipe with no barrier. This occurs, electrically, when small amounts of charge are delivered in a biphasic pulse; the leading phase stores charge in one direction, and the trailing phase removes charge to restore the balance.

If the electrical charge to be passed exceeds the capacitive limit of the electrode-to-tissue interface, then the only remaining way to transfer charge is by electrochemical reactions occurring at the electrode-to-tissue interface. The precise nature of the reactions that occur depend on the voltage across the ETI, but the reactions are almost always undesirable because they can result in, for example, hydrogen ions, hydrogen gas, hydroxide ions, oxygen gas, and other possibly toxic substances being introduced into the tissue, and denaturation of proteins already present in the tissue. The reactions can also result in erosion of the electrode and distribution of the electrode material into the surrounding tissue. Current passed in this way is often referred to as Faradaic current. For the sake of completeness, it is noted that in practice, a small amount of reaction product can be absorbed by a reversed electrochemical reaction on the trailing phase of a biphasic stimulus. This is known as pseudocapacitance. The actual safe charge per phase of a stimulation system (i.e., the amount of charge per phase that does not result in undesirable electrochemical changes in the tissue over time) thus is governed by the sum of the actual capacitance and the pseudocapacitance.

In view of the foregoing, a goal associated with use of electrical neurostimulation systems using implanted electrodes is to keep the charge passed per phase within the capacitive limit of the ETI. The magnitude of this limit is key to safety of electrical neurostimulation, and has been characterized for some materials from which electrodes are commonly fabricated. Platinum, for example, yields a theoretical charge storage capacity of 200 $\mu C/cm^2$ (micro coulombs per square centimeter) and a practical charge storage capacity of 50 $\mu C/cm^2$. Oxide materials such as iridium oxide may reversibly store more than 1000 $\mu C/cm^2$. These charge densities are more than sufficient for pulsatile or high frequency stimulation in most cases. By comparison, a typical deep brain stimulus of 3 mA for a 90 µS pulse width on a 5.7 mm² electrode passes 5 µC/cm². On the other hand, low frequency, non-pulsatile electrical stimulation is constrained in most cases by these limits. For instance, a 1 Hz sinusoid delivered at 1 mA peak-to-peak on a 5.7 mm² electrode passes 2800 µC/cm² per phase. (GRILL, W. M., "Safety Considerations for Deep Brain Stimulation: Review and Analysis," *Expert Rev. Med. Devices* (2005), 2(4): 409-420 and MERRILL, D. R., et al., "Electrical Stimulation of Excitable Tissue: Design of Efficacious and Safe Protocols," *J. Neurosci. Meth*. (2005), 141: 171-198.)

Accordingly, the waveforms used in electrical stimulation delivered through an electrode-to-tissue interface are those which can both maintain charge balancing and either avoid or reverse any electrochemical reactions at the ETI as they begin to occur. Stimulation using waveforms that satisfy these criteria will be referred to herein as "pulsatile stimulation" or "AC stimulation." Examples of these waveforms are biphasic pulsatile waveforms (as are commonly used for deep brain and cortical neurostimulation) (see MERRILL et al., "Electrical Stimulation of Excitable Tissue: Design of Efficacious and Safe Protocols," *J. Neurosci. Meth*. (2005) 141: 171-198), and sinusoidal or near-sinusoidal waveforms at high frequencies such as 100 Hz and above.

There are also neuromodulation techniques which rely only upon an external stimulation source and which are believed to modulate neural activity by inducing a current in neural tissue. One of these techniques is Transcranial Electrical Stimulation or "TES." TES involves applying electrodes to the scalp which, when provided with an electrical signal, result in some current flow in the brain which in turn has the effect of modulating the activity of groups of neurons. TES is usually not a preferred approach to treating a disorder or other condition of a patient, because most of the current from the stimulation flows through the scalp, from electrode to electrode, rather than into the brain, and this current flow causes pain and discomfort, due to stimulation of nerves in the scalp, and contraction of the scalp muscles. It has been used as a form of electroconvulsive therapy (ECT) with the patient under anesthesia, to treat depression.

Transcranial Direct Current Stimulation (tDCS) is another technique to modulate the electrical activity of neurons. In this technique, weak electrical currents (on the order of 0.1 to two milliamps) are applied through electrodes placed externally on the scalp, with conduction to the scalp facilitated by a saline-saturated sponge or a layer of conductive gel. The currents, and the resulting static DC fields, are believed to alter the firing rates of neurons. tDCS is being investigated for use in treatment of several conditions; for example, major depression. For example, in one reported double-blind study, anodal tDCS was applied to the left dorso-lateral prefrontal cortex and was observed to improve mood in 40 patients when compared to both anodal tDCS applied to the occipital cortex (believed to be unrelated to depression) and sham stimulation. (See BOGGIO, P. S., et al., "A Randomized, Double-Blind Clinical Trial on the Efficacy of Cortical Direct Current Stimulation for the Treatment of Major Depression," *Int. J. Neuropsychopharmacol* (2007) 11, 1-6. Another study has reported improved go-no-go task performance in depressed patients using a similar protocol. (See BOGGIO, P. S., et al., "Go-No-Go Task Performance Improvement after Anodal Transcranial DC Stimulation of the Left DorsoLateral Prefrontal Cortex in Major Depression," *J. Affect Disord*. (2006) 101(1-3): 91-8.

tDCS also has been used experimentally to treat a variety of neurological disorders, as well as in experiments designed to study and enhance cognitive function in normal human subjects. Most studies have concluded that tDCS has a mild neuromodulatory effect, often of clinical value and often lasting beyond the immediate stimulation period. A scientific review of experimental, human clinical use of tDCS is provided in FREGNI, F., et al., "Technology Insight: Non-invasive Brain Stimulation in Neurology—Perspectives on the Therapeutic Potential of rTMS and tDCS," *Nat. Clin. Pract. Neurol*. (2007) 3(7): 383-93). There are some articles in the popular press on the subject as well, such as TRIVEDI, B., "Electrify Your Mind—Literally," *New Scientist,* 15 Apr. 2006, and KENNEDY, P., "Can A Jolt From A Nine-Volt Battery Make You Smarter? Happier? Medical Researchers Revive A Discarded Technology and Set the Stage for the 'Brain Pod'," *The Phoenix,* 7 Feb. 2007.

For example, stroke rehabilitation using tDCS, particularly rehabilitation for strokes that caused some type of motor deficit, has been studied by several groups. Anodal tDCS, applied to the area of an ischemic lesion, improved standard measures of motor function in a sham-controlled group of six patients with mild motor deficit (as disclosed in HUMMEL, F., et al., "Effects Of Non-Invasive Cortical Stimulation On Skilled Motor Function In Chronic Stroke," *Brain* (2005) 128:490-00) and in a group of eleven patients with severe motor deficit (as disclosed in HUMMEL, F. et al., "Effects of Brain Polarization On Reaction Times And Pinch Force In Chronic Stroke," *BMC Neuroscience* (2006) 7:73.) In this and other applications, anodal tDCS is believed to be excitatory, increasing cortical excitability and enhancing neural plasticity in the stimulated region. The effect is believed to last somewhat beyond the actual stimulation session.

Further, application of cathodal tDCS to the area contralateral to an ischemic lesion, in addition to anodic tDCS to the lesion area, has been observed to similarly improve motor function in six patients with mild to moderate motor deficit (as disclosed in FREGNI, F., et al., "Transcranial Direct Current Stimulation Of The Unaffected Hemisphere In Stroke Patients," *Neuroreport* (2005) 16: 1551-1555.) In this and other applications, cathodal tDCS is believed to be inhibitory, decreasing cortical excitability and in particular decreasing output of the stimulated region.

Cathodal tDCS, applied over an epileptic cortex, has been shown in at least one report to reduce the number of epileptiform discharges observed within 30 days after stimulation (as disclosed in FREGNI, F., et al., "A Controlled Clinical Trial Of Cathodal DC Polarization In Patients With Refractory Epilepsy," *Epilepsia* (2006) 47(2): 335-342). A trend toward reduced seizure frequency, i.e., not reaching the level of p=0.05 significance, was also observed after cathodal tDCS. It was noted in this study that anodal tDCS, applied over the contralateral, non-epileptic cortex, did not cause increased epileptiform discharges. A similar treatment currently is the focus of a trial sponsored by the National Institute of Neurological Disorders and Stroke for 56 patients (see "Anticonvulsive Effects of Transcranial DC Stimulation in Pharmacoresistant Focal Epilepsy," NIH Protocol No. 06-N-0187 (2006).)

Neurostimulation using pulsatile waveforms applied to the motor cortex has been used for treating chronic pain, especially for pain of neuropathic or central origin. Using tDCS to treat such pain has also been reported. In one study of 17 patients (as disclosed in FREGNI, F., et al., "A Sham-Controlled, Phase II Trial Of Transcranial Direct Current Stimulation For The Treatment Of Central Pain In Traumatic Spinal Cord Injury," Pain (2006) 122: 197-209), anodal tDCS over the primary motor cortex was shown to significantly reduce pain due to fibromyalgia when compared to both sham stimulation and anodal stimulation of the dorso-lateral prefrontal cortex (DLPFC, an area of cortex which is thought to be unrelated to the condition of central pain).

Some are investigating using tDCS for treatment of the movement disorder Parkinson's disease. One report suggests beneficial effects on motor-task scores and motor-evoked potentials in 17 Parkinsonian patients (FREGNI, et. al., "Noninvasive Cortical Stimulation with Transcranial Direct Current Stimulation in Parkinson's Disease," *Mov. Disord.* (2006) 21: 1693-1702.

Still another promising area of tDCS research involves cognitive enhancement in normal human subjects. tDCS administered during slow-wave sleep has been observed to increase retention of memorized word pairs significantly, in comparison with both sham stimulation and tDCS administered in those who are awake. (See MARSHALL, L., et al., "Transcranial Direct Current Stimulation during Sleep Improves Declarative Memory," *J. Neurosci.* (2004) 24 (44): 9985-9992, as corrected in *J. Neurosci.* 25(2).)

Fregni et al. also observed enhanced performance with a working memory task, in 15 subjects, with anodic tDCS applied over the left dorso-lateral prefrontal cortex. (FREGNI, F., et al., "Anodal Transcranial Direct Current Stimulation Of Prefrontal Cortex Enhances Working Memory," *Exp. Brain Res.* (2005) 166(1): 23-30.) This enhanced performance was contrasted to cathodic stimulation of the left DLPFC, which had no effect, and anodic stimulation of the primary motor cortex, which also had no effect and which is believed to be an area of cortex irrelevant to working memory. In another study, Marshall et al. identified significant slowing of reaction time in 12 subjects with bilateral frontal tDCS, during a working memory task (MARSHALL et al., "Bifrontal Transcranial Direct Current Stimulation Slows Reaction Time In A Working Memory Task," *BMC Neuroscience* (2005) 6:23.)

Administration of anodal tDCS over left prefrontal cortex has also been shown to significantly increase verbal fluency in contrast with cathodal tDCS, which resulted in a mild decrease in fluency. (IYER, M. B., et al., "Safety and Cognitive Effect of Frontal DC Brain Polarization in Healthy Individuals," *Neurology* (2005) 64(5): 872-5.)

In addition, one study suggests that alcohol craving can be decreased using anodic-left/cathodic-right and anodic-right/cathodic-left tDCS of the dorso-lateral prefrontal cortex. (BOGGIO, P. S., "Prefrontal Cortex Modulation Using Transcranial DC Stimulation Reduces Alcohol Craving: A Double Blind, Sham-Controlled Study," Drug Alcohol Depend, 17 Jul. 2007.) The effect was demonstrated in 13 subjects to be significant in comparison to sham stimulation, regardless of tDCS polarity.

Some of the difficulties facing researchers investigating various applications of tDCS relate to the ability to focus the stimulation on target areas of the brain and the ability to accurately or repeatedly locate the scalp electrodes to provide the desired stimulation.

Modeling of current and electrical field distribution in tDCS shows that electrical fields sufficient for neuromodulation are widely distributed throughout the brain. (See LU, M, et al., "Comparison of Maximum Induced Current and Electric Field from Transcranial Direct Current and Magnetic Stimulation of A Human Head Model," *PIERS Online* 3(2) (2007) 179-183.)

This is significant, since most applications or potential applications of tDCS will require stimulation of a defined cortical structure, such as the primary motor cortex. Even those applications which involve providing diffuse stimulation of a larger structure, such as the dorsolateral prefrontal cortex, will likely target that structure only, such that stimulation of nearby structures would not be optimum.

Another issue in tDCS may be unfocused and/or undesired stimulation due to the reference electrode. While such stimulation may be mitigated somewhat by placing the reference electrode away from the patient's head, such placement may raise other issues. For example, placing the reference electrode elsewhere may result in unintended neuromodulation of the brain stem, due to the diffuse nature of the current flow. (See NITSCHE, M. A., et al., "Modulation of Cortical Excitability by Weak Direct Current Stimulation—Technical, Safety and Functional Aspects," *Supp. Clin. Neurophysiol.* (2003) 56: 255-76.)

There have been several attempts to address the focality issue with tDCS. It has been shown that smaller stimulating electrodes and larger reference electrodes contribute to focal stimulation. (See NITSCHE, M. A., et al., "Shaping The Effects Of Transcranial Direct Current Stimulation Of The Human Motor Cortex," *J. Neurophysiol.* (2007) 97:3109-3117.) Concentric ring electrodes have also been proposed, and used in an animal model, to provide more focused transcranial DC stimulation and to reduce reference electrode effects. (See BESIO, W. G., et al., "Effects Of Noninvasive Transcutaneous Electrical Stimulation Via Concentric Ring Electrodes On Pilocarpine-Induced Status Epilepticus In Rats," *Epilepsia,* 25 Jul. 2007.) Accurate mapping of electrical properties of the head, and finite element modeling of tDCS current flow, has also been proposed as a way to increase focality of tDCS. (U.S. Patent Application Publication No. 2007/0043268, "Guided Electrical Transcranial Stimulation (GETS) Technique," to RUSSELL, Feb. 22, 2007.) However, all of these techniques are still fundamentally limited by current preferentially flowing through the scalp, and blurring of the intracranial neuromodulatory field due to high skull resistivity. This is analogous to the situation in EEG; resolution is incrementally improved by using more electrodes but a fundamental limit is soon reached, with diminishing returns after about 2.5 cm inter-electrode spacing, due to blurring of the signal by intervening tissue. (See SRINIVASAN, R., "Methods To Improve The Spatial Resolution Of EEG," *Int. J. Bioelectromagnetism* (1999) 1(1):102-111.)

Other techniques for applying electrical stimulation to the brain are under investigation that use waveforms (as opposed to direct current) which do not meet the definition of "pulsatile" or "AC" set forth above, i.e., the waveforms are not suitable for maintaining charge balance and for minimizing undesirable electrochemical reactions at the electrode-to-tissue interface. Stimulation using these waveforms will be referred to in this disclosure as "non-pulsatile stimulation" or "near-DC stimulation." Examples of these waveforms are large amplitude or slowly varying oscillatory waveforms and low frequency sinusoidal waveforms. The nature of these waveforms is such that they exceed the limits of charge density per phase that are deemed safe at the electrode-to-tissue interface or they do not permit charge balancing to be maintained when the waveforms are delivered. Low frequency sinusoidal stimulation has shown some efficacy in animal models of epilepsy. (See GOODMAN, J. H., et al., "Low-Frequency Sine Wave Stimulation Decreases Seizure Frequency In Amygdala-Kindled Rats," *Epilepsia* (2002) 43 (supp7): 10, and GOODMAN, J. H., et al., "Preemptive Low-Frequency Stimulation Decreases The Incidence Of Amygdala-Kindled Seizures," *Epilepsia* (2005) 46(1): 1-7.)

In summary, then, the sources for electrical stimulation discussed above can be conveniently (for the purposes of this disclosure) grouped into these categories: (1) pulsatile or AC stimulation; (2) DC stimulation; and (3) non-pulsatile and near-DC stimulation. Applying electrical stimulation to modulate neural activity through an electrode-to-tissue interface typically requires invasive surgery to implant the electrodes, e.g., deep in the brain, on the cortex (cortical electrodes), or on the dura (epidural electrodes). The type of stimulation that can be delivered through the electrodes is limited, as a practical matter, to pulsatile or AC stimulation, because the waveforms used have an acceptable charge-density-per-phase and maintain charge balancing when delivered. Non-pulsatile or near-DC stimulation and direct current stimulation should not be applied through an implanted electrode-to-tissue interface because of unacceptable charge densities and the inability to maintain charge balancing during delivery. Without the implanted electrode-to-tissue interface, however, focusing the stimulation where it is desired to modulate neural activity is difficult, since the resistance of the skull tends to diffuse the electrical fields so that they are widely distributed throughout the brain. In addition, in tDCS, locating the scalp electrodes inaccurately can lead to errors in delivery of the stimulation, or in interpreting the results.

Magnetic Stimulation

Another technique for neuromodulation that is being explored is referred to as Transcranial Magnetic Stimulation or "TMS." TMS is thought to induce eddy currents in the surface of the brain that stimulate a group of neurons. In this technique, the coil of a magnet is held against the head and energized by rapidly discharging a capacitor, which creates a rapidly changing current in the coil windings. This rapidly changing current sets up a magnetic field at a right angle to the plane of the coil. The magnetic field goes through the skin and skull to the brain and induces a current tangential to the skull. This current influences the electrical activity of the neurons. TMS can be applied on a single-pulse or paired-pulse basis, or repetitively (rTMS). TMS is not associated with the often high level of discomfort that accompanies TES. However, TMS is not favored in surgical environments because of the difficulties presented by having multiple metal objects in the environment. In addition, when used in any environment, TMS equipment is typically bulky to manipulate and consumes a lot of power. Also, the stimulation parameters in TMS tend to be less consistent than those that can be achieved with other types of electrical stimulation. TMS is under investigation for treatment of migraine headaches, amblyopia, and depression, among other neurological disorders and conditions.

Neuromodulation Using Iontophoresis

Iontophoresis refers to the techniques of moving an ionically-charged substance into and through tissue by electromotive force. The basic technique is well known, and has been used for delivering such biologically active agents (also known as bioactive agents) as anti-inflammatory medications, and topical anesthetics. Bioactive agents intended to affect neural tissue also can be delivered via iontophoresis. These agents may include but are not limited to glutamate, acetylcholine, valproate, aspartate, and gamma amino butyrate. Reverse iontophoresis (i.e., extraction of substances, usually for measurement) also is a well known technique in some applications as glucose monitoring. (See, e.g., RHEE, S. Y., et al., "Clinical Experience of an Iontophoresis Based Glucose Monitoring System," *J. Korean Med. Sci.* (2007) 22:70-3.)

Jacobsen, et al. describe early improvements for safety and comfort of Iontophoresis and applications such as transdermal delivery of pilocarpine for diagnosis of cystic fibrosis, and transdermal delivery of anesthetic substances. U.S. Pat. No. 4,141,359 to JACOBSEN et al. for "Epidermal Iontophoresis Device," issued Feb. 27, 1979.

Using waveforms other than DC waveforms in iontophoresis are also known. For example, Liss et al., describes a three-component modulated waveform, reviews other iontophoretic waveforms, and presents results for iontophoretic diffusion of the bioactive substances adrenocorticotropic hormone (ACTH), cortisol, beta endorphin, and serotonin. U.S. Pat. No. 5,421,817 to LISS et al. for "Non-Intrusive Analgesic NeuroAugmentive and Iontophoretic Delivery Apparatus and Management System," issued Jun. 6, 1995.

Iontophoresis also has been recognized as a promising avenue for delivery of substances into the brain. Lerner has proposed iontophoretic administration of pharmaceuticals into the brain tissue via transnasal or transocular paths. U.S. Pat. No. 6,410,046 to LERNER for "Administering Pharmaceuticals to the Mammalian Central Nervous System," issued Jun. 25, 2002.

Lerner further has disclosed iontophoretic administration of bioactive substances to the central nervous system, using a source of bioactive substance that may be implanted at the brain surface. U.S. Pat. No. 7,033,598 to LERNER for "Methods and Apparatus for Enhanced and Controlled Delivery of a Biologically Active Agent into the Central Nervous System of a Mammal" issued Apr. 25, 2006. In addition, Abreu has disclosed iontophoretic delivery of substances via a naturally-occurring physiologic "brain-temperature tunnel" or "BTT." U.S. Pat. No. 7,187,960 to ABREU for "Apparatus and Method for Measuring Biologic Parameters," issued Mar. 6, 2007.

Stimulation Using Light

Techniques using light to modulate the activity of genetically modified neural tissue are well known. (See, e.g., DEISSEROTH, K., et al., "Next-Generation Optical Technologies for Illuminating Genetically Targeted Brain Circuits," *J. Neurosci.* (2006) 26(41): 10380-10386.)

Detecting Brain Activity

EEG

The electroencephalograph, or EEG, is a measurement of scalp potentials resulting from the summed electrical contributions of many neurons. Poor spatial resolution of scalp EEG, due to spatial "blurring" of the signal by the relatively nonconductive skull, is a well known and well understood issue; maximal scalp EEG resolution is on the order of several centimeters, and decreasing inter-electrode spacing past approximately one centimeter yields virtually no improvement, since the signals are already "blurred" by the time they reach the scalp.

Mathematical models such as the spline-Laplacian and dura imaging have been described for preferentially extracting high-spatial-frequency information from the scalp EEG. (See, e.g., NUNEZ, P. L., et al., "A Theoretical and Experimental Study of High Resolution EEG Based on Surface Laplacian and Cortical Imaging," *Electroencephalogr. Clin. Neurophysiol.* (1994) 90(1): 40-57; NUNEZ, P. L., et al., "Comparison Of High Resolution EEG Methods Having Different Theoretical Bases," *Brain Topogr.* (1993) 5(4): 361-4.) These methods, however, still rely on a signal in which high-resolution spatial information is largely lost, and due to fundamental mathematical issues, provide no way of unambiguously reconstructing the unblurred signal.

By placing electrodes directly on the cortex or dura, one can measure electrical signals without experiencing the blurring caused by the skull and tissue that otherwise intervenes between the dura and the external scalp surface. This electrocorticograph, or ECoG, contains significantly more information at fine spatial scales than can be obtained with scalp-recorded signals. Obtaining ECoGs, however, requires invasive surgery to place the electrodes on the cortex or dura. This method of acquiring EEG is usually limited either to acute use or with a chronically implanted device. In acute use, wires are typically run from the electrodes on the cortex through the skin to an external amplifier (e.g., for mapping epileptic foci over several days or weeks). This technique is associated with a risk that the wires or electrodes will become dislodged and that the exposed area may become infected.

If a chronically implanted ECoG detector is used (such as that disclosed in U.S. Pat. No. 6,016,449 to FISCHELL et al., issued Jan. 18, 2000 for a "System for Treatment of Neurological Disorders"), the risk of dislodgment and infection is lessened. However, to implant the device and the electrodes and associated leads is invasive and expensive. Power and other design constraints may limit the extent to which implanted devices can process ECoGs without external equipment.

Impedance Plethysmography and Tomography

Electrical impedance plethysmography is a well-known method for estimating the volume of an anatomical space by measuring electrical impedance at various frequencies. It may be used to measure volumetric or density changes in neural and vascular tissue, such as changes in perfusion, that are associated or thought to be associated with changes in neural activity.

A map of brain plethysmographic changes may be reconstructed from multi-channel scalp impedance measurements, a technique which is called Electrical Impedance Tomography or "EIT". (See, e.g., CLAY, M. T., et al., "Weighted Regularization in Electrical Impedance Tomography with Applications to Acute Cerebral Stroke," *IEEE Trans. Biomed. Eng.* (2002) 21(6): 629-637.) This plethysmographic signal, as measured on the scalp, is blurred in the same way that EEG signals are spatially blurred. Thus, reconstruction of even a crude tomographic image is both mathematically complex and not highly accurate.

Optical Imaging and Tomography

Optical methods for measuring brain activity such as cerebral perfusion and cerebral hemodynamics are well known. Optical sensing currently has been implemented for such things as direct optical recording of intrinsic reflectance signals (ORIS) from the surface of the brain, and transcranial optical tomography, which attempts to mathematically reverse scattering of light to skull and scalp tissue, in order to reconstruct a crude image of brain hemodynamics. (See, e.g., SUH, M., et al., "Blood volume and hemoglobin oxygenation response following electrical stimulation of human cortex," *NeuroImage* (2006) 31:66-75, and HEBDEN, J. C., et al, "Three-dimensional optical tomography of the premature infant brain," *Phys. Med. Biol.* (2002) 47:4155-4166.)

Transferring Energy to and from the Brain

Investigations have suggested that removing energy from the brain may have application in eliminating or reducing the severity of neurological disorders. For example, heat transfer has shown some promise as a technique for neuromodulation. More specifically, heat transfer away from a region of brain tissue (i.e., cooling) is known to reversibly deactivate neural tissue (i.e., the deactivated tissue can be reactivated after the cooling source is withdrawn), and has been shown to suppress spontaneous epileptiform activity in humans. This phenomenon is believed to provide a potential treatment for focal epilepsy. (See, e.g., KARKAR, et al., "Focal Cooling Suppresses Spontaneous Epileptiform Activity without Changing the Cortical Motor Threshold," *Epilepsia* (2002) 43(8): 932-935.) However, engineering of a practical implantable cooling device has proven nontrivial. (See, e.g., ROTHMAN, et al., "Local Cooling: A Therapy for Intractable NeoCortical Epilepsy," *Epilepsy Curr.* (2003) 5(5): 153-56.) Thermoelectric Peltier devices appear to offer promise, but are known to be relatively inefficient. Provision of adequate power, and safe disposal of the resulting heat, are practical design constraints that militate against an implantable cooling system.

Transcranial heat transfer has also been analyzed. (See, e.g., SUKSTANSKII, A. L., et al., "An Analytical Model of Temperature Regulation in Human Head," *J. Themr. Biol.* (2004) 29:583-587.) Surface head cooling can be used during bypass surgery to induce hypothermia, improving low oxygen survivability and affording more time in which to accomplish the bypass procedures. Similarly, the surface of the head can be cooled to reduce inflammation or for other purposes. However, the cooling effect on the brain is usually nominal using this technique, and it is hard to focus, in any event, especially in the presence of normal blood flow.

High intensity focused ultrasound ("HIFU") can ablate tissue deep in the body. It has been used to create lesions in the heart to treat atrial fibrillation and to ablate fibroid tumors. Using HIFU to treat the brain may be desirable insofar it is less invasive than open brain surgery, which may be complicated by neurological deficits, among other things. The skull, however, is a difficult barrier through which to deliver ultrasound energy, because the skull bone has a strong defocusing effect on the externally applied energy. Sophisticated techniques are being investigated to help overcome the ultrasound-scattering effect of bone, such as time-reversal mirrors (See, e.g., TANTER, M., et al., "Time Reversal for Ultrasonic Transcranial Surgery And Echographic Imaging," Abstract, *Acoustical Society of America J.* (2005) Vol. 118; Issue 3, p. 1941), although skull heating during delivery of the ultrasound still presents an obstacle to this type of treatment.

Skull/Brain Interfaces

There have been some methods and devices disclosed for providing an interface through the skull to the brain as an alternative to, on the one hand, external stimulation sources or sensing electrodes and, on the other hand, implanted electrodes with associated implanted or partially implanted equipment.

For example, Lowry et al. have proposed positioning adjustable length intracranial electrodes through the thickness of the skull under local anesthesia, wherein a distal surface or extension of the electrode is adapted to electrically contact a surface of the brain, such as the dura mater, the cerebral cortex, or a deep brain structure. The electrode is then electrically connected to a pulse generator to apply electrical neurostimulation. U.S. Patent Application Publication No. 2004/0102828, published May 27, 2004 to LOWRY et al. for "Methods and Systems Employing Intracranial Electrodes for Neurostimulation and/or Electroencephalography." In one embodiment, Lowry et al. discloses using an electrically conductive elastomer in an intracranial electrode, e.g., a polymeric material filled with a suitable quantity of a conductive metal powder. Lowry et al. also does not disclose using anything other than pulsatile stimulation from a pulse generator to generate electrical neurostimulation of structures in the brain. (See, e.g., U.S. Patent Application Publication No. 2004/0102828 [0077].)

Lowry et al. have also proposed an intracranial electrode having a head and a shaft such that a proximal portion of the head is flush with the outer layer of the skull. U.S. Patent Application Publication No. 2005/0075680, published Apr. 7, 2005 to LOWRY et al. for "Methods and Systems for Intracranial Neurostimulation and/or Sensing". Lowry et al. also disclose an intracranial electrode with an "electrical energy transfer mechanism" or "ETM" that is placed externally adjacent a patient's scalp to couple electrical energy from a pulse generator to an intracranial electrode having a core using an electrically conductive material in conjunction with a conductive gel layer in an intracranial electrode system. (See, e.g., U.S. Patent Application Publication No. 2005/0075680 [0138]-[0141], FIGS. 34A & B and FIG. 39.)

Fowler et al. have proposed a method using an electrode implanted in a patient's skull to transfer stimulation signals (e.g., from a pulse generator) through the scalp to a target neural population. U.S. Patent Application Publication No. 2006/0106430, published May 18, 2006 to FOWLER et al. for "Electrode Configurations for Reducing Invasiveness and/or Enhancing Neural Stimulation Efficacy, And Associated Methods."

The Lowry et al. and Fowler et al. references disclose only skull/brain interfaces through which signals are delivered or sensed using metal as a conductor. In addition, the only form of stimulation deliverable by any of the devices disclosed in the Lowry et al. references is pulsatile electrical stimulation.

SUMMARY

Before the present systems, devices and methods are described, it is to be understood that this disclosure is not limited to the particular systems, devices and methods described, as these may vary. It is also to be understood that the terminology used in the description is for the purpose of describing the particular versions or embodiments only, and is not intended to limit the scope.

It must also be noted that as used herein and in the appended claims, the singular forms "a," "an," and "the" include plural references unless the context clearly dictates otherwise. Thus, for example, reference to a "transcranial channel" is a reference to one or more transcranial channels and equivalents thereof known to those skilled in the art, and so forth. Unless defined otherwise, all technical and scientific terms used herein have the same meanings as commonly understood by one of ordinary skill in the art. Although any methods, materials, and devices similar or equivalent to those described herein can be used in the practice or testing of embodiments, the preferred methods, materials, and devices are now described. All publications mentioned herein are incorporated by reference. Nothing herein is to be construed as an admission that the embodiments described herein are not entitled to antedate such disclosure by virtue of prior invention.

Described herein is a system and method for providing an interface through the skull to the brain of a patient. In the system and method, the interface can be used for delivering a form of neuromodulation to the brain, including but not limited to thermal (e.g., cooling the brain), electrical pulsatile or AC, DC, and non-pulsatile or near-DC stimulation, neuromodulation or treatment using iontophoresis, and optical neuromodulation. In this embodiment, the system and method includes forming one or more apertures in the skull, or using one or more fenestrations preexisting in the skull, that extend all the way through the thickness of the skull or partially through the thickness of the skull, and providing a source for the stimulation in the vicinity of the aperture(s) or fenestration(s).

In the system and method, the interface also can be used for conveying information from the brain externally of the skull for external measurement or processing, including but not limited to for an electroencephalogram, for impedance plethysmography and associated tomography, and for optical imaging and associated tomography. In this embodiment, the system and method includes forming one or more apertures in the skull, partially or all the way through the skull, or using one or more fenestrations preexisting and/or naturally-occurring in the skull, and providing a means for sensing one or more parameters that is understood or believed to be characteristic of a state or physiological process of the brain.

Further described herein are systems, devices, and methods using one or more transcranial channels to provide a skull/brain interface for facilitating such things as the delivery of neuromodulation to the brain, measuring signals from the brain, and cooling the brain.

In the system and method, complementary components and assemblies may be used to encourage or enhance conduction from an external source of stimulation to the brain or to an external measuring or detection device or system from the brain. Such complementary components include a scalp electrode pad and scalp electrode pad assembly.

The transcranial channel may be provided having an outer wall and an interior cavity and may be constructed of an ion-permeable material in whole or in part. The outer wall may be formed in whole or in part of a substance that is not permeable to ions or the outer wall may be coated or otherwise surrounded on the exterior with such a material.

The interior cavity may be open at both the proximal and distal ends thereof, such that when the channel is positioned in the skull, the interior cavity is left to be filled by the body with one or more of serum or tissue (e.g., fibrous tissue, or in-scalp growth). These substances are significantly more ion-permeable (and thus ion-conductive) than the skull tissue removed when the channel is implanted. Serum, especially, which may be expected to fill the cavity well before any tissue ingrowth occurs, is a fluid containing ions, similar to cerebrospinal fluid ("CSF"), and thus is highly conductive to ion flow.

The interior cavity may be fillable or filled or partially filled with an ion-permeable substance other than air, such as a saline solution, a hydrogel, a porous silicone, or a sponge; the matrix of this permeable substance may be infiltrated with a bioactive material such as an antiproliferative agent, for example atomic silver, bone morphogenic proteins, ciliary neurotrophic factor, ribavirin, sirolimus, mycophenolate, mofetil, azathioprine, paclitaxel, or cyclophosphamide, or a bactericidal and/or bacteriostatic agent, for example quinolone, fluoroquinolone, beta-lactam, aminoglycoside, penicillin, macrolide, monobactam, lincosamide, tetracycline, cephalosporin, lipopeptide, streptogramin, carbapenem, sulfonamide, aminoglycoside, oxalodinone, nitrofuran, ketolide, glycylcycline families of antibiotics, or silver ions. Other types of bioactive agents may also be used.

In one variation, an end cap or cover, for example in the form of a permeable or semi-permeable membrane, may be provided at one or both of the proximal or distal ends of the channel.

The transcranial channel may be provided with an overall length that is designed to traverse the entire thickness of the skull or only a part of thickness of the skull, e.g., 90% of the thickness of the skull.

In one variation, the length of the channel is about the same as the overall width of the channel.

In another variation, the channel may be provided as a plug formed from an ion-permeable material.

Any of the channels, for example, the channel with the interior cavity or the channel in the form of a plug, may be provided with a taper from the proximal end to the distal end thereof.

In a still further variation, the overall width of the channel is much greater than the length of the channel. This variation further may be designed to fit in an aperture or naturally-occurring or otherwise preexisting fenestration in the skull or over an aperture or fenestration in the skull.

In another variation, the transcranial channel may be provided with a plurality of inner lumens. The inner surface of the outer layer may rest on the outer surface of the inner lumen or a gap may be provided between the inner lumen and the outer layer. The outer layer may be formed using a non ion-permeable material, such materials including but not limited to metals, non-permeable silicone, and polymers such as polyetheretherketones. This outer layer will help prevent conduction into the trabecular (also known as cancellous or spongy) bone of the skull of the signal or parameter being conveyed through the channel, e.g., for neuromodulation or measurement or energy transfer.

Optionally, the exterior surface of the channel, e.g., the exterior surface of the outer layer where an outer layer is provided, may be provided as threaded, knurled, ridged or otherwise textured so as to help fit the channel into the skull and/or to retain it in the skull. Each inner lumen may be provided with the same length, or the inner lumens may have varying lengths.

One or more inner lumens may be fillable, filled or partially filled with an ion-permeable substance (e.g., a hydrogel), or left open to be filled by the body with one or more of serum, fibrous tissue, or some in-scalp growth.

Each of the inner lumens may be provided with a hexagonal cross-section or a cross-section of some other suitable shape (e.g., circular, rectangular). Optionally, the channel may be provided with a lip or tabs, with or without screw holes, to help retain it in position once implanted in the skull. If the channel is designed to replace a significant portion of the skull or part of the skull, then the channel may be provided with a curvature that approximates the curvature of the skull to be replaced.

In accordance with a still further variation, a transcranial channel is provided as a thin, cannula-like device (e.g., with a diameter of on the order of one to several millimeters), such that the overall width of the channel is much less than the length of the channel. This cannula-like channel may be formed in whole or in part of an ion-permeable material. The cannula-like channel may be provided with a small bore open at both ends thereof or with an inner lumen surrounded in whole or in part by an outer layer.

In yet another embodiment, a channel for providing a skull/brain interface to facilitate transfer of energy, such as thermal energy, away from the brain is disclosed. The channel is constructed substantially from a material with high thermal conductivity, and provided with an outer wall, coating, or other covering, constructed from a biocompatible material and, optionally, with a rim or lip to increase the extracranial area of the device and the area available for heat conduction. An additional embodiment may include a channel provided with an interior cavity that is filled, partially filled, or fillable with a fluid that may condense at temperatures cooler than about 32.degree. C. and vaporize at higher temperatures, so that the channel may act as an efficient heat pipe to conduct heat away from the brain.

In still other embodiments, a channel for providing a skull/brain interface to facilitate transfer of energy, such as high-frequency ultrasound energy, towards the brain is disclosed. The channel is constructed substantially of a material that is mostly transparent to ultrasound and has dimensions that are characterized by a substantially constant radius and a substantially constant length to facilitate delivery of the ultrasound signals to the brain with minimal distortion, thus enabling good focusing of the signals.

The devices, systems and methods further may be used with elements for temporarily or permanently disabling the conduction of neuromodulation or other interventions to the brain or the transmittal of physiological signals or other information from the brain. Such elements include stoppers and other shields, which may or may not require resection of or incisions into the scalp in order to implement.

Additionally described herein are skull/brain interfaces that include one or more valves in an interface that can be selectively operated to keep closed and to fully or partially open each interface for conduction of signals, drugs or other energy from an external source to the brain or transmittal of physiological signals or conduction of energy from the brain. The valves may be provided with a current or voltage detector, or an active channel device, to monitor and or limit currents or voltages in the interface at any particular time.

In accordance with yet another embodiment, a transcranial channel may be provided with a metallic coil or coils or other devices, such as an RFID chip, to aid in positioning external equipment, such as signal recording instrumentation (e.g., EEG machine) or electrical stimulation sources (e.g., pulse generators or DC current generators), relative to the channel. If the transcranial channel is provided with an external lip, the coil(s) or other device(s) may be provided attached to or embedded in the lip.

In still other variations, one or more RFID elements may be used to identify particular patients to external equipment or any other device or system with which a skull/brain interface is to be used and for other identifying purposes, and to control permissible dosages of stimulation or drugs to the patient (particularly when the patient has some control over delivery of stimulation or drugs).

In accordance with another embodiment, an extracranial, subcutaneous extension is provided, where the extracranial, subcutaneous extension extends from the skull/brain interface to a point distant from the cranial breach. For example, the extracranial extension may extend from the skull/brain interface to another location on the skull, the neck or the shoulder.

In accordance with a still further embodiment, a combination of one or more transcranial channels and one or more transparenchymal channels is disclosed, where each transparenchymal channel may be formed entirely of an ion-permeable substance or having an inner lumen that is in communication with an inner lumen of a transcranial channel. Optionally, an extraparenchymal collector may be used with the combination to facilitate conduction through the skull/brain interface, and to remove the need for direct mechanical coupling of the transcranial channel(s) to the transparenchymal channel(s).

Also described herein are methods for deploying or implanting one or more transcranial channels in the skull of a patient by way of a craniotomy, craniectomy (e.g., drilling of a burr hole), and using a dilator or series of dilators.

Additionally described herein are systems and methods for identifying where to locate one or more skull/brain interfaces (aperture or channel) including targeting with evoked responses (e.g., TMS-evoked responses) and using overlays and/or low-resolution stereotaxy.

Still further described herein are kits with components for facilitating skull/brain interfaces including one or more of the following, for example: an overlay and/or low-resolution stereotaxy assembly; a plurality of channels of various sizes, shapes and lengths; channels with inner lumens of varying lengths; a scalp electrode pad or scalp electrode pad or scalp electrode pad assembly; a stimulation source with or without a headpiece or helmet.

Also described herein are systems and methods for gauging skull thickness in a particular patient before or during installation of a skull/brain interface, such as an ultrasonic tool or an ultrasonic transducer at the end of a drill.

Further described are methods for deploying or implanting a combination of one or more transcranial channels and an extracranial extension and a combination of one or more transcranial channels with one or more transparenchymal channels.

Further described herein are methods for providing an interface through the skull to the brain of a patient using one or more transcranial channels for direct current stimulation, non-pulsatile and near-DC electrical stimulation, pulsatile and AC stimulation, neuromodulation or treatment using iontophoresis, and neuromodulation with light.

Further described herein are methods for providing an interface through the skull to the brain of a patient using one or more transcranial channels for neurosensing from the brain, for example, for measurement of an EEG, impedance plethysmography and tomography, and optical imaging and tomography.

Also described herein is a method for providing an interface through the skull to the brain of a patient using one or more transcranial channels for conducting heat away from a target area of the brain.

Further described herein is a method for providing an interface through the skull to the brain of a patient using one or more transcranial channels for High Intensity Focused Ultrasound ("HIFU").

Additionally described herein are aspects of stimulation used with skull/brain interfaces, including limited patient-controlled stimulation in a portable stimulator, remote-controlled stimulators, and current control and impedance measurement for a stimulation source.

Further described herein are some indications for a skull/brain interface, such as diagnosis of, relief of the symptoms of, or reversal or repair of damage caused by, neurological dsyfunction caused by neurological damage, neurologic disease, neuodegenerative conditions and/or other conditions. The neurological dysfunction may be related to, for example, epilepsy, movement disorders, traumatic brain injury, cerebral palsy, multiple sclerosis, Alzheimer's disease, dementia, memory disorders, stroke, aphasia, mild cognitive disorders, sleep disorders, depressive disorders, anxiety disorders, Tourette's syndrome, restless leg syndrome, coma, learning disorders, autism, speech disorders, auditory or hearing disorders (e.g., tinnitus), craving and addictive disorders, migraine headaches, and other dysfunctions caused by brain injury or characterized by chronic pain.

Additionally described are some specific systems and methods for using a skull/brain interface for particular indications, such as: sleep staging and selective stimulation; performance-enhancing stimulation (e.g., vision-enhancing, memory-enhancing, verbal-fluency enhancing, and enhancing creative state); using DC fields for axonal regrowth; using DC stimulation to treat cognitive dysfunction as in Alzheimer's disease; psychiatric disorders; coma; tinnitus, DC stimulation for language and verbal skills; pain, autism, neuroprotection for stroke, and addictions and cravings.

BRIEF DESCRIPTION OF THE DRAWINGS

Aspects, features, benefits and advantages of the embodiments described herein will be apparent with regard to the following description, appended claims and accompanying drawings where:

FIG. 15 is a schematic view of a method of positioning the channel of FIG. 14.

FIG. 18B is a perspective view of the transcranial channel depicted in FIG. 18A.

DETAILED DESCRIPTION

The inventions are described below with reference to detailed illustrative embodiments. It is apparent that systems according to the inventions can be embodied in a wide variety of forms. Consequently, the specific structural and functional details disclosed herein are representative and do not limit the scope of the inventions. Further, the embodiments disclosed herein are described in the context of systems, methods and devices for providing interfaces between the exterior of the skull and the interior of the skull and/or brain for purposes of modulating neural activity, detecting, measuring and processing parameters characteristic of brain states, and energy transfer from inside the skull to outside the skull or vice versa, because the embodiments disclosed herein have particular utility in this context. However, the embodiments herein can also be used in other applications, as will be apparent to those with skill in the art.

Figure 1:
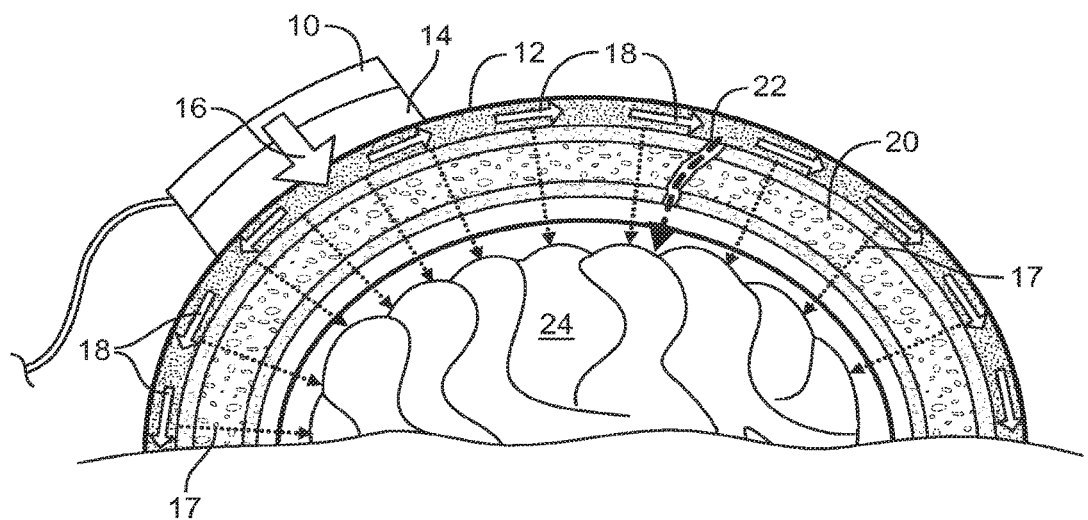
FIG. 1 is a side, cross-sectional, schematic view of current path in a prior art system and method for applying electrical neurostimulation to a patient's brain.

FIG. 1 is a cross-sectional, schematic view of a portion of the scalp, skull and brain during transcranial application of current. The current is applied external to the body from a first pole of a current source (e.g., a pulsatile or DC current source) to a second pole located elsewhere (e.g., elsewhere on the patient's head). A layer of conductive gel 14 is disposed between the first pole 10 of the current source and the scalp 12. Ideally, the current travels from the first pole 10 to the second pole (not shown) through a target area 24 in the brain. As a practical matter, however, the current, shown originating from the first pole 10 with the arrow 16, will be diffused significantly on its way to the target area 24, because there are paths of lesser resistance through the scalp 12, as illustrated by the arrows 18 (in three dimensions, of course, the current would tend to diffuse through the scalp in all directions, not just in the direction of the arrows 18 shown). (In a typical person, the skull is on the order of 40 times more resistant to current than is the scalp.) What current is directed through the skull 20 likewise will be diffuse and only incidentally focused on the target area 24, as shown by the arrows 17 in FIG. 1. Moreover, if there should be a naturally-occurring foramen 22 in the skull 20 (a occurrence that is not all that uncommon), then whatever current is not dispersed in the scalp 12 will tend to flow through the foramen 22, since it is a path of lesser resistance than can be found in the intact skull 20. Thus, even if the first pole 10 of the current source is accurately positioned over the area of the brain 24 to be targeted for neuromodulation, current will tend to flow elsewhere than towards the target area if a foramen is located outside the area of the skull that corresponds to the target area of the brain.

A method of providing a brain/skull interface now will be described with reference to FIG. 2. A skull/brain interface is created by accessing a selected area on the exterior of the skull, for example, by making an incision through the skin 30 and the scalp tissue 32 to create a flap and folding the flap back. An aperture 34 is formed in the skull using a drill or other suitable instrument over a target area 24 of the brain.

Figure 2:
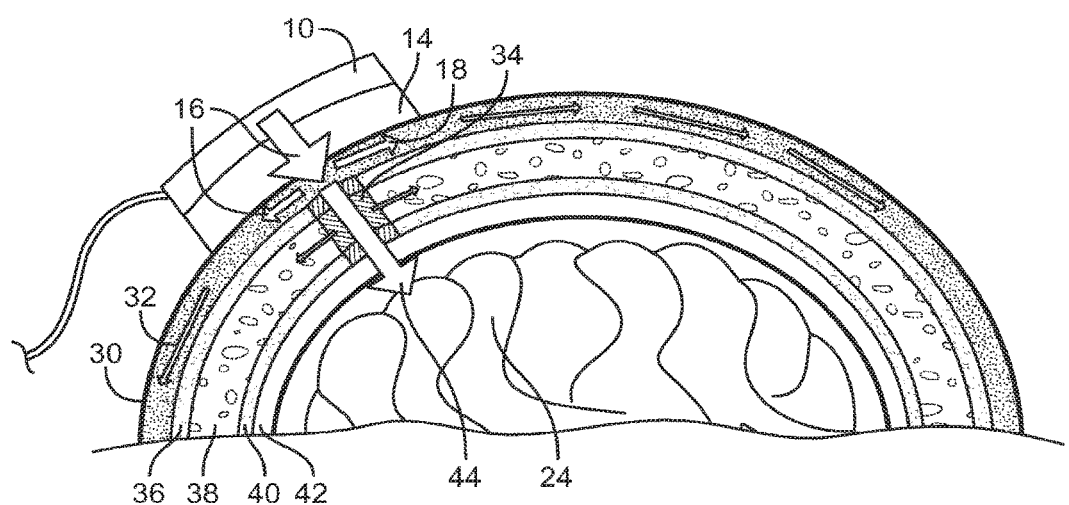
FIG. 2 is a side, cross-sectional, schematic view of current path in a system and method according to the invention for applying electrical neurostimulation to a patient's brain.

In FIG. 2, the aperture 34 extends through all layers of the skull, i.e., through the outer layer of cancellous bone 36, the spongiform bone 38, and the inner layer of cancellous bone 40, and breaches the inner layer of cancellous bone so that the aperture is exposed to the extradural space 42. In a variation of the method, the aperture 34 may be formed so that it extends only part way through the skull 20. For example, the aperture 34 may be formed so that it extends through all three layers of the skull but is just short of breaching the inner layer of cancellous bone 40 so as to not breach the extradural space 42.

In variations where the aperture 34 does not extend all the way through to the extradural space, conduction through the aperture 34 may be somewhat less efficient than in the case where the aperture 34 extends through to the extradural space. However, these variations may be preferred when it is desired to avoid penetrating the skull entirely, for example, to lower the risk of infection. In one embodiment, the aperture 34 is formed so that it extends through about 90% of the thickness of the skull 20.

Although the aperture 34 shown in FIG. 2 is generally cylindrical, the aperture can be formed with other shapes, provided that there is a substantially direct path through the aperture 34, as indicated by the arrow 44, through which conduction can occur. (Although not shown in FIG. 2, it will be understood that, if the skull/brain interface is being used to conduct away from the target area 24 to the exterior of the skull, then the arrow 44 would be pointing in the opposite direction.)

After the aperture 34 is formed, the surgeon may flush or purge the aperture 34 with a saline solution to cleanse the area and otherwise prepare it for immediate use.

The flap in the scalp is then replaced (or the scalp is otherwise repositioned over the aperture 34) and the site of the incision is sutured or otherwise closed.

If the skull/brain interface is to be used for conducting a form of neuromodulation to the brain target area 24, then the neuromodulation source is situated in the vicinity of the proximal end of the aperture 34, i.e., the end of the aperture at the outer layer 36 of the skull. This may be accomplished immediately after the aperture 34 is formed and the scalp flap is replaced, or some period of time later. It will be appreciated, however, that the body's natural response to the formation of the aperture 34 may be healing or tissue proliferation, which may cause partial or complete re-closure of the aperture 34 over time. While this response may well be desirable as, for example, when the neuromodulation is only intended to be delivered in a short-term course of therapy or for a rehabilitation period, the time lag between formation of the aperture 34 and association with the neuromodulation source should be calculated with the possibility of re-closure in mind.

The neuromodulation source shown in FIG. 2 is a current source (for delivering pulsatile, DC, or nonpulsatile/near-DC stimulation), although it will be appreciated that other neuromodulation sources can be substituted for the current source, such as a source for optical neuromodulation or a source for iontophoretic delivery of substances.

When the neuromodulation source is a current source, a layer of conductive gel 14 optionally can be provided between the first pole 10 of the current source and the skin of the scalp in the vicinity of the proximal end of the aperture 34, i.e., the end of the aperture at the outer layer 36 of the skull. Alternatively, other means for improving conduction from the neuromodulation source to the aperture 34 may be provided. In one variation as a sponge soaked in saline may be provided for conduction.

Figure 3A:
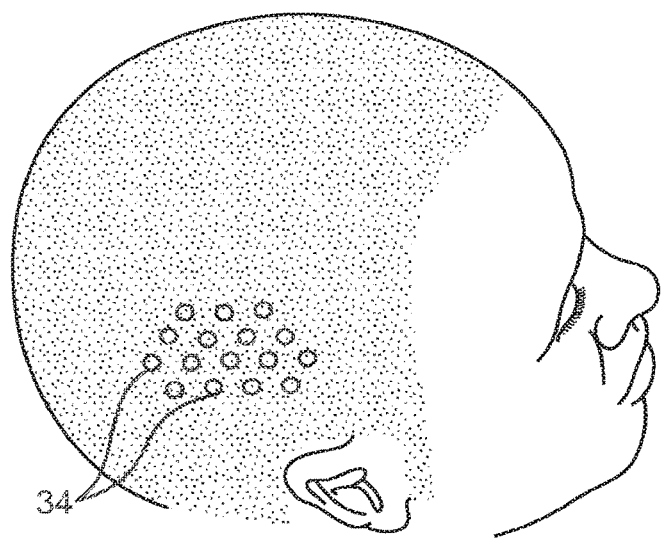
FIG. 3A is a schematic view of the skull of a patient having skull/brain interfaces according to the invention.
Figure 3B:
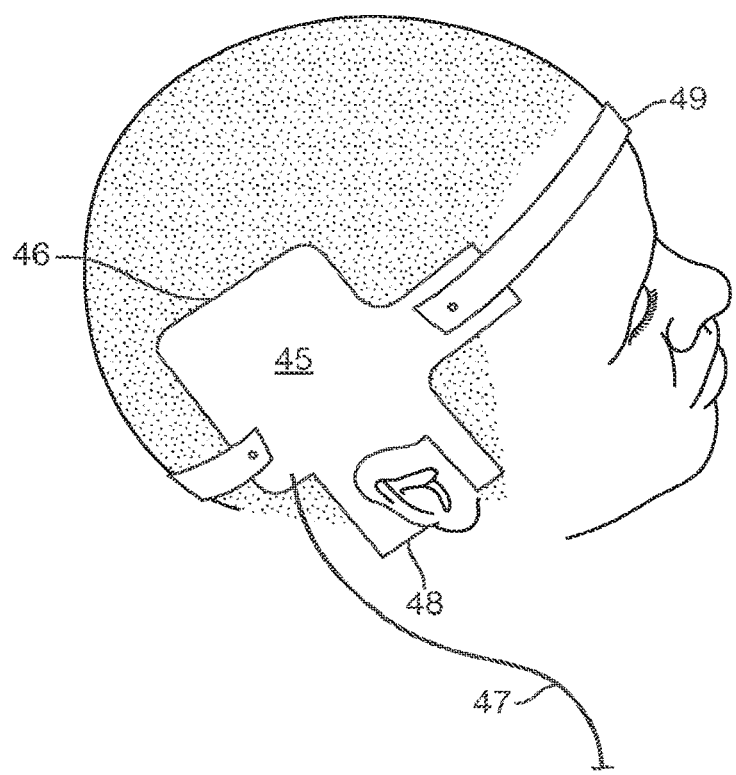
FIG. 3B is a schematic view of the skull of a patient on which a scalp electrode pad assembly has been situated.

In another variation, and referring now to FIGS. 3A and 3B, one or more scalp electrode pads 46 may be provided that can be placed between the external current source and the scalp, over or in the vicinity of the skull/brain interface(s) (e.g., aperture(s) or other fenestration(s). A plurality of apertures 34 are shown in FIG. 3A. Each scalp electrode pad 46 is formed at least in part from a conductive material or substance, so that when put in place between the current source, on the one hand, and the scalp and the apertures, on the other hand, current will preferentially be delivered to the apertures 34 associated with the conductive material or substance.

With further reference to FIG. 3B, one or more scalp electrode pads 45 may be provided in a scalp electrode assembly 46. In one variation, a scalp electrode pad 45 may be connected to a stimulation source (not shown in FIG. 3B) via at least one lead 47. In a variation, a non-conductive strip of material may extend between a scalp electrode pad 45 and an electrode being used as a reference electrode for stimulation (or measurement) (not shown in FIG. 3B), in order to control the relative position of the electrodes. The scalp electrode pad assembly 46 may be provided with an optional feature that allows it to be oriented on the head with respect to some anatomical marker or landmark, such as a traditional landmark used in positioning electrodes for EEG, for example, a nasion. The orienting feature 48 shown in FIG. 3B is intended to be positioned relative to a patient's ear. The scalp electrode assembly 46 may further be provided with an optional feature for aiding in securing the assembly on the patient. The securing feature 49 shown in FIG. 3B, is a strap.

Although the scalp electrode pads and assembly are described herein with reference to facilitating conduction from an external source of neuromodulation into the brain, it will be apparent to one skilled in the art that the scalp electrode pads and assembly may also be used to facilitate detecting physiological information from the brain as described herein.

When the stimulation source is activated, and owing to the presence of the aperture 34, current will flow in the direction of the arrow 16 and the arrow 44, in a substantially direct path to the target area 24 of the brain at which neuromodulation is desired to occur. Some current will be diffused through the scalp 12, as indicated in FIG. 2 by the arrows 18, but the degree of diffusion will be much less than in the case where no aperture 34 is formed. Some current also will be diffused through the spongiform bone 38 though which the aperture 34 extends. Again, however, the amount of diffusion will be less than in the case where neuromodulation is attempted through an intact skull. The method of providing a skull/brain interface also can be applied to convey information externally to the skull from or about one or more brain states, for example, for an EEG or for other neurosensing modalities, including but not limited to impedance plethysmography and tomography and optical imaging and tomography. In one variation, the location for the aperture 34 is selected so that it will be over a target area 24 of the brain from which it is desired to sense electrical signals corresponding to neural activity for an EEG. The aperture 34 is formed and prepared for use in the manner described above with respect to FIG. 2.

Figure 4:
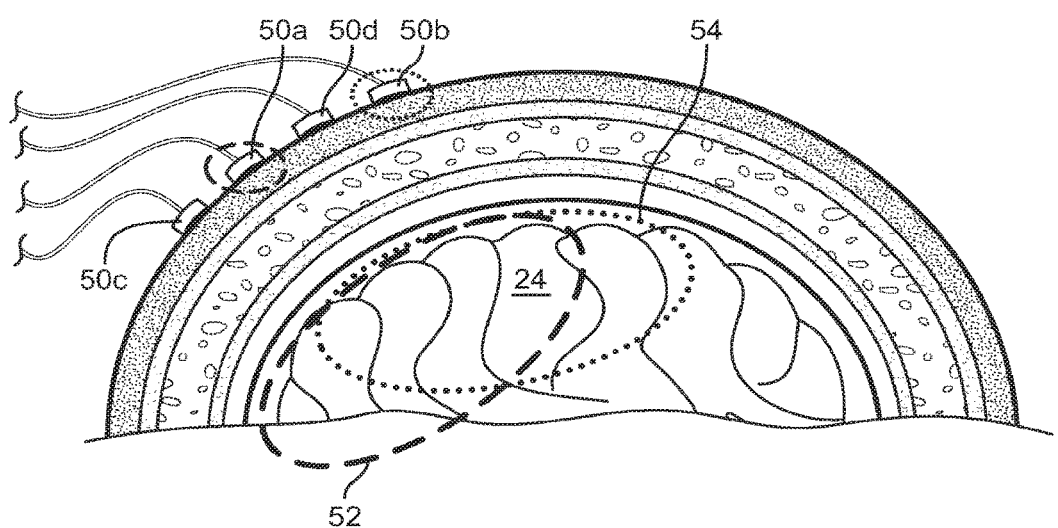
FIG. 4 is a side, cross-sectional, schematic view of a prior art system and method for acquiring signals for an EEG.

FIG. 4 illustrates one conventional method for acquiring signals for an EEG. Scalp electrodes 50a-50d are shown placed on the scalp over the target area 24 of the brain from which electrical activity is desired to be measured. The area of the brain that will contribute signals to the measurements obtained from scalp electrode 50a is illustrated by the dashed line 52, and the area of the brain that will contribute signals to measurements obtained from scalp electrode 52b is illustrated by the dotted line 54. Areas 52 and 54 are relatively large and overlap each other significantly because the presence of the skull impedes the spatial resolution of the electrodes 50a-50d and contributes to blurring of the electrical potentials that are sensed by the electrodes.

Figure 5:
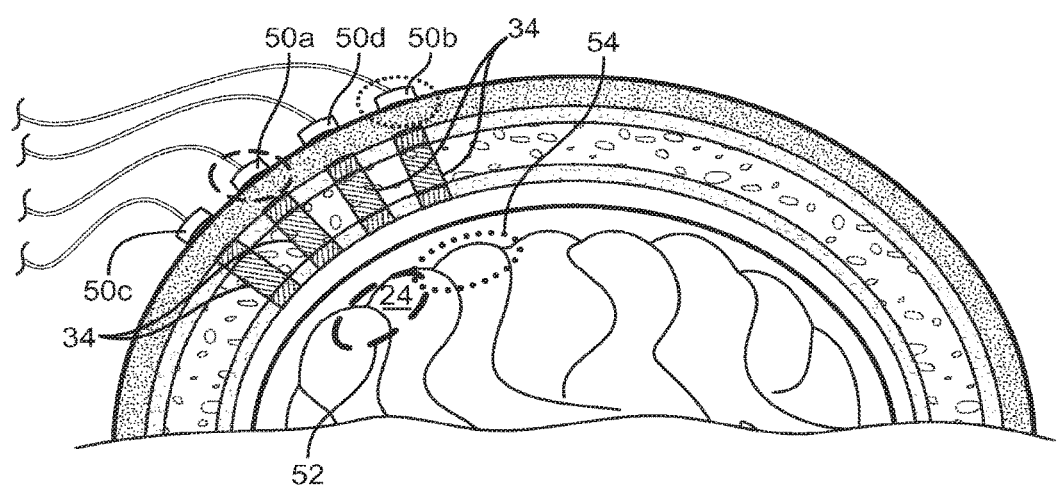
FIG. 5 is a side, cross-sectional, schematic view of a system and method according to the invention for acquiring signals for an EEG.

Referring now to FIG. 5, a method of providing a skull/brain interface for acquiring signals for an EEG is illustrated. Four apertures 34 are shown formed in the skull 20 over the target area 24. After the scalp is replaced over the apertures, scalp electrodes 50a-50b are placed over the proximal ends of each aperture 34. As illustrated by the dashed lines 52 and 54, the two areas of the brain that will contribute to the signals measured by the electrode 50a and 50b are much smaller than in the case of the conventional EEG measurement. In addition, the areas 52 and 54 have little overlap with each other. Thus, the spatial resolution of the signals sensed is improved upon, and the resultant measurement will be characterized by less blurring than in when a conventional method for obtaining an EEG is used.

While four apertures 34 are shown in FIG. 5, any number of apertures may be used in connection with the method.

Although the method of providing a skull/brain interface for sensing a parameter characteristic of a brain state has been described in connection with sensing electrical activity for an EEG, it will be appreciated that other neurosensing modalities can be achieved with the method.

For example, electrical impedance measurements at different frequencies may be obtained through the apertures 34 for estimating the volume of an anatomical space, as in impedance plethysmography. The impedance measurements may be used to map plethysmographic changes in the brain, as in Electrical Impedance Tomography (EIT). By providing a well-defined path through the otherwise relatively non-conductive skull, improvements in spatial resolution and degree of blurring may be realized with this method over conventional methods for performing similar techniques.

It will be appreciated that regardless of the purpose of the skull/brain interface and the relative time the aperture is intended to remain patent (e.g., for acute or chronic procedures), the apertures could be closed off with plugs designed to fit in the channels or into a socket associated with the aperture to, for example, block ion movement through the aperture and/or to discourage infection in the brain cavity. The plugs could be used to disable the aperture for its intended use temporarily or to close off the channel permanently when it is no longer needed.

Transcranial Channels

A device and method of providing a skull/brain interface will now be described with reference to FIGS. 6-17.

Figure 6:
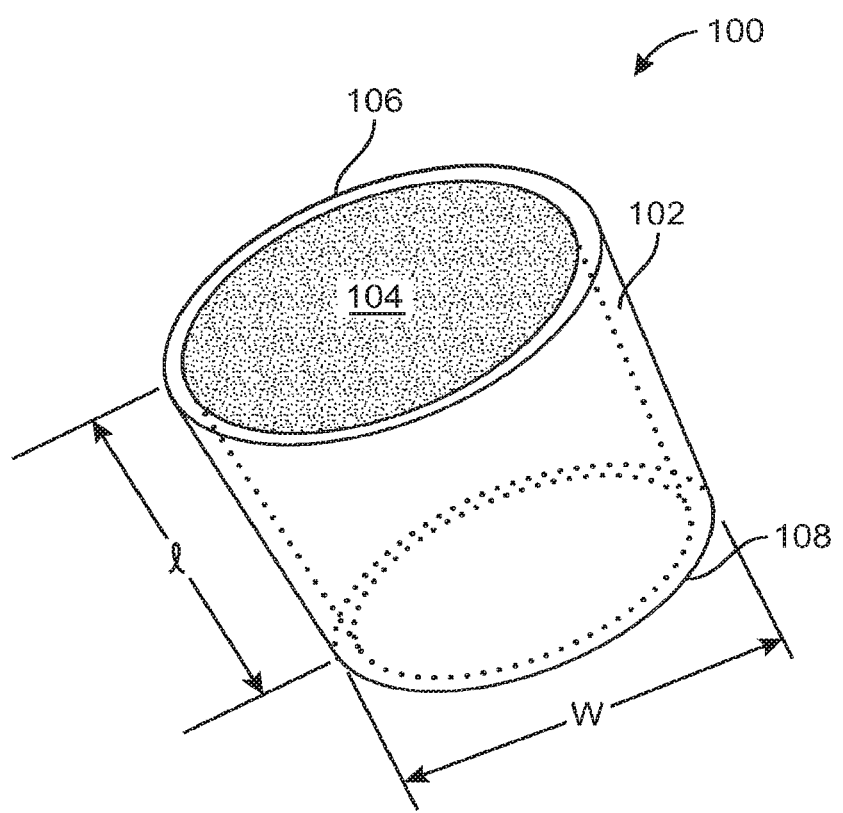
FIGS. 6-10 each is a perspective view of a variation of a transcranial channel.

FIG. 6 illustrates a variation of a transcranial channel 100 that is intended for insertion in an aperture formed in the skull of a patient to provide a skull/brain interface, e.g., for delivering a form of neuromodulation to the brain, sensing a parameter or parameters from the brain, or transferring heat from the brain exteriorly of the skull. The transcranial channel 100 is generally cylindrical, but it will be appreciated that the channel may be provided with any shape provided that the shape selected allows for a substantially direct path from the exterior of the skull through the channel.

The channel 100 has an outer wall 102 that defines an interior cavity 104. The outer wall provides mechanical stability to the channel and is formed from a biocompatible material. The biocompatible material may include but is not limited to a metal such as titanium or stainless steel, or a biocompatible polymer (e.g., polyurethane, polytetrafluoroethylene, polyetheretherketone, polyester, polyamide (e.g., nylon)).

The biocompatible material of the outer wall 102 may be formed from a material that is not generally permeable to ions to discourage conduction in a path other than the desired path. Alternatively, the outer wall 102 may be provided with a coating on all or a portion of the outer wall 102 that includes a generally non-ion-permeable substance for the same purpose of discouraging unwanted conduction. (Non-ion-permeable metallic, biocompatible substances (e.g., titanium or stainless steel) are usually suitable for use in the outer wall when the channel is intended for use in connection with the application of DC stimulation because the voltage at the metal-to-tissue interface developed by typical stimulation amplitudes is usually not sufficient for conduction of DC current into or out of the metallic substance itself.)

The channel has a proximal end 106 that is intended to be oriented at the proximal end of the aperture 34 into which the channel is inserted, i.e., the end of the aperture at the outer layer 36 of the skull. The channel has a distal end 108 that is intended to be oriented towards the brain. In FIG. 6, the proximal and distal ends 106, 108 are left open to the air, or (when implanted) to the sub-scalp and extradural space, respectively, which eventually may result in the channel being filled or partially filled with ion-permeable body serum or tissue.

In other variations, a channel 100 may be provided with an end cap or cover for one or both of the proximal and distal ends 106, 108, for example, in the form of a membrane manufactured from a suitable biocompatible material. The end cap(s) or cover(s) may be provided affixable or affixed to the channel and nonremovable, or affixable or fixable to the channel and removable. Suitable materials for an end cap or cover may include but are not limited to porous silicone, porous polyurethanes, or a mesh or grid of any non-porous biocompatible polymers.

An end cap or cover may be desirable to help retain a substance that is used to fill or partially fill the interior cavity, such as a hydrogel or saline solution. A cover in the form of a membrane on one or both of the proximal and distal ends 106 and 108 of the channel 100 may be deemed especially desirable in some circumstances. For example, after the channel has been implanted, a membrane may discourage migration of any bacteria or pathogens that might be present in the subcutaneous space into the intracranial space.

In the case where a transcranial channel is intended to be used for neuromodulation by iontophoresis, a semipermeable membrane may be provided for a cover to prevent iontophoresis of large or otherwise undesirable molecules into the intracranial space.

In still other variations, a channel 100 may provided without an end cap or cover but with the cavity 104 filled or partially filled with a substance that is understood or believed to facilitate conduction for the particular application for which the channel is to be used. For example, in an application where the channel is intended to be used to facilitate DC stimulation of a target area of the brain, the cavity 104 may be filled with an ion-permeable substance such as porous silicone, porous polyurethanes, saline solutions, hydrogels, or porous masses constructed by sintering together particles of a nonporous polymer such as polyurethanes, polytetrafluoroethylene, polyetheretherketones, polyesters, or polyamides (e.g., nylon). In another example, the cavity 104 may be may be filled, partially filled or fillable with a substance substantially in the form of an open-pore sponge infiltrated with an antiproliferative agent, for example bone morphogenic proteins, ciliary neurotrophic factor, ribavirin, sirolimus, mycophenolate, mofetil, azathioprine, paclitaxel, cyclophosphamide, or atomic silver, where the presence of the antiproliferative agent may prevent cell proliferation and tissue growth after the channel has been implanted in the skull.

The cavity 104 may be filled or partially filled with the ion-permeable substance at the time it is placed in the skull or, if end caps are provided, at some time before deployment (e.g., at the time of manufacture or as a part of the preparation for the surgery).

The channel 100 may be provided with a length l that is designed to traverse the entire thickness of the skull. In other variations, the length l of the channel may be designed to traverse only part of the way through the skull. For example, the channel might be provided with a very short length l relative to the thickness of the skull, such that it provides a sort of a lid for the aperture upon implantation (see, e.g., FIGS. 14 and 15). In another example, the channel might be provided with a length l that approximates about 90% of the thickness of the skull. These latter variations may be preferable to use when it is desirable to avoid breaching the inner layer 40 of the skull 20 with the channel 100. The conduction of signals through the channel 100 will be less efficient than in the case where the channel traverses the entire thickness of the skull, but will still be more efficient than if no channel at all were used to facilitate conduction or otherwise to provide a skull/brain interface. In these variations, it is expected that it would be desirable to provide channels with a thickness, l, that is designed to be about ten percent less thick than the skull thickness, in order to avoid penetrating the skull entirely but nevertheless affording good conduction through the channel.

In FIG. 6, the channel 100 has an overall width, w, corresponding to the diameter of the cylinder, that is approximately the same as the length l, although it will be appreciated that the ratio between the overall width w and the length l may be varied to best serve the application(s) to which the channel is intended to be put.

Figure 7:
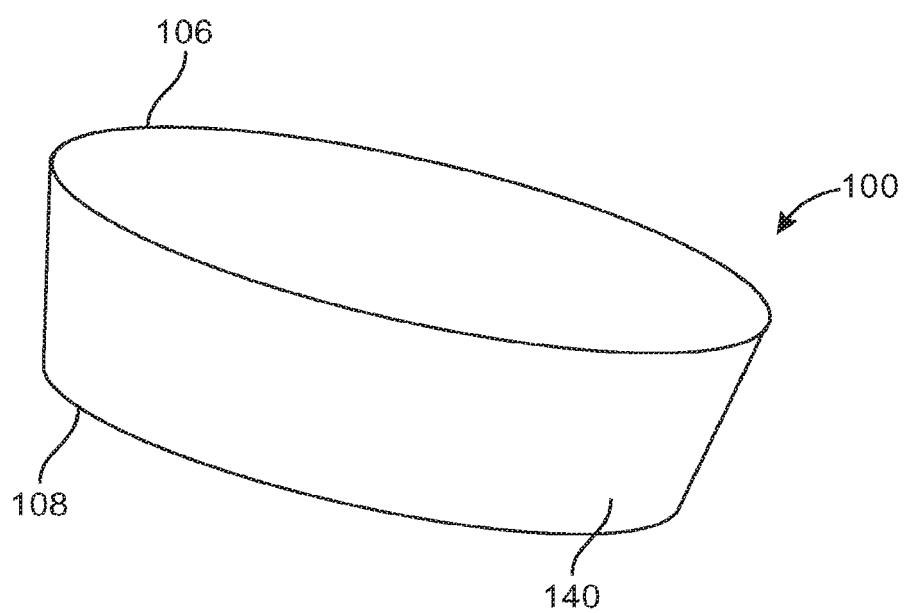

Another variation of a transcranial channel 100 is shown in FIG. 7. The channel 100 is provided in the form of a plug 140 formed from a material well suited for the intended application of the channel. The material may be an ion-permeable substance when an intended application is to use the channel to facilitate DC stimulation of the brain. In FIG. 7, the channel is shown having a generally cylindrical shape that is characterized by a taper so that the plug narrows from the proximal end 106 to the distal end 108. The taper may help prevent the channel 100 from being pushed into the aperture formed in the skull to a greater degree than intended. Other variations of the plug 140 may be provided having different shapes as was the case of the channel 100 described in connection with FIG. 6, above. Other variations of the plug 140 may be provided with different ratios of overall width to length, and with different angles of taper or no taper at all.

Figure 8:
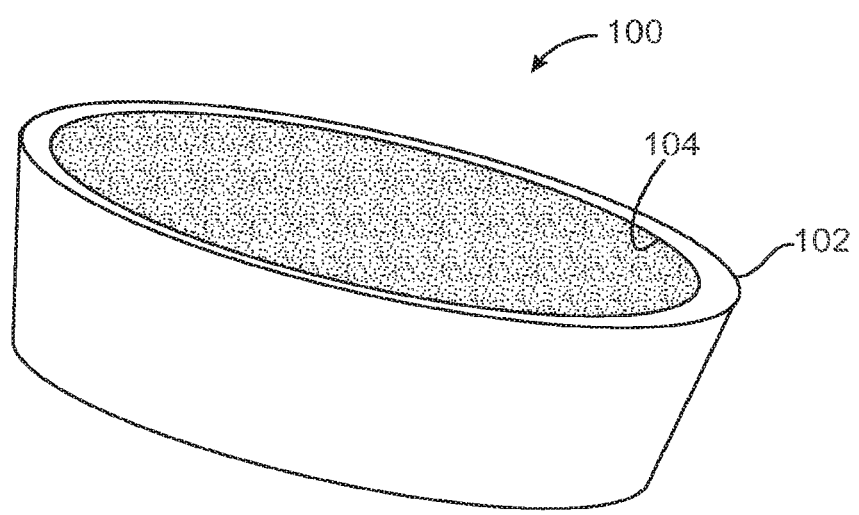

Still another variation of a channel 100 is shown in FIG. 8. This variation is similar to the tapered variation of FIG. 7 however, this variation an outer wall 102 and an interior cavity 104 into which, optionally, a substance such as an ion-permeable substance (other than air) may be introduced.

Figure 9A:
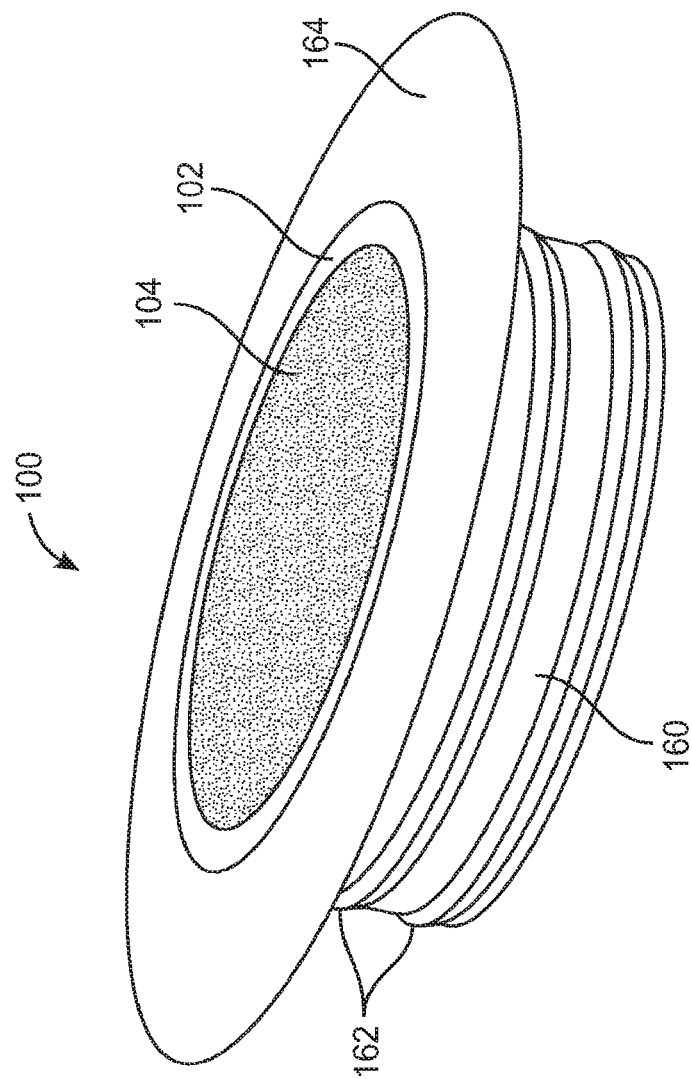

In FIG. 9A, a variation of a channel 100 is shown in which an interior cavity 104 is defined by an outer wall 102 and the exterior surface 160 of the outer wall 102 (i.e., the surface opposite the surface adjacent the interior cavity) is provided with ridges 162. The ridges 162 may assist in securing the channel 100 in the skull. In other variations, the exterior surface 160 may be knurled, threaded or otherwise textured. Any of these exterior surfaces 160 are likely to increase the forces between the exterior surface and the skull to help keep the channel 100 in the desired position.

The channel 100 optionally may be provided with a rim or lip 164 that extends outwardly from the proximal end 106 of the channel. The rim or lip 164 may be formed from the outer wall 102 or the lip 164 may be provided as a separate component of the channel 100, as is shown in FIG. 9A. The lip 164 will help keep the channel in the desired position in the skull and will help to prevent the channel from being pushed further into the skull than intended.

Figure 9B:
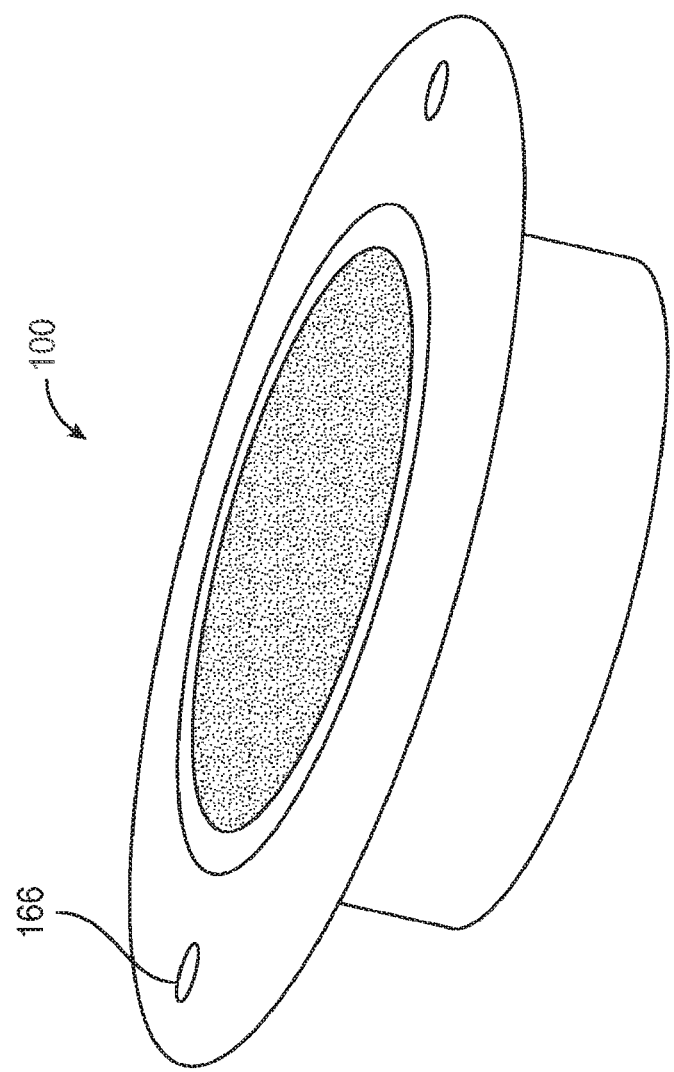

In still another variation of the channel 100, as illustrated in FIG. 9B, the channel is provided with a lip 164 extending out from the proximal end 106 of the channel having screw holes 168. After the channel 100 is placed in the desired position in the skull, screws can be screwed into the skull through one or more screw holes 168 to help maintain that position. The number of screw holes 168 that are provided in a given channel 100 may vary with the size of the channel, for example, a channel having a relatively large overall width may be provided with more screw holes than a channel with a relatively small overall width.

Figure 10:
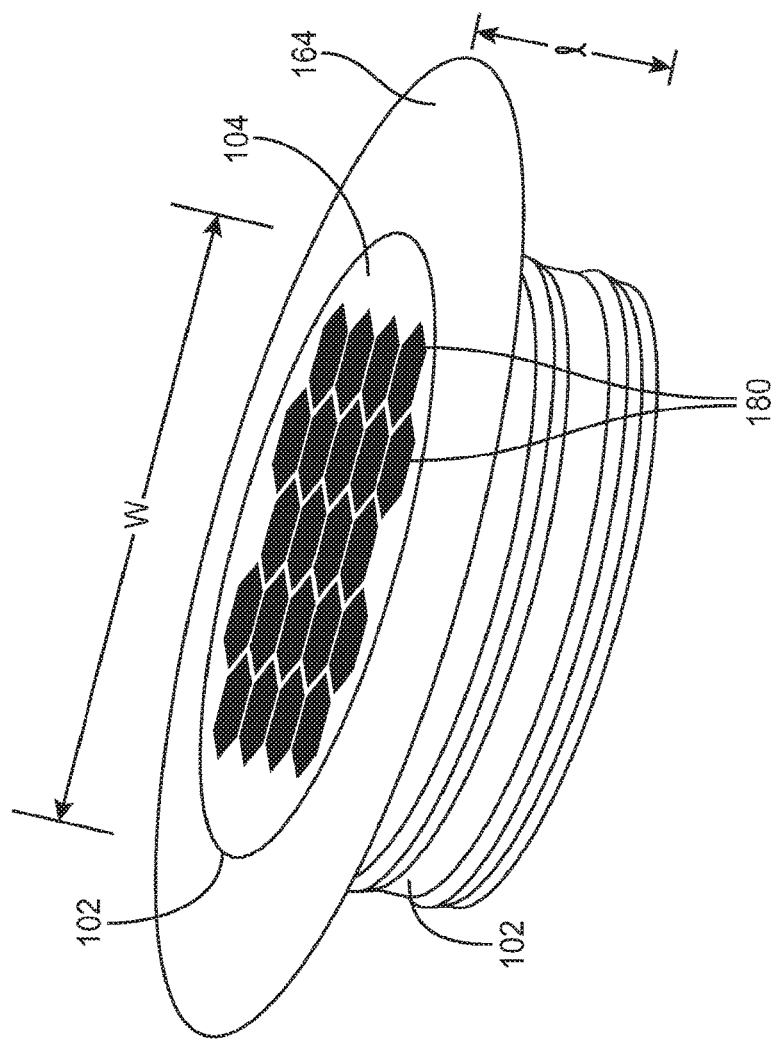
Figure 11:
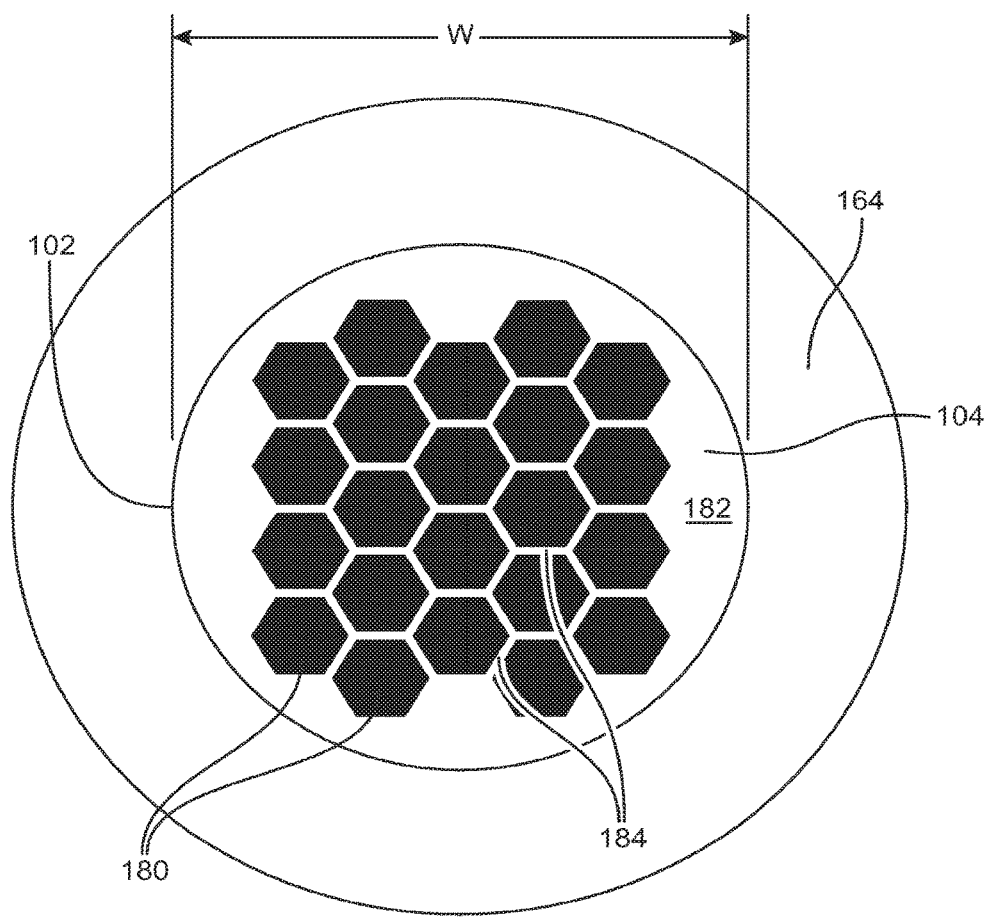
FIG. 11 is a plan view of the transcranial channel of FIG. 10.

Referring now to FIGS. 10 and 11, a variation of a channel 100 is shown having an overall width, w, that is much greater than its length, l, and a plurality of inner lumens 180 defined in the interior cavity 104. The length l of the channel 100 may be selected to approximate the thickness of the skull, so that when the channel is in position in the skull, the channel will traverse the entire thickness of the skull. Alternatively, the channel may be designed to traverse almost, but not all, of the thickness of the skull to avoid breaching the inner layer 40 of the skull. When a channel of this greater overall width is indicated, providing the plurality of inner lumens will enhance the mechanical stability of the channel. The plurality of inner lumens will also provide a mechanical barrier in what would otherwise be a relatively large open space between the outer and inner layers of the skull, and thus may prevent inadvertent breaches of that space with undesired objects (e.g., a finger or instrument during implant or during an application such as delivery of neuromodulation).

Figure 12:
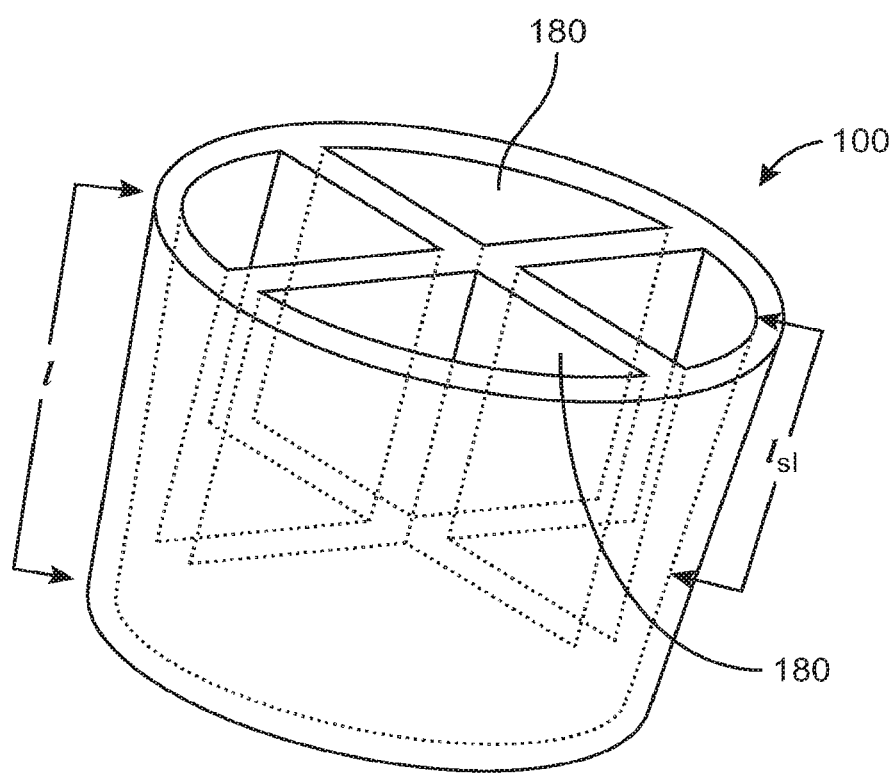
FIG. 12 is a perspective view of a variation of a transcranial channel having a plurality of inner lumens.

The length, $l_{sl}$, of the each of the inner lumens 180 may be the same as or approximate the length, l, of the channel 100. In FIG. 12, each lumen lengths, $l_{sl}$, is approximately the same as every other lumen length, $l_{sl}$, and the lumen lengths are less than the length, l, of the channel. Optionally, one or more of the inner lumens 180 may have different lengths, $l_{sl}$, and one or more of the lengths, $l_{sl}$, may be less than the length, l, of the channel 100.

Each of the inner lumens 180 is characterized by a cross-section that is generally hexagonally shaped, but many other shapes useful for particular applications of the channel 100 will be apparent to those skilled in the art. The inner lumens 180 may be formed as sub-lumens in the interior cavity from a single starting piece, e.g., with a mold or molding process. In this case, the portion 182 of the interior cavity 104 between the walls 184 of the plurality of inner lumens 180 and the outer wall 102 may be filled in, i.e., formed from a solid or semi-solid piece of material, such as the same material that is used for the outer wall 102, and may be an extension of the outer wall 102. In another variation (not shown in FIG. 10 or 11), each inner lumen 180 may be individually formed and inserted into the interior cavity 104. In this case, the portion 182 of the interior cavity 104 between the walls 184 of the plurality of inner lumens 180 and the outer wall 102 may be left as a part of the interior cavity 104, i.e., left open to the air (to be later filled or partially filled with serum, among other things, when the channel 100 is positioned in the skull).

The outer wall 102 may be formed from a substance that is non-ion permeable or that contains non-ion permeable material, e.g., to minimize the loss of current from the channel to the trabecular bone (middle layer) of the skull when the channel is used to conduct current. Alternatively, one or more surfaces of the outer wall 102 may be provided with a coating containing a non-ion permeable material for the same purpose.

The channel 100 with the plurality of inner lumens 180 of FIG. 10 is provided with an optional lip 164 to assist in maintaining the channel at the desired position in the skull and to prevent the channel from inadvertently being pushed further in towards the brain than desired. One or more screw holes (not shown) may be provided in the lip so that the channel may be secured with one or more screws to the skull once the channel is positioned at the desired location.

Figure 13:
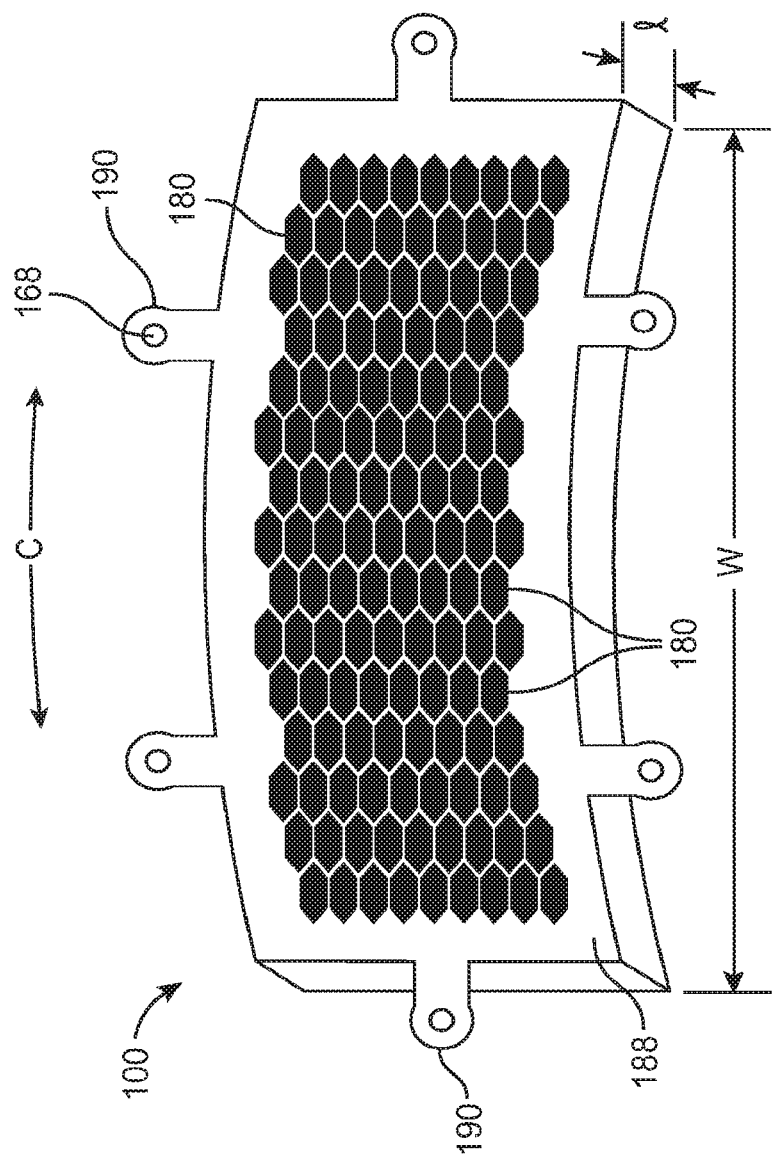
FIG. 13 is a perspective view of a variation of a transcranial channel.

FIG. 13 illustrates another variation of a transcranial channel 100 having a plurality of inner lumens 180. In this variation, the channel 100 is formed from a single piece 188 of starting material, e.g., by an injection molding process. The inner lumen lengths, $l_{sl}$, may be different than the overall length, l, of the channel 100, e.g., $l_{sl}$, may be greater or less than l for a given inner lumen 180.

The channel 100 of FIG. 13 does not have a lip that is designed to extend over or rest on the outer surface of the skull when the channel is positioned transcranially. However, the channel 100 of FIG. 13 is provided with tabs 190 that are formed as a part of the piece of starting material 188 and which extend outwardly from the top surface of the channel. Each tab 190 is provided with a screw hole 168 through which a screw may be inserted at the time the channel is deployed in the skull to help anchor the channel at the desired location. Alternatively, the tabs 190 may be formed of a material different from that of the starting material 188 and more suitable for mechanically anchoring the channel 100 in the skull; for example, titanium tabs 190 used to anchor a polyetheretherketone starting material 188.

In another variation, the tabs 190 may be replaced or augmented by a substantially continuous lip 164 (not shown in FIG. 13).

The channel 100 shown in FIG. 13 has an overall width, w, that is much greater than its length, l, and the length, l, is chosen so as to approximate all or most of the thickness of the skull. Therefore, the channel 100 is intended to extend over a fairly significant portion of the patient's skull. Accordingly, the variation of the channel 100 in FIG. 13 is provided with a curvature, c, that is intended to approximate the natural curvature of the patient's skull where the channel is to be located when in use.

Figure 14:
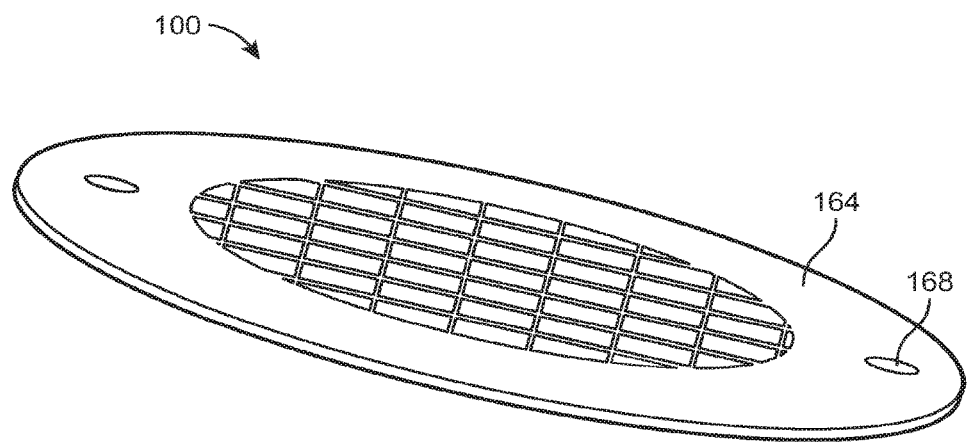
FIG. 14 is a perspective view of another variation of a transcranial channel.

Referring now to FIGS. 14 and 15, still another variation of a channel 100 is illustrated that has an overall width, w, that is much greater than its length, l. Moreover, the length, l, of the channel 100 is also much less than the thickness of the skull Thus, this variation is characterized by a short interior cavity 104. This channel is designed to fit into or over the proximal end of the aperture formed to accept it (i.e., the end of the aperture at the outer surface of the skull) in the manner of a lid, with the channel length, l, intended to extend slightly above the surface of the skull rather than to traverse any significant portion of the thickness of the skull. The channel 100 shown in FIG. 14 is shown with an optional rim or lip 164 and screw holes 168 that may be used to help secure the channel 100 to the outer surface of the skull. The channel 100 shown in FIG. 14 is further optionally provided with a mesh-like structure 191 formed in the interior cavity 104. This mesh-like structure 191 may provide mechanical stability to the channel and may prevent inadvertent breaches of the skull aperture space with undesired objects (e.g., a finger or instrument during implant or during an application such as delivery of neuromodulation).

FIG. 15 schematically illustrates a method by which the channel 100 of FIG. 14 may be deployed. First, an aperture 192 is formed over a target area 24 of the brain (e.g., a target for neuromodulation and/or for sensing parameter from the brain). The size of the aperture will approximate the overall width, w, of the channel 100 that is intended to sit in or over the aperture. The channel 100 is then inserted into the aperture and, if screw holes 168 are provided in a lip 164, the channel 100 may be secured to the outer surface of the skull 36 with screws (not shown).

Variations of the channel 100 illustrated in the Figures show channels with a gross shape that is generally circular or rectangular in plan view. However, it will be appreciated by those skilled in the art that multiple other shapes may be provided to best suit the intended application of the channel. Fundamentally, considerations of mechanical stability for the deployed channel may inform the overall size and shape of the channel, as well as the number and configuration of any inner lumens that are provided. In addition, the overall size, shape and number of inner lumens provided, if any, may be driven by the intended application(s) for the channel and the target area(s) of the brain associated with those applications. For example, a single channel may be designed to provide a skull/brain interface for multiple applications using multiple target areas of the brain. In this case, the overall shape of the channel in plan view may be tailored for the application and/or for the target area, e.g., to match the overall dimensions of each target area. Similarly, if a channel is provided with a plurality of inner lumens, the size and shape of the cross-sections of these inner lumens may vary within a given channel to suit multiple applications for the channel (e.g., delivery of neuromodulation and measurement of EEG) and/or to accommodate the different dimensions of different target areas of the brain.

Figure 16A:
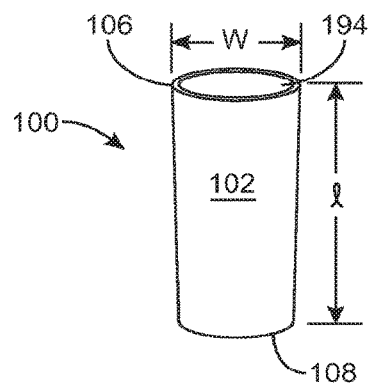
FIG. 16A is a front view of a variation of a transcranial channel.
Figure 16B:
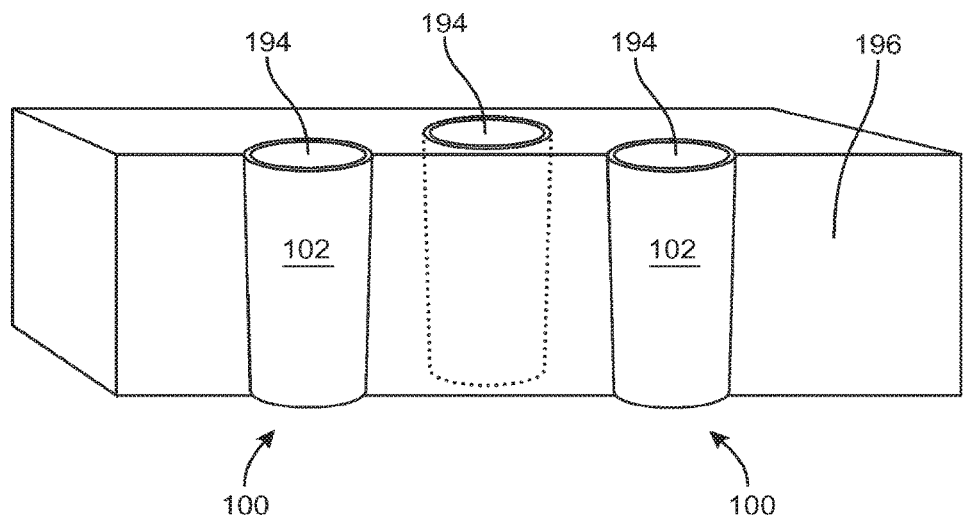
FIG. 16B is a schematic view of a plurality of the transcranial channels shown in FIG. 16A.

FIGS. 16A-16B and FIGS. 17A-17C illustrate still other variations of a transcranial channel 100. FIGS. 16A and 16B depict a channel 100 having an overall width, w, that is much less than its length, l. Since the channel length, l, is designed to approximate the entire thickness or substantially the entire thickness of the skull of the patient in whom the channel is to be implanted transcranially, the channel of FIGS. 16A and 16B is generally small or fine and cannula-like. In one variation, the cross sectional diameter of the generally cylindrical cannula-like channel 100 is on the order of 1 to 2 mm, as compared with a typical skull thickness on the order of 5 mm. The channel may be formed from a biocompatible polymer to resemble a thin-walled straw.

The channel 100 may be provided in the form of a solid or semi-solid plug of material as described with respect to FIG. 7, optionally characterized by a taper from the proximal to the distal end. Alternatively, and as shown in FIGS. 16A and 16B, the channel 100 may be provided with an outer wall 102 that defines an interior cavity or small bore 194. The small bore 194 may extend all the way through the channel 100 so that it is contiguous with the outer wall 102 and open to the air (or, when implanted, to the intracranial space) at the distal end 108 of the channel. Optionally, the small bore 194 may be provided with one or more end caps (not shown), for example, in the form of a thin membrane of material, in order to retain a substance that may be provided in the small bore 194, e.g., an ion-permeable substance or a pharmaceutical substance.

The channel 100 shown in FIGS. 16A and 16B has a generally circular cross section, but it will be appreciated by those skilled in the art that the channel may be provided with cross sections of other shapes, such as square, oval, rectangular, hexagonal, etc. The cross-sectional shape may be a design consideration with respect to one or more of the following: the mechanical stability of the channel during or after implantation, the ease with which the channel may be manipulated during implantation, and the efficiency with which the channel can conduct through the skull to the target areas of the brain.

One or a plurality of these small bore channels 100 may be used with a given patient, depending on the desired application for the skull/brain interface provided by the channel(s). If a plurality of the small bore channels are used, the channels may be grouped together, as schematically represented in FIG. 16B (with the shaded area 196 representing the skull). Alternatively, relatively many small-bore channels 100 may be used to cover different target areas of the brain.

Figure 17A:
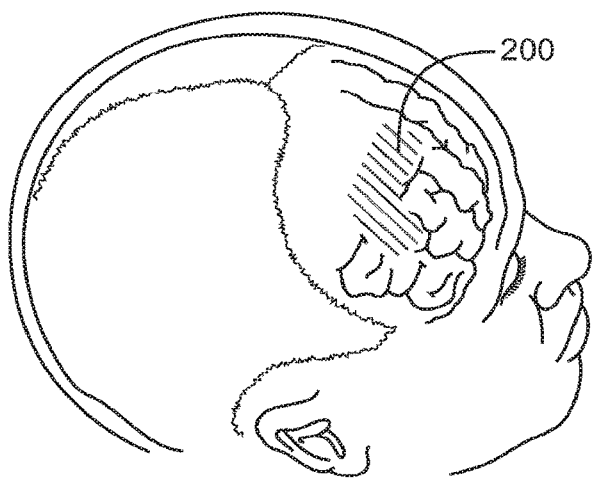
FIG. 17A is a schematic view depicting an area of interest in a patient's brain.
Figure 17B:
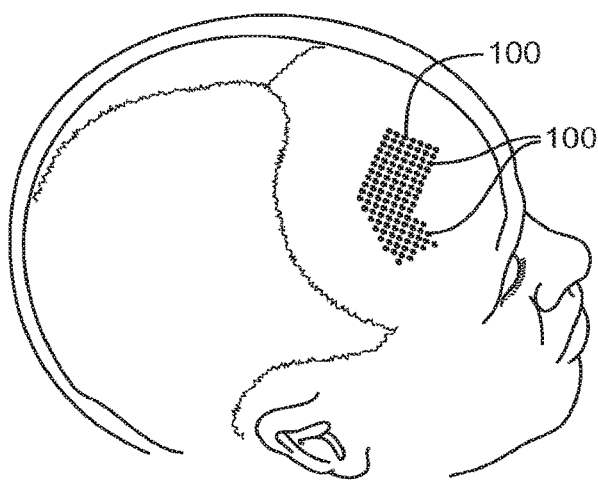
FIG. 17B is a schematic view depicting one configuration for deployment of the transcranial channels of FIGS. 16A and 16B.
Figure 17C:
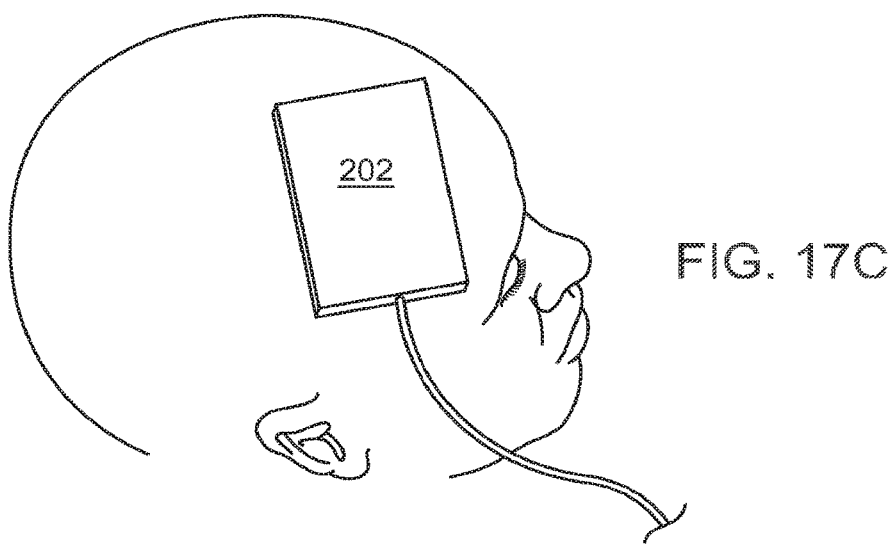
FIG. 17C is a schematic view depicting a device positionable over the configuration of transcranial channels of FIG. 16B.

For example, FIGS. 17A-17C illustrate one possible deployment of small-bore channels 100 to cover a fairly large area of the underlying brain, depicted by the shaded area 200 in FIG. 17A. This area may represent multiple target areas 24 for one or more applications of the interface (e.g., delivery of neuromodulation to the brain, heat transfer from the brain exteriorly of the skull, measurement of an EEG, etc.). FIG. 17B shows a plurality of small-bore channels 100 implanted transcranially over the shaded area 200. (One method for implanting the small-bore channels is described hereinbelow.)

FIG. 17C shows a device 202 that is positionable over the plurality of implanted small-bore channels 100, which device may be capable of facilitating one or more of delivering a source of neuromodulation to a target area of the brain, removing heat from a target area of the brain, or sensing a parameter through the interface that is believed or understood to be characteristic of a brain state.

In still other variations, transcranial channels 100 may be designed for the purpose of conducting heat away from a target area 24 of the brain via thermal conduction (i.e., as opposed to, for example, conducting electric current via ion movement). One application of one or more of these channels may be to draw heat away from an epileptic focus in the brain with the goal of stopping or avoiding seizures. Channels designed for this purpose may be used alone or in conjunction with one or more devices applied external to the scalp to help draw the heat away from the brain and/or to act as a reservoir for the heat as it is removed.

Figure 18A:
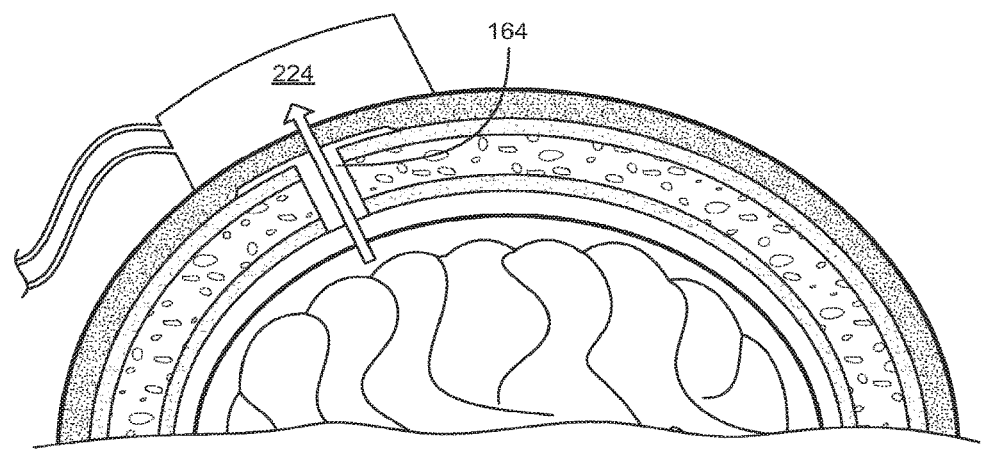
FIG. 18A is a side, cross-sectional, schematic view illustrating a system for removing heat through a skull/brain interface.

FIGS. 18A and 18B illustrate a transcranial channel 100 designed for the purpose of providing a skull/brain interface through which heat can be withdrawn from the interior of the skull. The channel 100 is formed substantially from a material characterized by a high thermal conductivity 220, for example, in the range of 300 to 500 Watts per meter-Kelvin, such as copper or silver. The channel may be provided with one or more rods formed from the high thermal conductivity material 220.

For biocompatibility, it may be necessary to dispose a layer or coating 222 of a biocompatible material over or substantially over the material with high thermal conductivity. Such a layer or coating may be constructed of a biocompatible material with low thermal conductivity, for example titanium, since the channel 100 is formed substantially from a material characterized by a high thermal conductivity 220.

Optionally, the channel 100 may be provided with a rim or lip 164 to increase mechanical stability in the skull and to increase the extracranial area of the device and, thus, the area available for heat conduction to the scalp. It will be appreciated by those skilled in the art that a channel 100 constructed as described here to facilitate transfer of heat may also facilitate conduction of electrical current in the form of ion movement, if one or several ion-permeable lumens is provided within the material characterized by a high thermal conductivity 220.

Although a single channel 100 is shown in FIG. 18A, it will be appreciated by those with skill in the art that a plurality of channels may be useful for particular applications intended for heat transfer. Similarly, certain applications may benefit from channels characterized by a relatively large overall diameter, as shown in FIG. 11 and FIG. 13, with or without a plurality of inner lumens, or from the cannula-like channels shown in FIGS. 16A-16B and FIG. 17B.

Other variations of a transcranial channel for use in drawing heat away from the brain may be based on the principle of operation of a heat pipe commonly used for cooling electronic devices. Heat pipes may be configured in a number of ways, but typically are hollow metal tubes containing a working fluid. In one such variation of a transcranial channel, a heat pipe could be provided in the form of a hollow metal tube capped at the proximal and distal ends thereof, designed to extend through the thickness of the skull with the distal end of the tube intended to be oriented near a target area of the brain from which heat is to be removed, and the proximal end of the tube intended to be positioned towards the outer skull or scalp. A wicking substance or structure such as a nonsoluble fibrous material, sintered metal powder, or series of grooves oriented in the distal-proximal axis may be situated within this chamber or on its interior walls to further facilitate heat pipe action. A working fluid could be provided within the hollow tube such as water, the water being maintained at a pressure suitable to maintain the majority of the water in the pipe as water vapor until a receptacle for the heat to be transferred from the brain is brought into proximity of the proximal end of the channel. When the receptacle is present, the water vapor in the heat pipe near the cooling device condenses, transferring heat to the cooling device, and the additional water in the heat pipe near the brain evaporates, removing heat from the brain. As long as there exists a temperature differential between the brain and the receptacle or external heat reservoir, the transcranial channel provided with the heat pipe can operate continuously to cool the brain.

Figure 19:
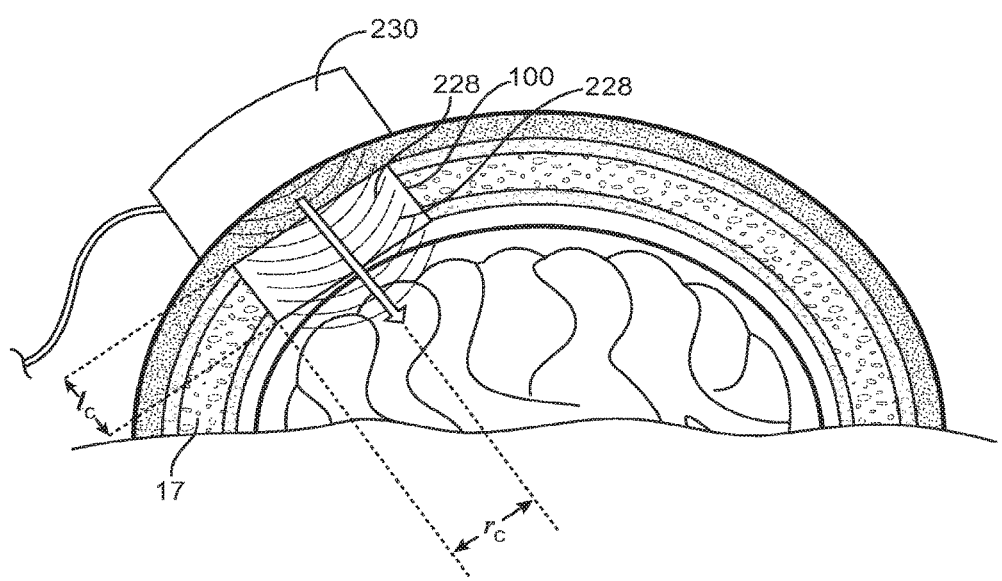
FIG. 19 is a side, cross-sectional, schematic view illustrating a system for delivering energy through a skull/brain interface.
Figure 20:
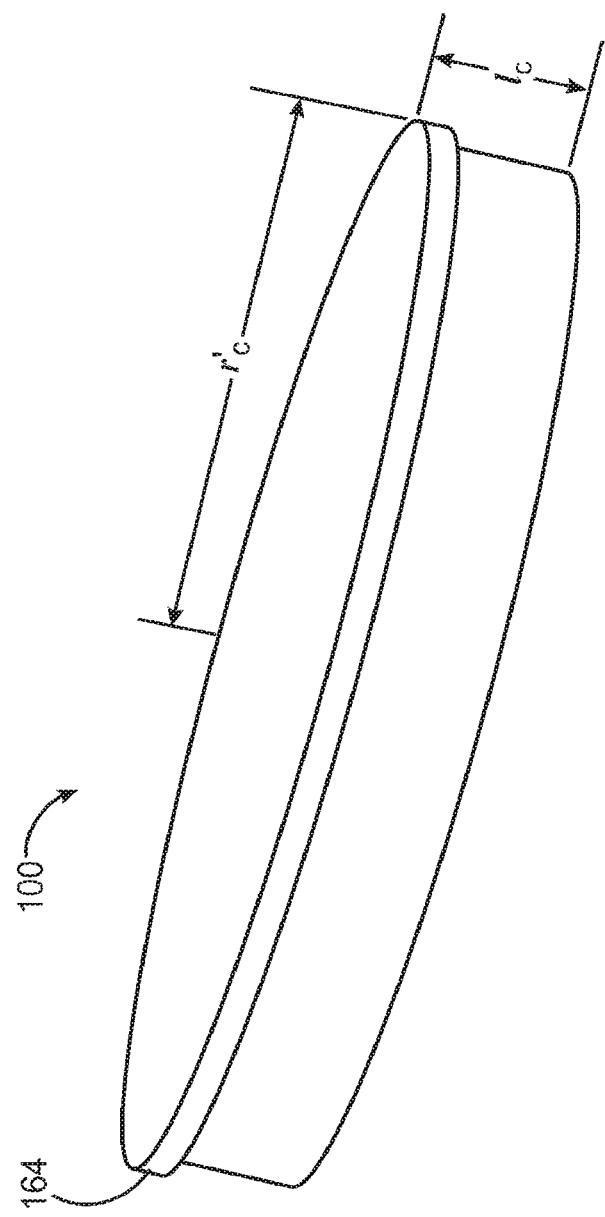
FIG. 20 is a perspective view of the transcranial channel depicted in FIG. 17C.

In still other variations, transcranial channels may be designed to facilitate the delivery of energy to the brain, for example, in a high intensity focused ultrasound ("HIFU") application wherein ultrasound is used to ablate brain tissue or create lesions in the brain. Referring now to FIGS. 19 and 20, a transcranial channel 100 is formed from a material that is understood to be largely transparent to ultrasound (e.g., an acrylic material). The dimensions of the channel 100 are characterized by a substantially constant radius, $r_c$, and a substantially constant length, $l_c$, to facilitate passing the ultrasound signals 228 from an ultrasound source 230 through the skull/brain interface with minimal distortion, thus allowing for relatively precise and accurate focusing of the ultrasound onto the target area(s) 24 for one or more procedures (e.g., to surgical ablation of brain tissue or one or more ultrasound procedures to create precise lesions in the brain without requiring additional, more invasive surgery). The channel 100 may be provided with a lip 164 to minimize the risk of inserting the channel further into the skull than intended during or after the channel is implanted.

Any transcranial channel or plurality of transcranial channels described herein can be associated with an element or elements for closing off the channel(s), temporarily or permanently. An element may be in the form of a stopper with dimensions designed to fit in the part or parts of the channel that otherwise would be open to conduction.

If the channel is filled or partially filled with a substance other than air, the element could be a shield that covers the conducting portions of the channel to discourage conduction. A shield and a skull/brain interface may each be provided with features that are designed to mate the shield with the skull/brain interface when the shield is deployed, such as a fitting in the shield that is designed to be inserted into a socket provided on a channel or vice versa.

The elements for closing off the channels may be designed to be temporary (for example, so that they can be removed while DC stimulation is being delivered and then replaced) or permanent (for example, so that they can be used when the channels are to be permanently disabled such as when a treatment plan has been completed).

Figure 21:
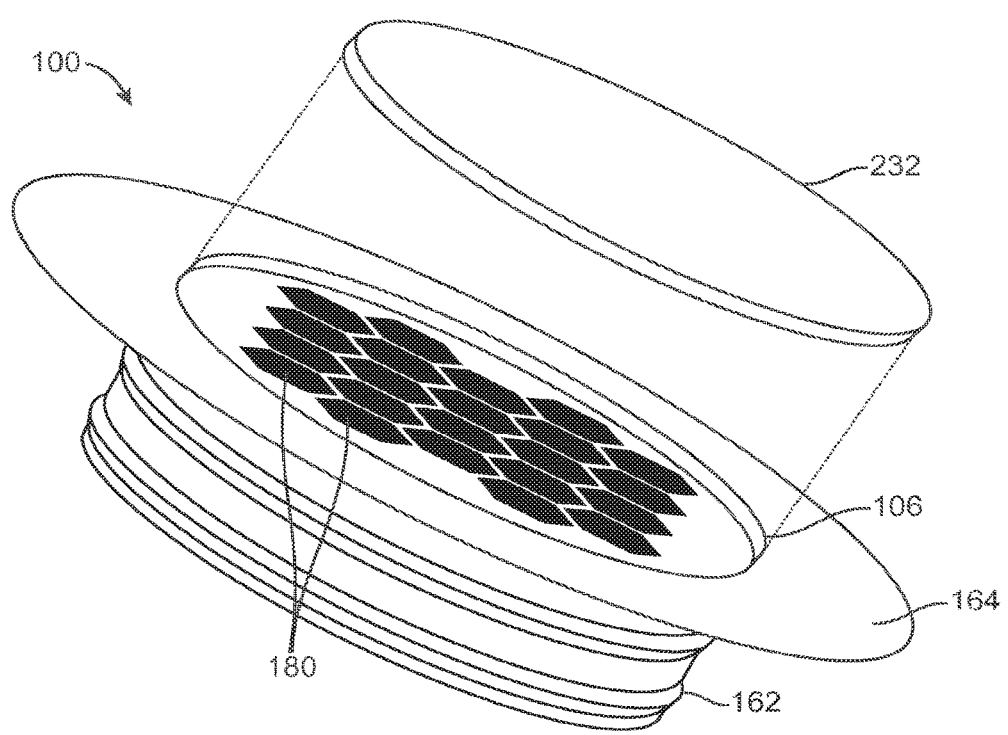
FIG. 21 is a perspective view of a transcranial channel and a shield for closing off the channel.

The element or elements for closing off a channel or a plurality of channels may be affixed via minor surgery which may or may not involve resecting the scalp in the area of the channel in order to install the element(s), and then replacing the scalp over the area. FIG. 21 illustrates a shield 232 that may be used to close off a transcranial channel 100 having a plurality of inner lumens 180. When the shield 232 is fitted over the proximal end 106 of the channel, conduction through the channel (for example, ion conduction) may be prevented either temporarily or permanently if the shield is formed from a material that is generally impermeable to ions (e.g., metal). While devices and methods for temporarily or permanently closing off channels have been described above, it will be apparent to one skilled in the art that the same or similar devices and methods may be used to temporarily or permanently close off apertures or preexisting or naturally-occurring fenestrations used or intended for use in facilitating focused neuromodulation or sensing of physiological signals from the brain or any methods disclosed herein (e.g., iontophoresis).

Figure 22A:
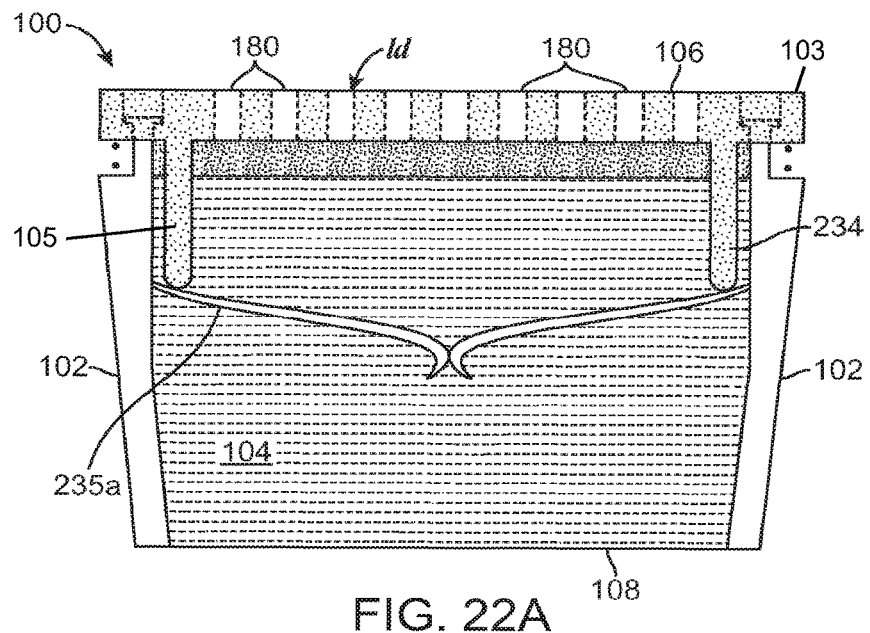
FIG. 22A is a cross-sectional of a variation of a transcranial channel in which a two-way valve is provided showing the valve in a closed position.
Figure 22B:
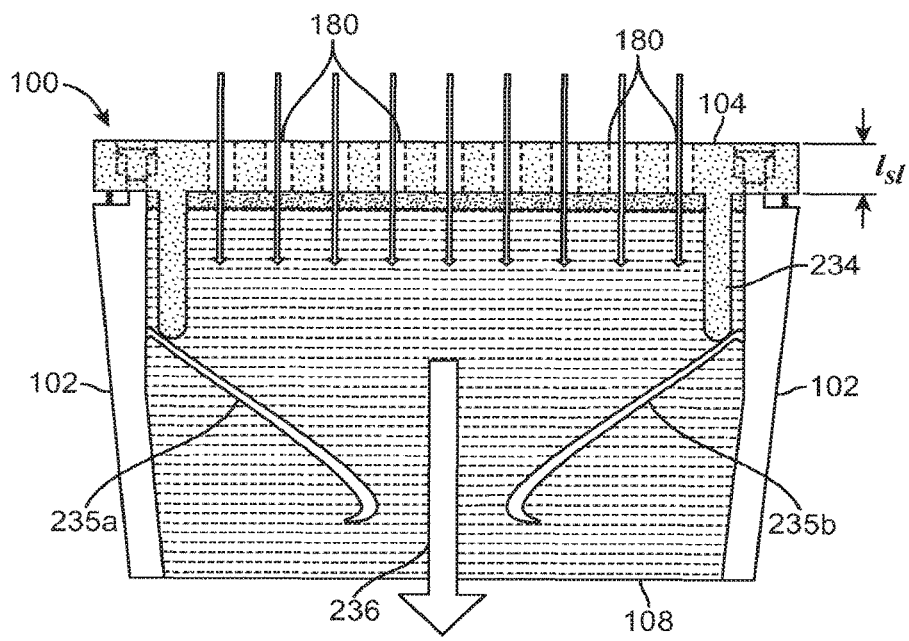
FIG. 22B is a cross-sectional and schematic view of the transcranial channel of FIG. 22A showing the direction of conduction when the valve is an open or partially open position.

In still other variations, any transcranial channel or plurality of transcranial channels described herein can be provided with a valve or valves to selectively allow the channel(s) to conduct. For example, and referring now to FIGS. 22A and 22B, a transcranial channel 100 having an outer wall 102 defining an interior cavity 104. The channel 100 is shown provided with a plurality of inner lumens 180 each having a length $l_{sl}$. A bicuspid valve 234 is shown with a first flap 235a and a second flap 235b. In FIG. 22A, the valve 234 is in a closed position and the first and second flaps 235a and 235b form a surface which discourages conduction through the channel in the direction from the proximal end 106 to the distal end 108. In FIG. 22B, the valve 234 is shown in an open or partially open position, with the first and second flaps 235a and 235b each displaced from their closed positions to allow conduction through the channel in the direction of arrow 236 (i.e., in the direction from the proximal end 106 to the distal end 108). The plurality of lumens 180 are included in a proximal end structure 103. The proximal end structure 103 includes at least one extension 105 that extends into the interior cavity 104 of the channel 100 toward the distal end 108 of the channel. The proximal end structure 103 is coupled to the outer wall 102 in a manner that provides for displacement of the proximal end structure relative to the outer wall, as evident from FIGS. 22A and 22B.

The valve 234 can be configured to transition from a closed position to an open or partially-open position by mechanical means, such as a pressure sensitive mechanism that cause the valve to open or close when pressure is applied to the valve, for example at a proximal surface thereof. Alternatively, the valve 234 can be configured to open and close by magnetic means (e.g., when a magnet is placed near the valve, the valve closes or opens). The valve may be configured to operate with other means, such as electrically, as will be apparent to those with skill in the art.

Similarly, and although a bicuspid valve is illustrated in FIGS. 22A and 22B, valvular action may be implemented in a channel 100 with any one of a number of different types of valves, singularly or plurally.

A combination of a channel or channels 100 and a valve or valves 234 may be configured so that the valve(s) 234 open or partially open selectively, for example, only when a stimulus is present for a certain period of time. The combination may also be configured together with a feature or features in the channel, the valve and/or in any external equipment with which the channel is intended to be used, so that the valve can only open when certain external equipment is recognized or positioned closely enough to the channel to be safe or effective. Alternatively or additionally, the combination could be configured with features in one or all of the elements so that the valve will close if, for example, external equipment is removed or taken out of a predetermined range, or certain limits for stimulation or exposure times are exceeded.

In some variations, a combination including a valved transcranial channel may be provided with a current or voltage detector. A current detector may direct the soft flaps 235a and 235b to close or remain closed when the amount of current being provided from a source (e.g., a source of neuromodulation coming from external equipment or from a source associated with such equipment) surpasses a threshold to, for example, prevent excessive stimulation from passing through the channel 100. In other variations, a combination including a valved transcranial channel may be provided with an active channel device (i.e., a channel device equipped with active electronics and having or associated with a power source) that is capable of sensing voltages, for example, at the inner and outer tables of the skull or between at least two points along the length of the channel 100. These voltages may be used to compute the amount of current in the channel 100 at any particular or predetermined time.

The valve feature also may be used beneficially in conjunction with the RFID capability described below.

In another variation, any of the transcranial channels 100 described with reference to FIGS. 6-16 may be provided with an RFID (Radio Frequency Identification) capability, to provide a reference that will aid in the positioning of other equipment that is to be used with the transcranial channel, such as an external stimulation or recording device. For example, and with reference to FIGS. 23A and 23B, a channel 100 is provided with first and second passive RFID controllers 240 and 242. The passive RFID controllers 240 and 242 may be embedded in the piece 188 from which the channel is formed or may otherwise be affixed or attached to the channel 100. First and second receiver antennas 244 and 246 are provided disposed about or near the first and second passive RFID controllers 240 and 242, respectively.

RFID features can also be used to good effect with transcranial channels to prevent a particular channel from being used with other than authorized external equipment and devices, such as stimulation devices and equipment to measure and/or store signals sensed through the channel. For example, one RFID element in a channel can be associated with another RFID element in the external equipment such that only that equipment can be used for that channel in that patient.

The RFID element(s) can be used to identify particular patients to the external equipment or to any other device or system, such as a device or system designed to identify which patients have skull/brain interfaces, or which skull/brain interfaces are in which patients, or which skull/brain interfaces are permissible for use with certain neuromodulation sources or sensing equipment, etc. Similarly, the RFID elements can be used to control permissible dosages of stimulation or drugs, especially when delivery of the stimulation or drugs is wholly or partially under the control of the patient (e.g., the RFID elements might be configured to prevent the patient from delivering more than a prescribed amount of stimulation to himself or herself per day).

Figure 23A:
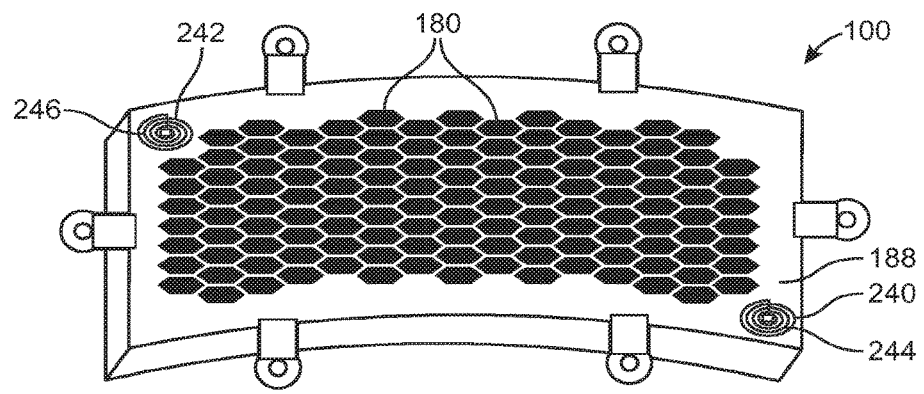
FIG. 23A is a perspective view of a transcranial channel having RFID capability.
Figure 23B:
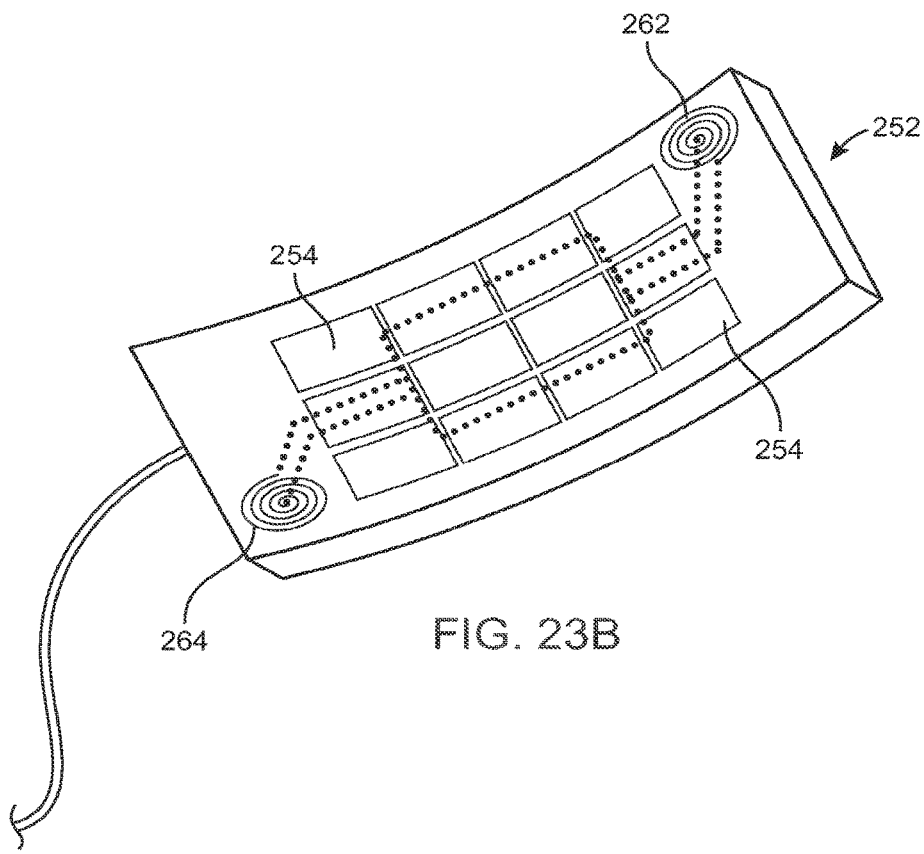
FIG. 23B is a perspective view of a measuring device having RFID capability complementary to the transcranial channel of FIG. 23A.

Referring now to FIG. 23B, the RFID capability in the channel 100 of FIG. 23A may be complimented with a device 252 associated with the application for which the skull/brain interface is being accomplished (e.g., delivering neuromodulation to the brain and/or sensing parameters from the brain). The device 252 shown in FIG. 23B is provided with EEG electrodes 254 that can be used in acquiring an EEG. The device 252 is provided with an active RFID controller 256. The device 252 is further provided with a first transmitter antenna coil 262 located so that it is positionable over the first receiver antenna 244 in the channel 100 and a second transmitter antenna coil 264 located so that it is positionable over the second receiver antenna 246 in the channel. The RFID capability is likely to be especially useful when the same channel 100 is being used for multiple applications (e.g., for delivering neuromodulation and sensing), for example, by providing information about the relative positions of the neuromodulation source and the channel or the inner lumens 180 provided in the channel and/or about the relative positions of the channel and/or inner lumens and EEG electrodes.

Figure 24:
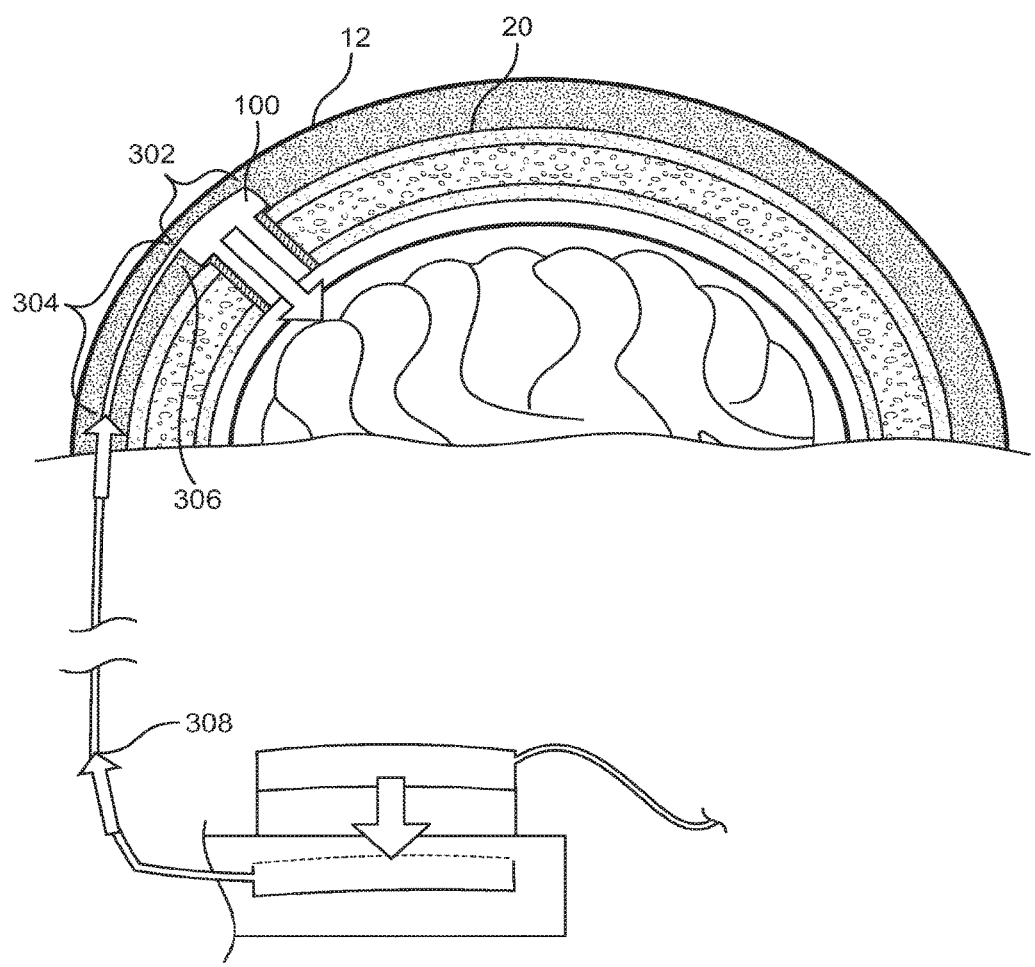
FIG. 24 is a side, cross-sectional, schematic view illustrating a system for extending a transcranial channel.

Another variation of a transcranial channel is shown in FIG. 24, where the channel 100 is provided with an extracranial extension 300. In FIG. 24, the extracranial extension 300 is associated with one transcranial channel 100, although it will be apparent to those skilled in the art that more channels may be used with the extension. The extension 300 has a first portion 302 having dimensions designed to substantially cover and/or partially overlap the area of the skull 20 in which the channels 100 are positioned and to lie between the scalp 12 and the skull 20. The extension has a second portion 304 with a first end 306 and a second end 308. The first end 306 of the second portion 304 may be connected to the first portion 302 of the extension and effectively continues the channel extracranially (e.g., if the channel is being used for conduction of current by ion conduction, the first portion 302 may have an inner lumen filled with saline solution or fillable with an ion-permeable substance). The second end 308 of the second portion 304 may be routed percutaneously or subcutaneously to another location in the body, e.g., another location on the head or a location on the neck or shoulder.

The extracranial extension 300 thus permits the source of neuromodulation, or the equipment for obtaining a measurement, to be placed near the second end 308 of the second portion 304 of the extension rather than in the vicinity of the channel(s) 100, adding to the flexibility of the skull/brain interface. The extension also may increase the cosmesis or aesthetics of the particular application of the channel(s) from the perspective of the patient and therefore may make the application(s) more popular with patients.

Figure 25A:
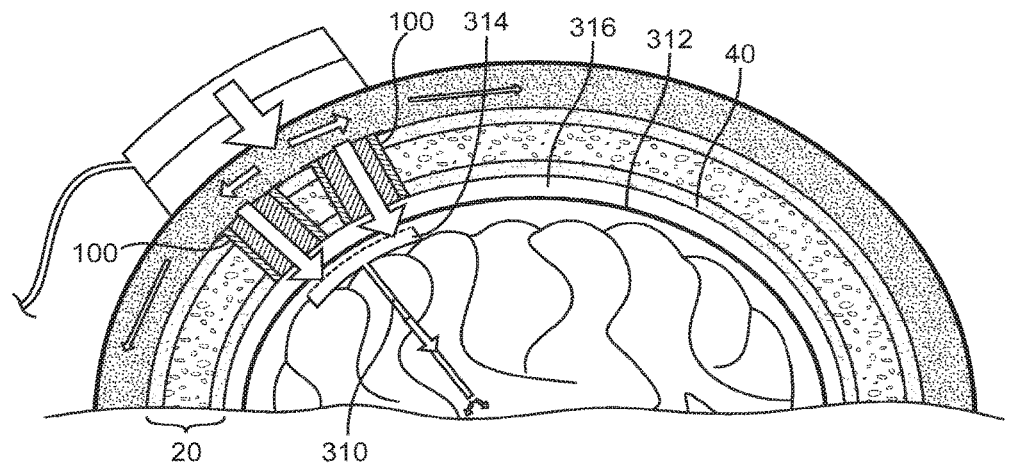
FIG. 25A is a side, cross-sectional, schematic view illustrating a system for using one or more transcranial channels with a transparenchymal channel.
Figure 25B:
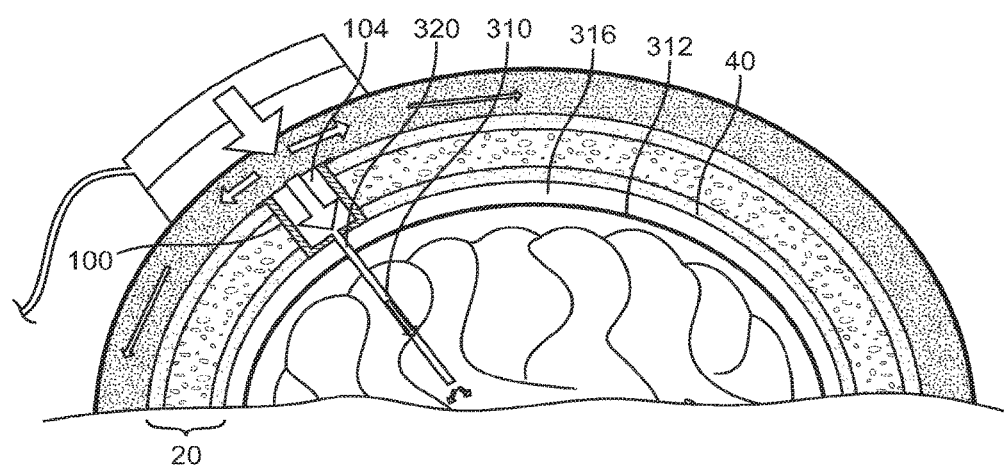
FIG. 25B is a side, cross-sectional, schematic view illustrating a variation of the system shown in FIG. 25A.

In still other variations, and with reference now to FIGS. 25A and 25B, one or more transcranial channels 100 may be provided for direct current neuromodulation (e.g., polarization or stimulation) in combination with one or more deep brain or transparenchymal channels 310 (only a single transparenchymal channel is shown in FIGS. 25A and 25B).

The transparenchymal channel 310 may be formed from a soft material such as silicone and provided with an inner lumen 320. One or more stiffening elements (not shown), such as a coil formed from metallic or non-metallic materials, may be provided in or around the transparenchymal channel inner lumen 320 to help maintain the patency of the lumen without comprising to any great extent the flexibility or "floppiness" of the transparenchymal channel. Alternatively, a thin coil of wire may be embedded in the transparenchymal channel 310 to encourage each structure to remain patent and in the desired shape. The transparenchymal channel inner lumen 320 may be fillable with saline solution or another ion-permeable substance.

In another variation, at least the side of the transparenchymal channel 310 that is intended to contact the brain may be formed substantially from a soft, flexible ion-permeable material. This variation of a transparenchymal channel 310 may be designed for insertion into a brain sulcus.

In still another variation, a combination of a transcranial channel 100 and a transparenchymal channel 310 may be provided as a single unit, characterized entirely by ion-permeability or having a contiguous interior cavity that is ion-permeable or fillable with an ion-permeable substance. The dimensions of the combination of this variation should be sufficient to allow sufficient slack, after implant, between the proximal end 106 of the transcranial channel 100 at the skull and the transparenchymal channel 310 in the brain parenchyma or resting in a sulcus of the brain, to accommodate movement of the brain inside the skull.

The transparenchymal channel(s) 310 may be used to deliver DC stimulation to target structures in the interior of the brain while avoiding the potential complications that would otherwise be presented by the electrode-to-tissue interface if a conventional deep brain electrode were used. A transparenchymal channel 310 may be implanted into the brain using techniques similar to those used by those skilled in the art to implant conventional deep brain electrodes for pulsatile electrical stimulation. Alternatively, in the case of the variation where the transparenchymal channel 310 is substantially ion-permeable on the side intended to contact the brain, the transparenchymal channel 310 may be inserted into a sulcus of the brain.

With reference to FIG. 25A, the transparenchymal channel 310 may be used in conjunction with the transcranial channels 100 to facilitate deep brain stimulation without requiring the transparenchymal channel to be coupled mechanically to the dura mater 312 or the skull 20.

A collector 314 is associated with the transparenchymal channel(s) 310 and designed to be implanted in the epidural space 316, i.e., between the inner layer 40 of the skull 20 and the dura mater 312 or, alternatively, completely under the dura mater 312.

The collector 314 may be formed from a soft material such as silicone and provided with an inner lumen 318. One or more stiffening elements (not shown), such as formed from metallic or non-metallic materials, may be provided in or around the collector inner lumen 318 to help maintain the patency of the lumen without comprising to any great extent the flexibility or "floppiness" of the collector. Alternatively, a thin coil of wire may be embedded in the collector 314 to encourage each structure to remain patent and in the desired shape. The collector 314 also may be fillable with saline solution or another ion-permeable substance.

A variation involving the combination of a transcranial channel 100 and a transparenchymal channel 310 without a collector for application of DC stimulation is illustrated in FIG. 25B. The transcranial channel 100 has an interior cavity 104 that is contiguous with the inner lumen 320 of the transparenchymal channel 310. In this variation, care should be taken when the transparenchymal channel is implanted to insure that there is enough slack in transparenchymal channel to guard against it moving, slicing, or pulling out of the brain as the brain shifts in the skull.

Deployment/Implantation of Transcranial Channels

Figure 26:
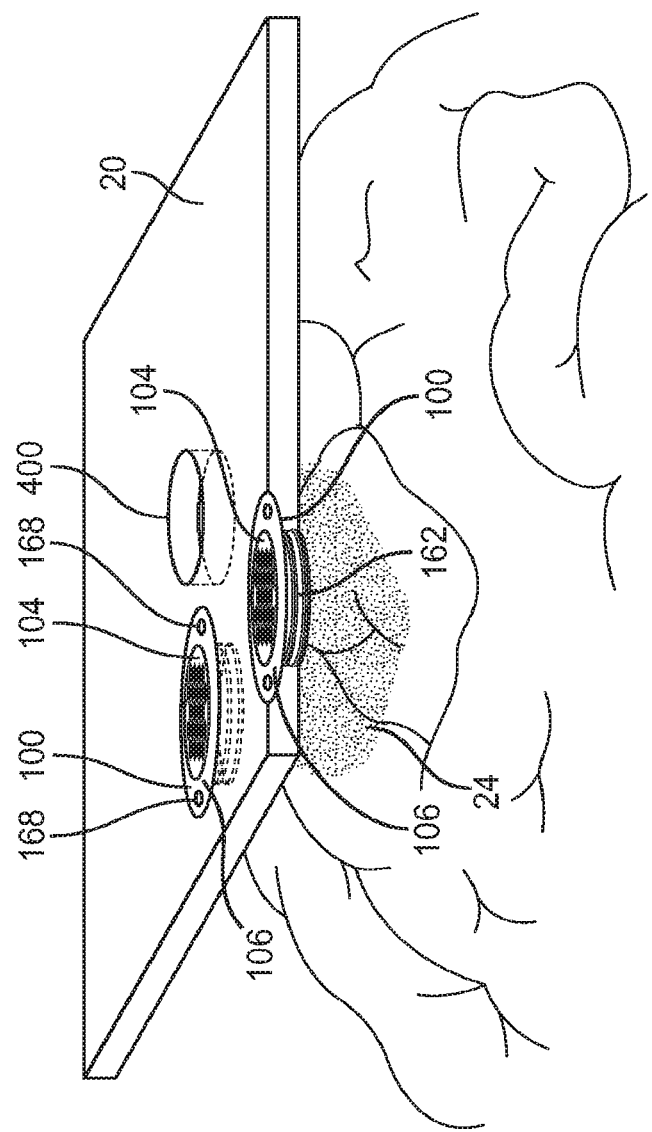
FIG. 26 is a schematic representation of one method of inserting a transcranial channel into the skull of a patient.

In one variation, and referring now to FIG. 26, a transcranial channel 100 may be implanted in a patient's skull by making an incision in the scalp 12 over or near the target region 24 of the brain to which neuromodulation is to be applied or from which a signal is to be acquired or heat is to be transferred. A craniotomy may be performed if the entire skull is to be breached by the channel(s) (e.g., formation of a burr hole 400) to remove a portion of the skull matching the dimensions of, or slightly greater than the dimensions of, the particular channel(s) to be implanted. If the transcranial channel is one that is intended to be used without entirely breaching the skull, a craniectomy may be performed to remove a portion of the skull sufficient to allow placement of the channel. The surgeon can insert the channel(s) 100 with gloved fingers or with an appropriate instrument such as a forceps.

If the channel 100 is provided with ridges 162, then the channel can be twisted or torqued while it is being inserted to help anchor the channel in the hole. Optionally, after the channel 100 is in the desired position, any open space between the skull 20 and the exterior of the channel 100 can be filled with a glue or cement to secure the channel and to minimize the possible routes for infection of the brain. PMMA or poly(methyl methylacrylate) is a common bone-compatible material that can be used for securing the channels 100. If the channel 100 is provided with additional means for affixing it to the skull, for example, screw holes 168, the channel 100 then is screwed into place in the skull 20.

After all the steps to position the channel or channels 100 are completed, if the channels 100 are intended to be put to use in an application immediately, the channels may be flushed or purged with saline. Optionally, the interior cavities 104 (or inner lumens 180 if provided) may be filled or partially filled with something: for example, a substance such as porous silicone, porous polyurethanes, or hydrogels; or porous masses constructed by sintering together particles of a nonporous polymer such polyurethanes, polytetrafluoroethlene, polyetheretherketones, polyesters, polyamides (e.g., nylon); or a sponge or sponge-like substance infiltrated with a nonproliferative agent such as bone morphogenic proteins, ciliary neurotrophic factor, ribavirin, sirolimus, mycophenolate, mofetil, azathioprine, paclitaxel, cyclophosphamide, or atomic silver to discourage cell proliferation and tissue growth into the channel.

The scalp 12 is then positioned over the channel proximal end(s) 106, and any incision is closed.

Next, the external equipment or devices necessary to carry out the intended application(s) for the channels 100 is brought in proximity to the location of the channels in the skull 20. (It will be appreciated by those with skill in the art that a given channel 100 may be used to provide a skull/brain interface for more than one application, for example, conducting a source of DC stimulation to a target area of the brain and conducting signals from the brain out to the exterior of the skull for measurement, as for an EEG.)

Deployment/Implantation of Cannula-Like Transcranial Channel(s) with Dilators

In another variation, a transcranial channel 100 having a length approximating the thickness of the skull and an overall width much less than the length, e.g., a small bore, cannula-like transcranial channel as described with reference to FIGS. 16A-17C, may be implanted in a patient's skull according to the following method. A very small opening (on the order of the diameter of a hypodermic needle) is made in the scalp. The opening may be formed with a drill, needle, or other appropriate instrument, and may terminate at the skull or may extend additionally all the way through the thickness of the skull or only part way through the thickness of the skull, e.g., through about 90% of the thickness of the skull. A dilator is inserted into the scalp opening to increase the size of the opening. If the scalp opening thus increased in size is large enough to accommodate the small bore transcranial channel, then the practitioner may next insert a retractor into the scalp opening to hold it open. A hole sufficiently large to accommodate the small bore transcranial channel may then be made in the skull with a drill or other appropriate instrument, or if a hole was previously made it may be enlarged to accommodate the channel. The practitioner may then insert the channel into the skull. The retractor and dilator are subsequently removed, leaving the channel in place in the skull. If deemed necessary or prudent, the proximal end of the channel may be trimmed to be flush with the exterior surface of the skull after insertion and/or after removal of the retractor and dilator.

The channel(s) may be flushed with saline and, optionally, the interior cavities thereof may be filled with a substance such as porous silicone, porous polyurethanes, saline solution, hydrogels, or porous masses constructed by sintering together particles of a nonporous polymer such polyurethanes, polytetrafluoroethlene, polyetheretherketones, polyesters, polyamides (e.g., nylon).

The wound may be closed by means such as tape or glue, avoiding the need for sutures and resulting in little or only moderate scarring. It is believed that this variation of a method for deploying small bore transcranial channels may be accomplished with minimal or local anesthesia and perhaps even with minimal disruption of the skin and scalp tissue overlaying the skull at the intended channel location, minimizing the complexity and invasiveness of the procedure.

After the channel(s) is/are inserted and the wound closed, the external equipment or devices necessary to carry out the intended application(s) for the channel(s) may be brought in proximity to the channels and the application(s) may be commenced.

In still other variations of a method for inserting a small bore transcranial channel into the skull, multiple dilators may be used, one after another, to gradually expand the pin prick scalp opening to a degree sufficient to accommodate the channel. The "METRX X-TUBE RETRACTION SYSTEM" available from Medtronic, Inc. is one system offering a series of increasing diameter dilators with which this method may be accomplished.

Identifying where to Locate a Skull/Brain Interface (Aperture or Channel) Targeting with Evoked Responses The skull/brain interfaces described herein, for example, the aperture interfaces and the channel interfaces, desirably improve the ability to focus neuromodulation (e.g., DC stimulation) in the brain better than is possible without the interfaces. Of course, it is important to put the interfaces where they will provide optimum focusing. One method for identifying the areas of the brain on which the skull/brain interfaces are to focus involves using some form of evoked response or evoked responses to localize or map out an area to be modulated (e.g., treated) or from which signals are to be sensed. The responses may be evoked from regions that are candidates for treatment or monitoring. Alternatively, responses may be evoked from regions that are believed to be somehow associated, directly or indirectly, with regions that are candidates for treatment or monitoring (for example, via neural circuits or pathways).

One method of obtaining the evoked responses uses transcranial magnetic stimulation (TMS). As described previously, TMS involves bringing the coil of a magnet near the head and energizing it by rapidly discharging a capacitor, which creates a rapidly-changing current in the coil windings. This rapidly-changing current sets up a magnetic field at a right angle to the plane of the coil. The magnetic field penetrates the skin and the skull to the brain and induces a current tangential to the skull. The current influences the activity of the neurons. TMS can be applied on a single-pulse or paired-pulse basis, or repetitively (rTMS).

TMS may be used to evaluate where to locate a skull/brain interface or interfaces by stimulating regions in an effort to evoke responses. The evoked response sought might be a muscle twitch in a specific muscle or other reaction in a specific anatomical location. For example, in a person with damage to the primary motor cortex caused by a stroke, TMS may evoke a weakened muscle twitch when applied to the one area as compared to a regular-strength muscle twitch in other areas. The attenuated muscle response in the one area may suggest that that area is the damaged area and therefore the area over which the skull/brain interface(s) should be located. Alternatively, a person who has suffered a stroke may exhibit a weakness in his left hand, which is controlled by the right side of the patient's brain. TMS may be used to try and identified the damaged or lesioned region on the right side of the brain. TMS may also be used to identify the corresponding undamaged region on the left side of the brain, which controls the right hand, so as to identify an area at which to introduce a skull/brain interface, based on the theory that stimulation therapy (e.g., inhibitory stimulation) delivered to the opposite, undamaged side of the brain might improve the patient's ability to control or strengthen his impaired hand. In still another example, a region of the brain that is believed to be associated with a certain neurological function, such as language processing or vision, may be identified by applying TMS at various locations on the skull and looking for a change in the neurological function, such as improved speech or vision or impaired speech or vision. One or more skull/brain interfaces subsequently may be provided at the areas so identified.

Other Aids for Locating Sites for Skull/Brain Interfaces Alternative to Traditional Stereotaxy Stereotaxy is commonly used in neurosurgery and neurological research to locate points within the brain using an external, three-dimensional frame of reference (usually based on the Cartesian coordinate system). It is typically a relatively elaborate process, especially when it involves mounting a frame on the patient and attaching the frame with one or more skull pins. It is most often relied upon when targets within the brain are to be precisely targeted as, for example, in placing electrodes on deep brain leads in or near particular brain structures, such as the subthalmic nucleus (STN).

While stereotaxy could be used to identify regions of the brain over which skull/brain interfaces are to be formed, less elaborate methods also may be sufficient under the particular circumstances. For example, an overlay that can be written upon or otherwise marked, such as a sticker or a sheet of plastic with temporary adhesive backing, can be laid over a section of the head to facilitate locating the site or sites at which skull/brain interfaces are to be provided. The overlay may have a feature that allows it to be oriented on the head with respect to some anatomical marker, such as the patient's ear. The overlay may include one or more pre-marked locations corresponding to possible sites for skull/brain interfaces, so that when the overlay is placed on the patient's head, the surgeon can choose from among several options for locations. Additionally or alternatively, the overlay may have space on which the surgeon can mark his or her own choice of sites for the interface(s).

Figure 27:
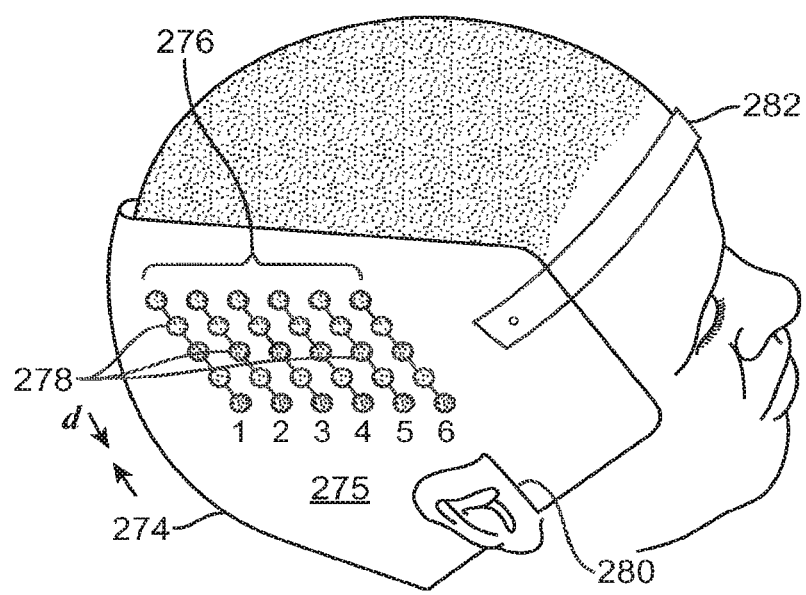
FIG. 27 is a schematic representation of a low-resolution stereotaxy assembly positioned on the head of a patient.

A form of a low-resolution stereotactic assembly may be provided alone or together with an overlay to aid in identifying the locations at which skull/brain interfaces are to be placed. Referring now to FIG. 27, a low-resolution stereotactic assembly 274 is shown provided with a body 275 having a skull/brain interface template 276 comprising a plurality of holes 278 formed in the body 275. The holes 278 are shown spaced apart from one another by a distance, d. Although in FIG. 27, the dimensions of the holes 278 and the distance, d, between the holes shown are uniform, it will be apparent to one with skill in the art that holes of different sizes and shapes might be provided, as well as holes with a variety of different sizes and shapes, and that the distances, d, between the holes also may vary.

The template 276 may formed integrally with the body 275 or provided as a separate component. If the low-resolution stereotactic assembly 274 is configured with the body 275 and template 276 as separate components, then a plurality of templates 276 with different patterns of holes 278 and distances, d, may be made available for use with the assembly 274. Different templates can be designed for different intended uses of the skull/brain interfaces (e.g., DC stimulation of a large area such as dorsolateral prefrontal cortex, DC stimulation of a small area such as an epileptic focus, measurement of signals from the brain, etc.). The low-resolution stereotactic assembly 274 also may be provided with blanks that can be formed into customized templates for a particular patient, for a particular intended use for a skull/brain interface, or according to the surgeon's preference. The templates 276 may be used to guide marking the scalp for location of skull/brain interfaces, where incisions in the scalp should be made, and/or where a drill or dilator(s) should be positioned for forming apertures or installing channels for the skull/brain interfaces described herein.

The low-resolution stereotactic assembly 274 is shown in FIG. 27 with the options of an orienting feature 280 to aid in orienting the assembly 274 on the patient's head with reference to an anatomical marker (the patient's ear in the case of FIG. 27) and a securing feature 282 to hold the assembly 274 on the patient's head (a strap in the case of FIG. #). In addition to or in lieu of one or more orienting features 280, the low-resolution stereotactic assembly 274 may be provided with an adhesive that permits the assembly 274 to be temporarily adhered to the patient's head.

Skull/Brain Interface Kits

One or more kits may be provided with components for facilitating the skull/brain interfaces described herein, both in the form of apertures and channels. A kit may contain items such as the overlay and/or low-resolution stereotactic assembly 274 described above.

A kit may also be configured to include a plurality of channels of various sizes, shapes and lengths. The lengths may be selected to accommodate skull thicknesses that vary from patient to patient, as well as surgeon preferences for the extent to which a given channel will traverse the thickness of the skull (e.g., all the way through (100% of the skull thickness) or partially through (such as 90% of the skull thickness). Additionally, channels having a plurality of inner lumens may be provided with inner lumens of different lengths.

A kit further may be configured to contain different types of channels, for example, plugs, cannula-like channels, and/or multi-lumen channels, etc. In this fashion, a kit may be customized for a particular application of a skull/brain interface.

In still other variations, a kit may be provided with a scalp electrode pad 45 or a scalp electrode pad assembly 46 as described herein with reference to FIGS. 3A and 3B.

In yet other variations, a kit may be provided that includes a stimulator to be used with a skull/brain interface alone or together with an accessory on which the stimulator or the electronics of the stimulator can be or is already mounted. Because the apertures or other fenestration or channels will facilitate focusing of the stimulation from the source to the target areas of the brain, the positioning of the stimulation source in the headpiece relative to the skull/brain interface does not have to be especially precise. For example, a washable hat or headpiece may be provided with a feature (such as a pouch) that allows it to accommodate a source of DC stimulation, and a DC stimulation that fits into the hat may or may not also be provided. The entire stimulation source may be selectively insertable into the hat, or just the electronics for the stimulation source may be removable. Alternatively, the stimulation source may be built into a helmet for use with skull/brain interfaces for particular indications or applications. For example, when a skull/brain interface is intended to be used for a performance-enhancing application as described hereinbelow, the stimulator or just at portion of the stimulation source (e.g., the electrode through which stimulation is delivered), may be located in a pilot's helmet for applications designed to improve visual acuity or alertness.

Gauging Skull Thickness

Installation of a skull/brain interface may be facilitated by a feature that allows the thickness of a patient's skull to be measured before an aperture is formed or a channel installed, and/or while an aperture is being formed, as with a drill. Ultrasonic reflections from the interface between the inner table and the cranial cavity can be analyzed in order to determine when a desired thickness of the skull has been traversed. A skull/brain interface kit may be provided with a tool or other device for measuring the thickness of a patient's skull at various locations as an aid for determining how deep to drill to form an aperture or aperture for receiving a channel, how far to insert a dilator, and/or which of several available channels to use (e.g., from among channels of a variety of lengths). In one variation, the tool may be an ultrasound tool. Alternatively, a drill may be provided with an ultrasonic transducer at the tip that allows the thickness of the skull forward of the drill to be continuously monitored during the drilling. For example, if a surgeon wishes to install a channel so that it traverses about 90% of the thickness of the skull in a particular region (i.e., so the channel extends almost all the way but not entirely through the skull), then the ultrasonic transducer may be relied upon to indicate to the surgeon when the drill tip is about 10% of the way away (or so many millimeters away) from breaching the skull and entering into the cranial cavity.

Deployment/Implantation of Transcranial Channels with Extracranial Extension(s)

In yet another variation, one or more transcranial channels together with an extracranial extension 300, as such a combination is described above in connection with FIG. 24, may be implanted in a patient.

The first and second portions 302 and 304 of an extracranial extension 300 may be implanted in the patient under the skin and positioned so that the first portion 302 can be located over the proximal end(s) 106 of the channels 100, the first end 306 of the second portion 304 connected to the first portion 302, and the second end 308 of the second portion 304 is positioned to interface with external equipment or a device with which to carry out the intended application (e.g., delivering neuromodulation through the extracranial extension 300 and channels 100, or measuring signals from the brain through the channels and the extension).

One position for the second end 308 of the second portion 304 might be at the base of the skull, neck, chest, or shoulder of the patient.

The extracranial extension 300 may be implanted before, concurrently with, or after implanting the channel(s) 100, and may be routed to the desired position for the second end 308 of the second portion 304 using techniques similar to those used by those skilled in the art to tunnel deep brain lead extensions for pulsatile electrical stimulation.

Any incisions or wounds created by reason of insertion of the channel(s) 100 and the positioning of the extracranial extension 300 and the second end 308 of the second portion 304 of the extracranial extension are then closed. Thereafter, the external equipment or devices necessary to carry out the intended application(s) for the channel(s) may be brought in proximity to the second end 308 and the application(s) may be commenced.

Deployment/Implantation of Transcranial Channel(s) with Transparenchymal Channel(s)

In another variation, one or more transcranial channels may be implanted in a patient's skull together with one or more transparenchymal channels 310 as such a combination is described in connection with FIGS. 25A and 25B, above.

Each transparenchymal channel 310 may be implanted using techniques similar to or the same as those used in implanting conventional deep brain electrodes (e.g., using frame-based or frameless stereotactic navigation, etc.). To facilitate these implant techniques, a removable stylet (not shown) may be placed within the ion-permeable lumen of the transparenchymal channel 310 or within a dedicated lumen (not shown) that is generally parallel to the ion-permeable lumen. A collector 314 (if used), may be coupled to the transparenchymal channel 310 and positioned to lie in the epidural space 316, between the inner layer 40 of the skull 20 and the dura mater 312 or, alternatively, completely under the dura mater 312. One or more transcranial channels 100 may then be implanted in the skull 20 over the transparenchymal channel(s) 310 and collector(s) 314 (if used).

Alternatively, a transparenchymal channel 310 may be provided that is entirely ion-permeable, at least on the side thereof that will be in contact with the brain, and placed in a sulcus of the brain. This variation may allow DC stimulation to be conducted to tissue located in a sulcus, with little loss of stimulation amplitude as compared to stimulation delivered at the gyral crown.

In still another variation, the transcranial channel 100 and transparenchymal channel 310 may be implanted simultaneously as, for example, when the transcranial channel 100 and transparenchymal channel 310 are provided as a single unit of ion-permeable material. In this variation, care must be taken to insure that there is enough slack left between the proximal end of the transcranial channel at the skull and the transparenchymal channel in the brain, to allow for some movement of the brain within the skull.

Any incisions or wounds created by reason of insertion of the channel(s) 100 are then closed. Thereafter, the external equipment or devices necessary to carry out the intended application(s) for the channel(s) may be brought in proximity to the channels and the application(s) may be commenced.

Using Transcranial Channels for DC Stimulation

Referring again to FIG. 2, for DC stimulation of a target area 24, either a conductive gel 14 or a saline-filled sponge (not shown) is applied to the exterior of the scalp 12 over the transcranial channel(s) 100. A first pole 10 of a current source can be brought in contact with the conductive gel 14 or saline-soaked sponge, and neuromodulation (e.g., polarization or stimulation) of the target area 24 may be commenced.

Figure 28A:
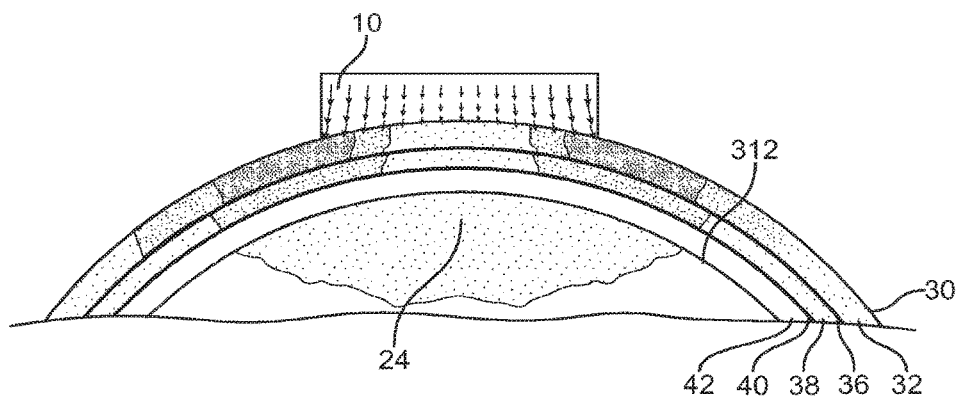
FIG. 28A is a schematic representation of a finite-element model (FEM) solution for transcranial direct current stimulation applied to the skull without using a transcranial channel to provide a skull/brain interface.
Figure 28B:
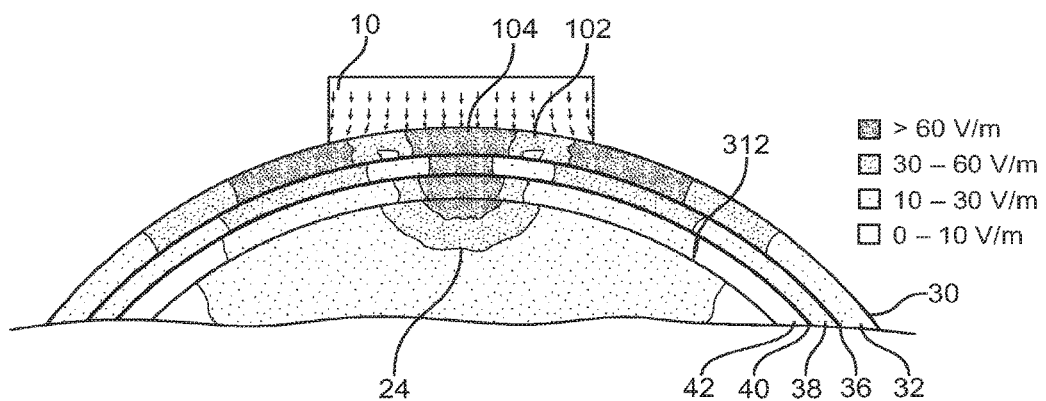
FIG. 28B is a schematic representation of a FEM solution for transcranial direct current stimulation applied to the skull using a transcranial channel to provide a skull/brain interface.

FIGS. 28A and 28B represent the results of a finite element model (FEM) analysis of the focality of DC stimulation before and after formation of a skull/brain interface (with a channel or simply with an aperture). The shading represents the relative magnitude of the electric field, with more concentrated shading corresponding to higher field magnitude. The arrows represent the direction and magnitude of current flow. The FEM solution (axisymmetric around the vertical axis) is provided using a five-sphere model taking into account skull layers: (1) sphere radii 7.8, 8.2, 8.3, 8.6, 8.7, and 9.2 cm respectively for the outer surfaces of brain, cerebrospinal fluid, inner compact bone, spongiform bone, outer compact bone, and scalp; and (2) conductivity of 0.45, 1.35, 0.0056, 0.45, 0.0056, and 0.45 S/m respectively for brain, cerebrospinal fluid, inner compact bone, spongiform bone, outer compact bone, and scalp. Stimulation was modeled as 9 Volt transcranial DC stimulation, applied between the electrode shown and an electrode applied at the opposite pole of the sphere (not shown). (It is noted that Bikson et al. have reported that 40 V/m is sufficient for significant neuromodulation (BIKSON et al., "Effects of Uniform Extracellular DC Electric Field On Excitability In Rat Hippocampal Slices In Vitro," *J. Physiol.* 557: 175-190 (2004).)

Non-Pulsatile and Near-DC Electrical Stimulation Using Transcranial Channels

Non-pulsatile and near-DC electrical stimulation of a target area in the brain may be carried out through one or more transcranial channels 100 in the same manner as DC stimulation may be carried out. That is, either a conductive gel 14 or a saline-filed sponge (not shown) is applied to the exterior of the scalp 12 over one or more implanted transcranial channels 100, which are located over a target area 24 of the brain. A first pole 10 of a current source can be brought in contact with the conductive gel 14 or saline-soaked sponge, and neuromodulation (e.g., polarization or stimulation) of the target area 24 may be commenced with non-pulsatile or near-DC waveforms, such as large amplitude waveforms, slowly varying oscillatory waveforms, and low frequency sine waves.

Pulsatile and AC Stimulation Using Transcranial Channels

As discussed previously herein, pulsatile and AC stimulation waveforms may be delivered through the electrode-tissue interface with good focality and few ill effects (provided that the waveforms used satisfy charge-density-per-phase limitations and that charge balancing is maintained). Nevertheless, and while transcranial channels are not necessary for focal delivery of these types of waveforms, focal delivery may still be facilitated by these devices. More particularly, in certain scenarios, scalp application of pulsatile and AC stimulation waveforms through a skull/brain interface as provided by a transcranial channel 100 may be deemed to be safer and less expensive than, for example, delivery of similar waveforms using an implanted pulse generator or neurostimulator.

Responsive or Feedback-Controlled Stimulation

In one variation, a device or system used with a skull/brain interface may be configured to have both stimulation and sensing capabilities. The sensing capability may include one or more electrodes that can sense physiological signals from the brain that are understood to correspond to, for example, a characteristic of a disorder or neurological state. The system may be configured to relate the stimulation delivered to the physiological signal(s) sensed in some manner, as in a closed-loop feedback arrangement. In one variation, the system may be preprogrammed to respond with stimulation in a particular form or characterized by particular parameters whenever a predetermined physiological signal or pattern of signals is sensed by the sensors (i.e., responsive stimulation). A form of control law or control laws additionally may be implemented in the system to modify the stimulation based on changes in the sensed signals. the stimulation device may be additionally provided with sensing electrodes, and the electrodes used to detect sleep stages, such as slow-wave sleep, or other neurological states.

Using Transcranial Channels for Iontophoresis

Transcranial channels 100 may be used to facilitate iontophoresis through the skull, allowing delivery of ions or charged molecules of biologically-active agents into the intracranial space. As noted above, these agents may include, but are not limited to, glutamate, acetylcholine, valproate, aspartate, gamma amino butyrate, adrenocorticotropic hormone (ACTH), cortisol, beta endorphin, and serotonin. Scalp electrodes may be provided and coated or infiltrated with one or more of the agents intended for delivery to a target area or target areas of the brain. These agents may also be mixed with a conductive gel or saline solution, or simply applied to the region of the scalp between the stimulating electrode and the transcranial channel 100.

Using Transcranial Channels to Stimulate with Light

Transcranial channels 100 may be used to conduct light for modulating the activity of neural tissue. More particularly, and by way of example, variations of the channels 100 may be constructed partially or substantially of material that is transparent, essentially transparent, semi-transparent, or selectively transparent to certain selected wavelengths of light. Since the external light directed at the skull ordinarily would be significantly diffused and attenuated before any of it reached the brain, use of the channels 100 as a conduit for light applied at the scalp would facilitate optical neuromodulation. It will be apparent to those with skill in the art that the same channel could be used to conduct light as well as electrical stimulation, such as DC stimulation, to target areas of the brain.

Scalp EEG Using Transcranial Channels

Use of one or more transcranial channels 100 in measuring signals from the brain, may reduce the blurring of the signals that otherwise occurs in scalp EEG without the channels (i.e., scalp EEG acquired through the relatively nonconductive skull). Comparable to the manner in which a transcranial channel will reduce dispersal of current that otherwise occurs in the application of tDCS without a channel, the net electrical field and current produced by neural activity will be more faithfully reproduced on the surface of the scalp using one or more channels, where they then can be measured using conventional scalp EEG equipment.

Moreover, a plurality of transcranial channels 100 implanted above one or more regions of interest 24 in the brain, or a single channel 100 with a plurality of inner lumens 180 or a longitudinally divided lumen, may be used to more faithfully reproduce on the scalp the spatial distribution of electrical fields and currents produced by neural activity in those regions, and this signal may be measured by a conventional, multi-channel scalp EEG. The better quality, higher resolution EEG signals may be more conducive than are conventionally obtained signals for applications such as using the signals for prosthetic control.

It will be appreciated by those with skill in the art that a single transcranial channel 100 may be used for dual applications, for example, conduction of a source of DC stimulation and conduction of signals for EEG measurement. Because many EEG signals of interest are time-varying signals, they may be separated by well-known techniques from artifacts that may be induced by the DC stimulation.

EEG electrodes may be placed against the scalp in the conventional manner, under the DC stimulation current electrode. Alternatively, the EEG electrodes may be constructed as part of the DC current electrode assembly. Still another alternative would be to use an electrode simultaneously for DC stimulation and as an EEG sensor, using amplification and signal separation techniques as are well known in the art. In one variation, the EEG signal may be processed to yield a measurement of epileptiform or seizure activity, and this measurement then used to modulate the amplitude of inhibitory transcranial DC stimulation, in an effort to provide optimal reduction of epileptiform or seizure activity.

Impedance Plethysmography and Tomography Using Transcranial Channels

A transcranial channel 100 provides a known path through the otherwise relatively nonconductive skull; thus it will be appreciated by those skilled in the art that a channel 100 can facilitate measurement of brain perfusion changes using electrical impedance plethysmography. It will further be appreciated that use of a plurality of transcranial channels 100 may facilitate electrical impedance tomography based on similar principles.

Optical Imaging and Tomography Using Transcranial Channels

As noted above, variations of transcranial channels 100 can be constructed of materials that are transparent, essentially transparent, semi-transparent, or selectively transparent to selected wavelengths of light. Without a channel in place, the skull causes significant diffusion and attenuation of light as well as electrical current. By eliminating the scattering that would otherwise be caused by the skull in a selected region and by providing a defined path for direct light transmission through the skull, a transparent, essentially transparent, semi-transparent, or selectively transparent transcranial channel 100 may facilitate optical measurement or optical tomography applied at the scalp.

It will be appreciated by those with skill in the art that these variations of transcranial channels may also be ion-conductive, allowing one channel to be used to facilitate both optical and electrical neurosensing.

Use of a Transcranial Channel to Cool the Brain

A transcranial channel 100 designed for the purpose of providing a skull/brain interface through which heat can be withdrawn from the interior of the skull, as described in connection with FIGS. 18A and 18B above, can be used to cool a target area 24 of the brain, such as an epileptic focus. In this variation, after the channel is implanted and any wound closed, a heat-absorbing or cooling device 224, such as a thermoelectric device, a device or chamber through which a saline solution is pumped, or an ice pack, etc. may be brought in proximity to the thermally conductive element(s) of the channel 100 to accomplish the transfer of heat from, or cooling of, the target area. The heat-absorbing or cooling device may be selectively activated or selectively brought into the vicinity of the proximal end 106 of the channel, for example, whenever a sensor detects a temperature in excess of a predetermined limit or limits. As is the case with any of the methods described herein, multiple channels 100 may be provided in order to accomplish the energy transfer.

In another variation of this method, energy may be transferred from a source external to the skull to the interior of the skull, such as in a high intensity focused ultrasound ("HIFU") application using, for example, the transcranial channel 100 described in connection with FIGS. 19 and 20 above. The skull/brain interface provided by a channel 100 that is substantially transparent to ultrasound will tend to prevent distortion of the ultrasound by the skull bone and help to focus the ultrasound more precisely on the target area(s) 24 of the brain. This technique may be used, for example, to ablate brain tissue or to precisely create lesions in the brain without resorting to more invasive brain surgery procedures.

In some embodiments, imaging such as computed tomography (CT) scans, Positron Emission Tomography (PET), Magnetic Resonance Imaging (MRI), and functional magnetic resonance imaging (fMRI), may be used to help determine where to place the transcranial channel or channels, based on the location, condition and/or nature of various brain structures.

Additional Aspects of Stimulation Used with the Skull/Brain Interfaces

When a skull/brain interface is used in a system for delivering a form of stimulation to the patient to encourage neuromodulation (e.g., to excite or inhibit neural activity), the system may be provided with various features to enhance control of the stimulation, potentially improve the results of certain types of stimulation or stimulation delivered for certain indications, and to facilitate situating a stimulation source in the vicinity of the skull/brain interface (or in the vicinity of an end of an extracranial extension connected to a skull/brain interface). Some of these features are described in more detail hereinbelow.

Limited Patient-Controlled Stimulation in a Portable Stimulator

A stimulation source used with the skull/brain interfaces described herein desirably is portable so that the source can be used when the patient is variously situated, and not limited to use, for example, only when a patient is in an operating room or clinician's office. A stimulation source may be configurable so that it fits into a hat or helmet, as described previously herein.

In some variations, the stimulation source may be controllable or partially controllable by a patient or a caregiver. A stimulation source may be configured so that the patient or caregiver may control a predetermined subset of the parameters that define and/or control generation of the stimulation, such as the relative strength of the stimulation. Alternatively, all of stimulation parameters may be fixed but the patient may be provided with limited discretion to decide when stimulation is delivered or how often it is delivered up to some maximum or below some threshold (e.g., no more than 10 doses of electrical stimulation or a drug per 24-hour period, no more often than one dose every 30 seconds, etc.) Similarly, the stimulation source and/or skull/brain interface may be configured to disallow further stimulation or doses of stimulation device when a prescribed amount is exceeded or a prescription expires.

In other variations, a wireless or wired remote may be provided to operate a stimulation or other neuromodulation source. For example, a remote may be used to operate a hat-mounted or head-mounted stimulator. The remote control may enable, for example, patient-controlled stimulation. In an embodiment, the remote control operations may be performed as part of the operation of another device, such as a computer system that stores and/or performs other operations on sensed data or controls or manages stimulation.

Current Control and Impedance Measurement

In one variation, a stimulator configured to provide stimulation to neural tissue via a transcranial channel may include a current-controlled stimulation source. The current-controlled stimulation source can be used to control therapy despite impedance variations or changes in the electrode/scalp interface. Alternately, the impedance of the stimulation path could be detected, for example between one stimulating electrode and another stimulating electrode of opposite polarity, or between one stimulating electrode and a return electrode. If the impedance is not within an acceptable range, stimulation may be ceased, attenuated, or otherwise modified, and/or the patient may be alerted.

Examples of Some Specific Indications for Skull/Brain Interfaces

Generally, it is intended that the skull/brain interfaces described herein be used both in lieu of more invasive options (such as deep brain leads connected to implanted neurostimulators) and less invasive (but also less focused) options such as transcutaneous electrical stimulation or DC stimulation delivered through the intact skull.

A number of indications for the skull/brain interfaces are identified throughout this disclosure, such as diagnosis of, relief of the symptoms of, or reversal or repair of damage caused by, neurological dysfunction caused by neurological damage, neurologic disease, neurodegenerative conditions and/or other conditions.

The neurological dysfunction may be related to, for example and not by way of limitation, epilepsy, movement disorders such as Parkinson's disease, Huntington's disease, essential tremor, stroke, traumatic brain injury, cerebral palsy, multiple sclerosis, Alzheimer's disease, dementia (including frontotemporal dementia and multi-infarct dementia), memory disorders, stroke rehabilitation, aphasia, mild cognitive disorders, depression, bipolar disorder, anxiety disorders, obsessive-compulsive disorders, eating disorders, Tourette's syndrome, restless leg syndrome, coma (especially affecting the frontal lobe), schizophrenia, post-traumatic stress syndrome or other neuropsychiatric affect disorders, learning disorders (including attention-deficit-hyperactivity disorders), autism, speech disorders, auditory or hearing disorders (e.g., tinnitus), craving and addictive disorders, sleep disorders (including narcolepsy and excessive daytime sleepiness disorder), headaches including migraine headaches, tension headaches and cluster headaches, and other dysfunctions caused by brain injury or characterized by chronic pain.

More specific examples of some contemplated indications for the skull/brain interfaces and/or methods for implementing the same are described hereinbelow.

Sleep Staging and Selective Stimulation

Neurological states occurring during sleep are of interest with respect to a variety of neurological disorders and conditions (for example, epileptic seizures may occur more or less frequently during certain sleep stages in certain patients, certain cognitive processes may be more active during certain sleep stages than during wakefulness, etc.).

In one variation of a device or system to be used with a skull/brain interface as described herein, the system may be configured to have sensors in the form of electrodes to monitor a patient during sleep and to detect one or more stages of sleep, such as slow-wave sleep, or other neurological states occurring during sleep. The device or system may be further configured to use the monitored or sensed information to decide when to deliver stimulation or what parameters to use in generating or delivering stimulation in a responsive or closed-loop feedback manner. For example, the monitored or detected information may be used by the system to apply stimulation selectively during one or more sleep stages or when another neurological state is detected, such as a state that is believed to be involved in memory consolidation. The monitored or detected information may also be used to vary stimulation delivered based on changes in the sensed information, such as delivering one form of stimulation when a first sleep stage manifests, and then different or no stimulation when the patient transitions to another sleep stage.

Performance-Enhancing Stimulation

In addition to being used for treating neurological disorders, it is contemplated that the skull/brain interfaces described herein may be used together with a stimulation source and/or a device for measuring physiological signals from the brain in an effort to enhance a patient's performance in one or more areas, such as visual acuity, memory, or mental alertness. Optionally, the stimulation and/or stimulation detection system may be provided, as described above, in a pilot's helmet or as temporarily positionable in a headpiece, to bring the system in the vicinity of the skull/brain interface(s).

Some examples of performance-enhancing indications are described in more detail below.

Vision-Enhancing Indications

More particularly, it is anticipated that transcranial channels, apertures or fenestrations as disclosed herein may be used to facilitate the effect of tDCS on the visual cortex or on desired part(s) of the visual cortex. For example, anodal DC stimulation introduced through one or more skull/brain interface to focus stimulation over the occipital cortex is expected to reduce the threshold for preception of phosphenes. Conversely, cathodal tDCS delivered through one or more skull/brain interfaces located over the occipital cortex is expected to increase the threshold for perception of phosphenes.

Memory-Enhancing Indications

It is envisioned that the transcranial channel(s) or aperture(s) or fenestration(s) disclosed herein may be used to facilitate the effect of tDCS on the DLPFC or other regions of the brain related to memory function. For example, anodal DC stimulation introduced through a skull/brain interface or interface(s) deployed to cause neuromodulation of the dorsolateral prefrontal cortex (DLPFC) is expected to increase the accuracy with which a patient can perform a working memory task. The same anodal DC stimulation delivered with one or more skull/brain interfaces deployed at frontolateral locations during slow-wave sleep is expected to increase retention of word pairs in a declarative memory task.

Enhancing Verbal Fluency

It is envisioned that transcranial channel(s) or aperture(s) or other fenestration(s) as disclosed in this application may be used to facilitate the effect of tDCS on left prefrontal cortex or other regions of the brain related to verbal fluency. For example, anodal tDCS delivered through a skull/brain interface or interfaces to the left prefrontal cortex is expected to increase verbal fluency, while cathodal tDCS delivered to the same location is expected to mildly decrease verbal fluency.

Inhibition of Executive Function to Induce Creative or Savant State

It is envisioned that cathodal tDCS delivered to the prefrontal cortex or other regions of the brain understood to be responsible for executive function may be used to disinhibit creative functions or induce a savant-like state, and that transcranial channel(s), aperture(s), or fenestration as disclosed in this application may be used to facilitate this effect of tDCS on prefrontal cortex or other regions of the brain related to executive function. Conversely, anodal tDCS may be used to potentiate (promote or strengthen) executive function and treat symptoms of autism.

Other performance-enhancing indications for skull/brain interfaces according to the invention with stimulation and stimulation/detection systems will be apparent to those with skill in the art.

Using DC Fields for Axonal Regrowth

It is envisioned that transcranial channel(s), aperture(s) or other fenestration(s) as disclosed herein may be used as skull/brain interfaces for an electrical field source located outside the body, to produce a controlled electrical field within or near tissue such as the brain or other nervous tissue. It is known that DC electrical fields are known to guide axonal growth and stem cell migration. Thus, the controlled electrical field induced through the interface(s) is expected to potentiate, inhibit and/or direct axonal growth or regrowth, or desirable migration of endogenous or exogenous cells within the tissue.

Using DC Stimulation for Cognitive Dysfunction as in Alzheimer's Disease

It is envisioned that transcranial channel(s), aperture(s) or other fenestration(s) as disclosed herein may be used to improve working memory or cognitive function in, for example: cases of dementia, such as frontotemporal dementia or multi-infarct dementia; cases of mild cognitive impairment; learning disorders; or other disorders affecting memory and cognition. For example, anodal tDCS delivered through a skull/brain interface or interfaces bilaterally over temporoparietal areas is expected to increase accuracy of a word recognition task in Alzheimer's disease patients.

Psychiatric Disorders (e.g., Schizophrenia and Bipolar Disorder)

Transcranial magnetic stimulation of the prefrontal cortex is currently under study to treat such psychiatric disorders as schizophrenia and bipolar disorder. It is envisioned that transcranial channel(s), aperture(s) or fenestration(s) as disclosed herein may be used to facilitate the effect of tDCS on cortical areas, such as the prefrontal cortex, related to these psychiatric disorders. A DC stimulation source and the skull/brain interfaces according to the invention may be used alone or in combination with one or more deep brain elements, such as the transparenchymal channels described hereinabove, to facilitate penetration of the neuromodulatory effect to deeper brain structures, such as ventral striata, related to these psychiatric disorders.

Stimulation for Treating Coma Patients

It is envisioned that transcranial channel(s), aperture(s) or fenestration(s) as disclosed herein may be used to improve neurological function in, for example, cases of coma or cases of minimally-conscious state (MCS). For example, anodal tDCS delivered through a skull/brain interface or interfaces over cortex is expected to increase neural activity in the stimulated region. A stimulation source, such as DC current, and the skull/brain interfaces according to the invention may also be used alone or in combination with one or more deep brain elements, such as the transparenchymal channels described hereinabove, to facilitate penetration of the neuromodulatory effect to deeper brain structures, such as intralaminar nuclei of the thalamus or tissue comprising the reticular activating network, expected to influence neurological arousal.

Tinnitus

It is anticipated that transcranial channel(s), aperture(s) or fenestration(s) as disclosed herein may be used to focus tDCS for treatment of tinnitus. For example, anodal DC stimulation introduced through one or more skull/brain interfaces to focus stimulation over the left temporoparietal area is expected to reduce the symptoms of tinnitus.

DC Stimulation for Language and Verbal Skills (e.g., Treatment for Aphasia)

It is anticipated that transcranial channel(s), aperture(s) or fenestration(s) as disclosed herein may be used to focus tDCS for treatments related to language or verbal performance. For example, anodal DC stimulation introduced through one or more skull/brain interface to focus stimulation over the left perisylvian area is expected to enhance performance in normal patients whereas DC stimulation, such as cathodal DC stimulation, introduced over the left frontotemporal area is expected to result in improvement in language performance in patients with aphasia.

Stimulation for Treating Pain

Headaches

Headaches, for example migraine headaches, are believed to be in part a disorder of abnormal cortical excitability or abnormal cortical inhibition, and attempts to treat headache using TMS are being investigated. Both tDCS and repetitive (1 Hz) electrical stimulation have been shown in rats to modulate the velocity of cortical spreading depression, a phenomenon believed to be related to migraine. It is envisioned that transcranial channel(s), aperture(s) or fenestration(s) as disclosed herein may be used to focus tDCS or repetitive electrical stimulation for modulating cortical excitability for treatment of headache, including migraine headache, tension headache, cluster headache, and other types of headache.

Neuropathic Pain

It is envisioned that transcranial channel(s), aperture(s), or other fenestration(s) as disclosed herein may be used to facilitate the effect of tDCS on primary motor cortex (M1), somatosensory cortex, DLPFC, or other regions of the brain related to pain and pain processing, in order to treat pain disorders. Examples of pain disorders include post-herpetic pain, phantom limb pain, failed back surgery syndrome (FBS), complex regional pain syndrome (CPRS), and neuropathic pain.

In one variation, channels, apertures, or fenestrations would be placed over multiple pain-related cortical regions, and stimulation may be delivered to each region with less blurring and overlap than would occur in the absence of the channels, apertures or fenestrations.

In another variation, anodal DC stimulation introduced through one or more skull/brain interface to focus stimulation over the primary motor cortex (M1) is expected to reduce pain due to fibromyalgia and traumatic spinal cord injury.

In an additional variation, cathodal tDCS delivered through a skull/brain interface or interface(s) located over the somatosensory cortex is expected to reduce sensation of acute pain.

In a still other variation, anodal stimulation focused through a skull/brain interface on the dorsolateral prefrontal cortex (DLPFC) is expected to modulate a patient's emotional response to pain (such as post-herpetic pain, phantom limb pain, failed back surgery syndrome, complex regional pain syndrome and neuropathic pain generally).

Autism

It is anticipated that transcranial channel(s), aperture(s) or fenestration(s) as disclosed herein may be used to focus tDCS for treatments for autism. For example, anodic DC stimulation focused through a skull/brain interface on the left frontotemporal cortex is expected to benefit patients with autism or autistic symptoms.

Stimulation for Neuroprotection for Stroke

Stimulation of deep brain nuclei such as the fastigial nucleus is believed to yield neuroprotection against excitotoxic and ischemic injury such as during stroke. It is envisioned that transcranial channel(s), aperture(s) or other fenestration(s) as disclosed herein, used in conjunction with one or more transparenchymal channels as described hereinabove, would facilitate use of transcranial direct current or non-DC transcranial electrical stimulation for this purpose.

Stimulation for Addictions and Cravings, and Involuntary or Semi-Voluntary Behaviors tDCS delivered to left and right dorsolateral prefrontal cortex (DLPFC) has been shown to reduce cravings for smoking and food. It is envisioned that channel(s), aperture(s) or fenestration(s) as disclosed herein may be used to facilitate such effects of tDCS, in order to treat such disorders as addiction and obesity. Similarly, it is envisioned that applying DC stimulation through skull/brain interfaces will be effective in managing or controlling other semi-voluntary or involuntary behaviors such as those characterizing obsessive-compulsive disorder and Tourette's syndrome.

Stimulation for Addictions, Cravings, and Involuntary/Semi-Voluntary Behaviors

TMS delivered to visual cortex has been shown to improve visual function in amblyopia. It is envisioned that tDCS may be used to similar effect, and that channel(s), aperture(s) or fenestration(s) as disclosed herein may be used to facilitate such effects of tDCS, in order to treat such disorders as amblyopia.

Although the above systems, devices and methods have been described in the context of transcranial channels, it is intended that the embodiments have useful application elsewhere in the body, for example, anywhere that neural tissue is shielded by tissue such as bone or a vertebral disk. In one specific example, a channel may be placed through a vertebra or between two vertebrae, and used to facilitate spinal cord neuromodulation via an extraspinal or entirely extracorporeal stimulation device.

The systems, devices and methods described herein may be useful in the diagnosis, symptom relief, reversal or repair of damage related to neurological trauma or neurodegenerative conditions, otherwise improving patient quality of life, and in enhancing performance in otherwise normally-functioning patients.

The systems, devices and methods described herein may be used to detect electrical activity from neurons or generate electrical activity in neurons using electrical neurostimulation in conjunction with an adjunctive or synergistic procedure, including but not limited to a pharmacological therapy, an auditory or visual therapy or warning of the onset or imminent onset of an event or condition, a physical or behavioral therapy, and a procedure to implant cells such as stem cells.

It will be appreciated that the above-disclosed and other features and functions, or alternatives thereof, may be desirably combined into many other different systems or applications. It will also be appreciated that various presently unforeseen or unanticipated alternatives, modifications, variations or improvements therein may be subsequently made by those skilled in the art which are also intended to be encompassed by the following claims.

What is claimed is:

1. A system for introducing a form of neuromodulation to a patient, the system comprising:
   at least one transcranial channel configured to be implanted in an aperture in the skull of the patient, and comprising an outer wall defining an interior cavity, and an ion-permeable substance at least partially filling the interior cavity, the ion-permeable substance configured to facilitate conduction of the form of neuromodulation;
   at least one scalp electrode pad comprising an orienting feature configured to engage an ear of the patient to thereby position the at least one scalp electrode pad in a vicinity of the at least one transcranial channel near a target area of neural tissue;
   a stimulation source electrically coupled to the at least one scalp electrode pad and configured to generate the form of neuromodulation and deliver the form of neuromodulation to the patient through the at least one scalp electrode pad and the at least one transcranial channel; and
   a securing feature coupled to the at least one scalp electrode pad and configured to secure the at least one scalp electrode pad at the vicinity of the at least one transcranial channel.

2. The system of claim 1, wherein the at least one scalp electrode pad is configured to be positioned in abutting contact with a scalp of the patient.

3. The system of claim 1, wherein the target area of neural tissue is an occipital cortex, and the form of neuromodulation is anodal direct current stimulation.

4. The system of claim 1, further comprising a control device, wherein:
   the control device and the stimulation source are configured for wireless communication,
   the stimulation source is configured to generate the form of neuromodulation in accordance with at least one operating parameter; and
   the control device wirelessly controls the at least one operating parameter of the stimulation source.

5. The system of claim 4, wherein the at least one operating parameter of the stimulation source corresponds to a strength of an electrical stimulation provided by the stimulation source.

6. The system of claim 4, wherein the at least one operating parameter of the stimulation source corresponds to a number of electrical stimulations provided by the stimulation source during a period of time.

7. The system of claim 1, further comprising a control device, wherein:
   the control device is configured to enable a user-initiated delivery of the form of neuromodulation by the stimulation source; and
   the stimulation source is configured to disallow the user-initiated delivery of the form of neuromodulation when a threshold amount of the form of neuromodulation is exceeded.

8. The system of claim 1, wherein the form of neuromodulation is direct current stimulation and the stimulation source is configured to adjust the direct current to keep at least one parameter within a predetermined range while stimulation is being delivered.

9. The system of claim 1, wherein the ion-permeable substance comprises a hydrogel.

10. The system of claim 1, wherein the ion-permeable substance comprises a saline solution.

11. The system of claim 1, wherein the ion-permeable substance comprises one or more of the following: porous silicone, a porous polyurethane, a saline solution, and a hydrogel.

12. The system of claim 1, wherein the ion-permeable substance comprises a porous mass constructed by sintering together particles of a nonporous polymer, wherein the nonporous polymer comprises one or more of the following: a polyurethane, a polytetrafluoroethylene, a polyetheretherketone, a polyester, and a polyamide.

13. The system of claim 1, wherein the ion-permeable substance is provided in an open-pore sponge.

* * * * *